US012784872B2

(12) United States Patent
Gargiulo

(10) Patent No.: US 12,784,872 B2
(45) Date of Patent: Nov. 3, 2026

(54) METHOD FOR ENGINEERING SYNTHETIC CIS-REGULATORY DNA

(71) Applicant: Max-Delbrück-Centrum für Molekulare Medizin in der Helmholtz-Gemeinschaft, Berlin (DE)

(72) Inventor: Gaetano Gargiulo, Berlin (DE)

(73) Assignee: MAX-DELBRÜCK-CENTRUM FÜR MOLEKULARE MEDIZIN IN DER HELMHOLTZ-GEMEINSCHAFT, Berlin (DE)

( * ) Notice: Subject to any disclaimer, the term of this patent is extended or adjusted under 35 U.S.C. 154(b) by 1381 days.

(21) Appl. No.: 17/273,821

(22) PCT Filed: Sep. 5, 2019

(86) PCT No.: PCT/EP2019/073711
§ 371 (c)(1),
(2) Date: Mar. 5, 2021

(87) PCT Pub. No.: WO2020/049106
PCT Pub. Date: Mar. 12, 2020

(65) Prior Publication Data

US 2021/0343368 A1 Nov. 4, 2021

(30) Foreign Application Priority Data

Sep. 5, 2018 (EP) .................................... 18192715

(51) Int. Cl.
*G16B 20/30* (2019.01)
*C12N 15/63* (2006.01)
(Continued)

(52) U.S. Cl.
CPC ............. *G16B 20/30* (2019.02); *C12N 15/63* (2013.01); *C12N 15/64* (2013.01); *C12Q 1/6809* (2013.01);
(Continued)

(58) Field of Classification Search
CPC ........ G16B 20/30; G16B 25/10; G16B 40/00; C12N 15/63; C12N 15/64; C12Q 1/6809; C12Q 1/6897
See application file for complete search history.

(56) References Cited

U.S. PATENT DOCUMENTS

| | | | | |
|---|---|---|---|---|
| 9,868,786 B2 | 1/2018 | Finkelman et al. | | |
| 2006/0160108 A1* | 7/2006 | Romanov | ............ | C12Q 1/6897 435/325 |

(Continued)

FOREIGN PATENT DOCUMENTS

| | | |
|---|---|---|
| EP | 2494058 B1 | 4/2017 |
| WO | 200149868 A1 | 7/2001 |

(Continued)

OTHER PUBLICATIONS

Company, Carlos, et al. "Logical design of synthetic cis-regulatory DNA for genetic tracing of cell identities and state changes." Nature Communications 15.1 (2024): 897. (Year: 2024).*

(Continued)

*Primary Examiner* — Jesse P Frumkin
(74) *Attorney, Agent, or Firm* — DINSMORE & SHOHL LLP

(57) ABSTRACT

The invention relates to methods for generating cell-type specific expression cassettes and reporter vectors, as well as nucleic acid constructs that can be generated by such methods. The cell-type specific expression cassettes and reporter vectors are characterized synthetic cis-regulatory DNA, also termed synthetic locus regions (sLCRs). sLCRs allow for a cell-type specific expression of reporter or effector genes. The invention further relates to various uses of the reporter vectors, including the determination of a property of a cell, preferably a cell type, state or fate transition, in gene and viral therapy, drug discovery or validation.

12 Claims, 35 Drawing Sheets
(18 of 35 Drawing Sheet(s) Filed in Color)
Specification includes a Sequence Listing.

(51) Int. Cl.

| | |
|---|---|
| ***C12N 15/64*** | (2006.01) |
| ***C12Q 1/6809*** | (2018.01) |
| ***C12Q 1/6897*** | (2018.01) |
| ***G16B 25/10*** | (2019.01) |
| ***G16B 40/00*** | (2019.01) |

(52) U.S. Cl.

CPC ........... *C12Q 1/6897* (2013.01); *G16B 25/10* (2019.02); *G16B 40/00* (2019.02)

(56) References Cited

U.S. PATENT DOCUMENTS

| | | | | |
|---|---|---|---|---|
| 2014/0271551 | A1 | 9/2014 | Hirsch et al. | |
| 2016/0222115 | A1 | 8/2016 | Huang et al. | |
| 2017/0002319 | A1 * | 1/2017 | D'Alessio | G16B 40/00 |
| 2018/0092929 | A1 | 4/2018 | Finkelman et al. | |
| 2019/0024118 | A1 * | 1/2019 | Tagliatela | C12N 15/113 |

FOREIGN PATENT DOCUMENTS

| | | | | |
|---|---|---|---|---|
| WO | 200206495 | A2 | 1/2002 | |
| WO | 2003004682 | A2 | 1/2003 | |
| WO | WO-2007025205 | A2 * | 3/2007 | G16B 40/00 |
| WO | 2008107725 | A1 | 9/2008 | |
| WO | 2012101191 | A1 | 8/2012 | |
| WO | 2015071748 | A1 | 5/2015 | |
| WO | 2015110449 | A1 | 7/2015 | |

OTHER PUBLICATIONS

Z. Guo et al, "Gene Transfer: the Challenge of Regulated Gene Expression"; Trends in Molecular Medicine, Elsevier Current Trends, vol. 14, No. 9, Sep. 1, 2008, pp. 410-418.

G. Gargiulo et al, "Cellular Specificity of Expression and Regulation of *Drosophila* Vitelline Membrane Protein 32E Gene in the Follicular Epithelium: Identification of CIS-Acting Elements"; Mechanisms of Development, Elsevier Science Ireland Ltd, vol. 35, No. 3, Nov. 1, 1991, pp. 193-203.

Examination Report (Communication pursuant to Art. 94(3) EPC dated Apr. 3, 2025 in the parallel European Patent Application No. 19762405.9.

* cited by examiner b c d g h f g h c b a b a b a b

Fig. 13 (cont,)
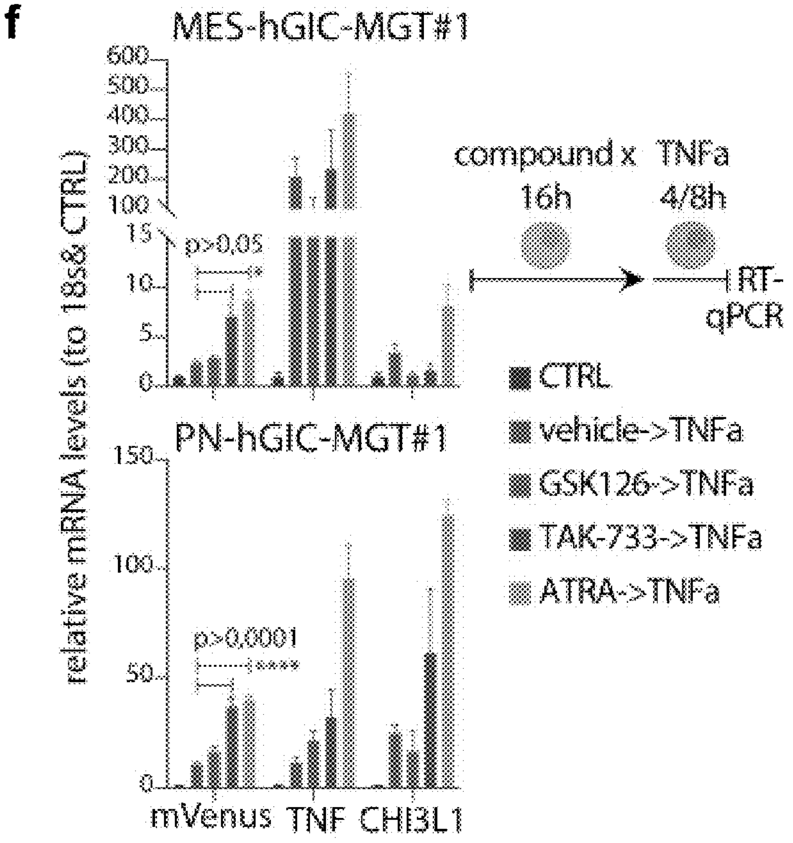
Fig. 14
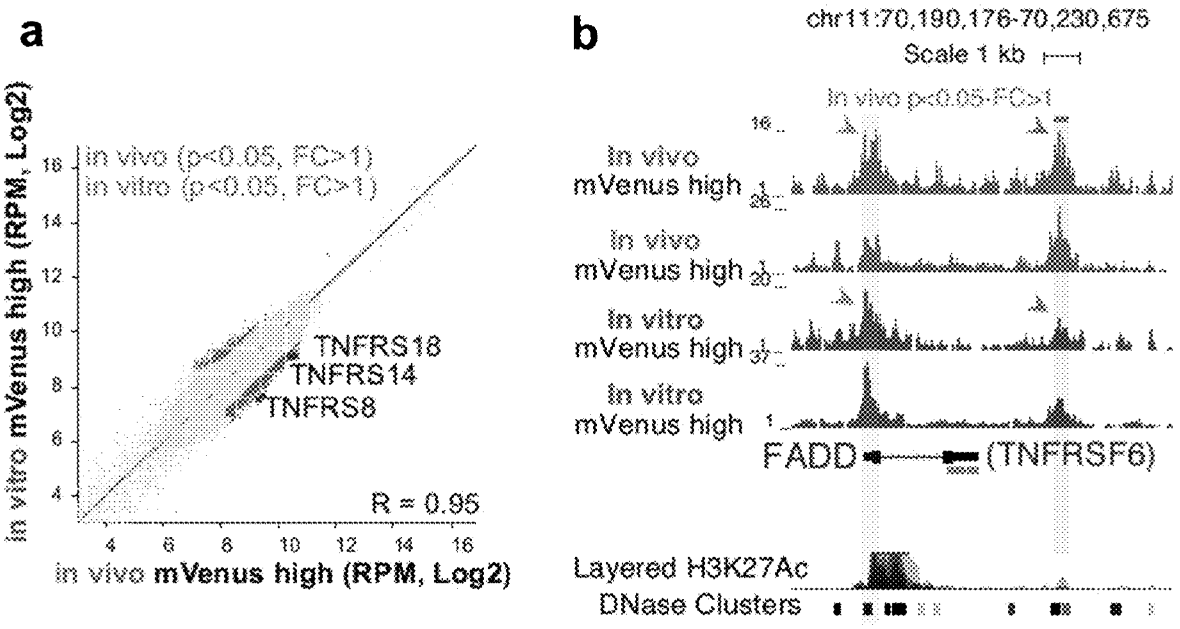

c d d e f g b c d e

METHOD FOR ENGINEERING SYNTHETIC CIS-REGULATORY DNA

CROSS-REFERENCE TO RELATED APPLICATIONS

This application is a § 371 National Stage Entry of International Application No. PCT/EP2019/073711, filed Sep. 5, 2019, which claims priority to EP 18192715.3, filed Sep. 5, 2018.

The invention relates to methods for generating cell-type specific expression cassettes and reporter vectors, as well as nucleic acid constructs that can be generated by such methods. The cell-type specific expression cassettes and reporter vectors are characterized synthetic cis-regulatory DNA, also termed synthetic locus regions (sLCRs). sLCRs allow for a cell-type specific expression of reporter or effector genes. The invention further relates to various uses of the reporter vectors, including the determination of a property of a cell, preferably a cell type, state or fate transition, in gene and viral therapy, drug discovery or validation.

BACKGROUND OF THE INVENTION

Expression cassettes and reporter vectors have a wide range of applications in basic research, drug screening diagnosis or gene therapy.

Selectively identifying cell type-specific identities is essential for understanding biological processes in which a diverse set of cell types contributes to tissue homeostasis. Ideally, this approach would also be informative in disease settings involving alterations in tissue homeostasis including metabolic, immunological, neurological or psychiatric disorders as well as inflammation and cancer. In developmental settings, this is traditionally achieved using lineage tracing[1].

Among the most well-known examples, lineage tracing of Fbx15 expression led to the discovery of defined factors capable of reprogramming fibroblasts into pluripotent cells[49], and lineage tracing of Lgr5 expression enabled the identification of bona fine colon and small intestine stem cells[2], which was later shown to mark several other adult tissue stem cells[3]. The parallel development of sophisticated reporter strategies allows for single-cell resolution in analyzing multiple lineages.

Traditionally, several genetic tracing approaches have been exploited to generate reporter mice for cell-type specific genetic manipulation and cell labeling (e.g. LacZ, mGmT, Brainbow and Confetti systems, Mosaic Analysis with Double Markers—MADM, etc.). These strategies can reveal complex neuronal connection patterns[4] and tackle outstanding questions such as the cell of origin for a tumor in a living organism[5]. More recently, Optogenetics and CRISRP/Cas9 based strategies added further flexibility in obtaining more quantitative readouts.

The use of reporter strategies based on adult stem cell biology can simultaneously inform on the origin of a tissue and it's aberrant homeostasis[6 7 8]. Genetic reporters reflecting well characterized pathways can lead to a deeper understanding of complex signaling dichotomy such as transforming growth factor counteracting bone morphogenetic protein (BMP) signaling during hair follicle homeostasis[9].

In cancer, this approach critically revealed that aberrant homeostasis can be causal to therapy resistance[10] or that a regeneration potential and tumor susceptibility may be shared among some organs, or markedly different in others[11]. Quantitative spatiotemporal patterning dynamics can be revealed by designing synthetic reporters based on transcription factor binding sites[47]. As inferred from these and several other studies, the choice of the genetic reporter is a critical factor for conclusively addressing sophisticated and complex biological questions. This is particularly valid in development or disease settings governed by multiple factors and complex interactions[12].

In these settings, the ability to flexibly design synthetic reporters that intercept multiple pathways in a single genetic cassette will certainly prove to be a major asset, however current approaches are still limited.

For example, presently employed approaches for genetic tracing vectors rely on the use of cell-type, pathway specific or synthetic promoters or enhancers that are coupled to a reporter gene or a functional effector.

The use of cell-type-specific promoters is based on placing the reporter gene or functional effector after the minimal promoter of a signature gene of the cell-type of interest. It allows thereby for the specific transcriptional activation of a given reporter or effector as mediated the promoter for the given gene. Cell-type-specific vectors offer the possibility to use one given gene as a proxy of a cell state or developmental stage.

One example is the use of the Nestin promoter in order to mark neural progenitor cells. This approach is widely used and allows researchers to direct the activation of specific reporters or effectors in undifferentiated cells.

Significant limitations to these approaches are the necessity of prior knowledge on the signature genes and the assumption that regulatory elements for said genes are known and in close proximity to the transcriptional start site. Furthermore, the approaches suffer from an insufficient specificity of a single gene to depict complex regulatory systems. A cumbersome solution to this problem entails the cell type-specific identification of all the specific enhancers for any given cell type of interest followed by the selection of one of such elements and its cloning upstream a minimal viral promoter. This approach however is technically demanding and does rely on a supervised selection[48]. Both limitations do confine the application of such approach to very selected settings.

Alternative approaches use pathway-specific promoters in order to place the reporter or effector after artificially assembled transcription factor binding sites specific for a given pathway. Thereby specific transcriptional activation can be controlled through the mediation of regulatory elements known to be essential for said pathway.

One example is the BMP response element (BRE) specific for nuclear activity of SMAD1/5/8, which portrays the activation of the BMP pathway. While the BMP response element (BRE) reliably portrays the canonical pathway activation, it misses non-canonical activation and provides a reporter system which is insufficiently sensitive to feedback loops.

Limitations of using pathway-specific promoters include the need to rely on the assumption that the minimal set of regulatory elements used is sufficient to inform on the pathway activation. Furthermore a priori knowledge of such regulatory elements and their extensive characterization and isolation from their natural context is necessary and hamper their application for complex and less characterized cell types.

As a further approach synthetic enhancers or promoters have been proposed by placing the reporter of interest after multiple artificially assembled transcription factor binding sites before a minimal promoter. These methods also rely however on a priori knowledge of transcription factor binding sites known to be relevant for the cell type or developmental stage.

All methods suffer from their dependence on a priori knowledge or accurate discovery and validation of regulatory elements specific for the cell type or stage of interest. Furthermore, since in many cases not all regulatory elements are covered, multiple markers have to be used in order to ensure a reliable cell-type characterization, thereby complicating construction of the reporters and assessment of any experimental outcome.

The characterization of cells based upon the expression of cell-specific surface molecules via flow cytometry has also been described in the art. This is a common practice but limited in the sense that the corresponding markers have to be known in advance and not all cell types possess characteristic surface proteins. Furthermore, in vivo tracing of cell types is not possible or very challenging using such approaches.

Alternative gene expression reporter vectors have been developed in an attempt to employ multiple transcription factor binding sites to regulate expression of a reporter gene.

WO2001/49868 A1 (Korea Research Institute of Bioscience and Biotechnology) discloses a cancer-specific gene expression vector comprising a promoter with a binding site (EF2bs) for the E2F transcription factor expressed in cancerous genes as well as additional binding sites for further transcription factors (e.g. SP1, AP1, NF1 or C/EFB). This approach still however relies on a priori knowledge of TF binding sites (e.g. EF2bs) previously identified as being relevant in specific types of cancer.

WO 2015/110449 A1 (Universiteit Bruxelles/Gent) discloses a computational method for identifying cardiac and skeletal muscle specific regulatory elements with an enrichment of transcription factor binding sites (TFBS), wherein different regulatory regions (CSk-SH1-6; Sk-SH1) of a length of 300-500 bp are disclosed that each contain multiple (3-10) conserved TFBS. This technology focuses however on employing evolutionary conserved TFBSs, thereby relying on genomic conservation of the regulatory sequences, in order to enhance expression in muscle.

WO 2008/107725 A1 discloses a computational method for identifying transcription factor regulatory elements (TFREs) active in a cell of interest, wherein the TFREs have a length of at least 6 to 100 bp, wherein 6 or more TFREs may be combined in a promotor element of an expression vector. This technology employs however the fusion of the same pre-selected minimal promoter, with additional TFREs identified under any given conditions, i.e. the supervised merging of cis-elements with known function.

Guo et al. (Trends in Mol. Medicine, 14:410-418) review several viral vectors as well as transcriptional regulatory elements. Gargiulo et al. (Mechanisms of Development, 35:193-203) disclose the identification of cis-acting elements for a cell-specific expression of a vitelline membrane protein gene 32 (VMPE) in the follicular epithelium of Drospholia, wherein the expression vectors comprise different segments of the regulatory genomic regions.

Despite these advances in the field, such alternative approaches rely on disadvantageous strategies towards generating reporter vectors, such as a dependence on a priori knowledge of relevant promoters, a focus on genetic/evolutionary conservation of TFBSs, or the use of a single promoter which is modified by cis-elements with known function.

There is therefore a need in the field of synthetic reporters for alternative or improved methods and constructs based on non-biased de novo approaches for decoding and reconstructing regulatory information for any given cell type or state.

SUMMARY OF THE INVENTION

In light of the prior art the technical problem underlying the present invention is to provide alternative and/or improved means for the generation of genetic tracing cassettes or vectors based on synthetic cis-regulatory DNA that allow for a cell-type or developmental stage specific expression of reporter genes or functional effectors.

The problem is solved by the features of the independent claims. Preferred embodiments of the present invention are provided by the dependent claims.

The invention therefore relates to a method for generating a cell-type specific expression cassette, comprising the steps of:

a) Providing a gene expression profile of a cell type of interest,
b) Providing genomic sequence data of said cell type of interest,
c) Selecting a set of signature genes from the gene expression profile that are (i) differentially regulated compared to a reference cell type or (ii) selected according to a gene expression level,
d) Identifying genes encoding a transcription factor within the set of signature genes selected in c),
e) Determining a set of genomic regions from the genomic sequence data, wherein each genomic region comprises a sequence encoding a signature gene identified in c) and additional genomic sequence adjacent to and flanking the sequence encoding said signature gene,
f) Identifying multiple genomic sub-regions of comparable and limited size, preferably equal size, within the set of genomic regions determined in e), wherein said genomic sub-regions comprise one or more binding sites for one or more of the transcription factors identified in d),
g) Selecting a minimal set of genomic sub-regions, preferably between 2 and 10, from those determined in f), wherein the set of genomic sub-regions is selected to comprise transcription factor binding sites for a predetermined percentage of all transcription factors identified in d), and
h) Generating a cell-type specific expression cassette comprising the set of genomic sub-regions selected in step g) operably coupled with a reporter or effector gene, wherein the genomic sub-regions are configured to regulate the expression of said reporter or effector gene.

The method allows for the generation of expression cassettes, which when introduced into a cell of interest yield expression of the reporter or effector gene in a manner highly specific to the particular entity or state, such as a cell type or state, which the reporter has been designed to depict, without the need of prior knowledge on the regulation of the gene expression in said entity or state of interest.

In contrast to the prior art, the method and constructs of the present invention are based on non-biased de novo approaches for decoding and reconstructing regulatory information for any given cell-type/state. The invention represents an entirely novel approach based essentially on the clustering of cell-type/state specific TFBSs at cell-type/state specific signature genes. The invention is also characterized by the advantages of employing a quantitative and/or statistical enrichment of relevant TFBS for any given cell-type/state.

In some embodiments the method essentially employs a systems biology approach to generate an expression cassette by identifying a set of endogenously occurring cis-regulatory elements from a given transcriptional signature of the cell type of interest and placing these cis-regulatory before a reporter or effector gene. This approach is independent of pre-conceived information on particular characteristics of the cell type of interest, thereby allowing standardized, unbiased and straightforward production of reporter constructs for any given cell type.

To this end the method identifies genomic sub-regions that comprise transcription factor binding sites characteristic for the cell type and assembles them into a set of genomic sub-regions that comprises a relevant portion of transcriptional regulatory sequence information within the cell type of interest. The set of genomic sub-regions may also be referred to as a "synthetic cis-regulatory DNA", "synthetic regulatory region" or "synthetic locus control region (sLCR)".

When introduced into a cell, the expression of the reporter or effector gene will occur, since in said cell type the transcription factors corresponding to the characteristic transcription factor binding sites are present and initiate expression of the reporter or effector gene. The level of expression is thus related to the particular cell type. Each cell type will essentially yield a different set of genes according to the signature gene set and each cell type will show differing levels of reporter expression depending on the transcription factors present and the combination of regulatory regions assembled in the sLCR.

Advantageously, the method is not limited to certain cell types, but may be applied to virtually any cell type and even distinguish cell state or fate transition within a certain cell type. To this end no a priori knowledge of gene regulation in the cell type of interest is needed.

Instead, the method only relies on the provision of a gene expression profile and genomic sequence data for a given cell type, which can be obtained using standard biomolecular techniques or consulting public databases.

The gene expression profile reflects the levels of gene expression within a cell type of interest. To this end for instance RNA-SEQ or other sequencing or microarray-based techniques can be used to quantify the levels of RNA transcripts with in the cell type of interest. However, the gene expression profile may also be potentially deduced using proteomics, e.g. by quantifying the expressed proteins or peptides present in the cell type of interest, which can be squared to the gene expression profile.

From the gene expression profile, signature genes are selected that are characteristic for the cell type, cell state or entity of interest. The selection of the signature genes can be adapted to the desired application.

For instance, signature genes may be selected according to their gene expression level, by ranking the genes of the cell type of interest according to their gene expression level and selecting genes that are above or below a certain threshold or selecting a predetermined number of highest or lowest expressed genes. For such a selection of signature genes the absolute expression levels of the genes of the cell type of interest serve as a reference. The resulting expression cassette may thereby faithfully report on the presence of the cell type of interest in various assays, independent of the cells to be probed.

However, for certain applications it may be desirable to generate an expression cassette that distinguishes the cell type of interest from a reference cell or a reference cell state with a particular high specificity. For such applications the differentially regulated signature genes are selected by identifying genes that are up- or down-regulated compared to the expression levels in the reference cell type. In these embodiments a gene expression profile of the cell type of interest and a reference cell type is provided. By selecting the differentially regulated genes the expression cassette can be fine-tuned for assays that need to distinguish a cell type (or state or fate) of interest to a certain reference type (or state or fate).

From the selected signatures genes, all genes encoding a transcription factor within the set of signature genes are identified. To this end the method may rely upon publically accessible annotated databases such as ENCODE, mENCODE (the mouse version of the ENCODE project), JASPAR, Ensemble, Entrez Gene, Genebank etc. Thereby a set of transcription factors for the cell type of interest is identified that is characteristically expressed. Transcription factors are identifiable by a skilled person through annotations of function in commonly available databases. Furthermore, the target sequences, ie transcription factor binding sites, for each transcription factor are typically known to a skilled person and/or are obtainable using appropriately annotated databases such as those described above. Preferably, in some embodiments, the method is directed towards the use of transcription factors for which their binding sites (in the form of DNA sequences or sequence motifs) are already known and/or preferably annotated in public databases.

Furthermore, the set of selected genes is used to determine a set of genomic regions from the genomic sequence data of the cell type of interest, wherein each genomic region comprises a sequence encoding a signature gene and additional genomic sequence adjacent to (preferably immediately flanking) the sequence encoding said signature gene. This genomic sequence, e.g. non-coding reference DNA (although cis-regulatory elements may be presented in coding regions), is intended to encompass regulatory sequences, which can be positioned upstream, downstream of, or within coding regions, more often in close proximity to a transcriptional start site but not exclusively there. The size of the additional genomic sequence adjacent to the signature gene may vary as the method is advantageously not overly sensitive to the presence of extra portions of additional genomic sequence.

Thus, the additional genomic sequence should be large enough to encompass cis-regulatory elements (in particular transcription factor binding sites, or enhancers or silencers) that regulate the expression of the signature gene. It is known that such cis-regulatory elements may be in close proximity to the coding region structurally, but—given the 3D structural distribution of the genome in the nucleolus—the cis-regulatory elements may be located at a significant distance in terms of the linear genome sequence. In preferred embodiments, the regulatory genomic sequence is chosen based upon the folded three-dimensional state of the DNA within chromatin in the cell type by using topological associating domains as boundaries. Preferably, in some embodiments, the method assumes cell-type specific non-coding CTCF binding sites as proxy for topological associating domains. CTCF binding sites (in the form of DNA sequences or sequence motifs) are typically known to a skilled person and/or typically annotated in public databases.

In preferred embodiments, after determining the set of genomic regions, the method searches for multiple genomic sub-regions of similar or comparable size (e.g. equal size) that comprise one or more, preferably several, binding sites for the transcription factors that are encoded by the signature genes. All of the genomic sub-regions identified in step f) of the method thus comprise a DNA binding sites for a transcription factor that is characteristically expressed in the cell type of interest. When the genomic sub-region is assembled in a sLCR and said sLCRs is introduced into the cell of interest the characteristically expressed signature transcription factors may bind to said sLCR and regulate the expression of a downstream reporter or effector gene. Typically, a number of genomic sub-regions larger than the ones composing the sLCR are identified, which are redundant in terms of the binding sites for the characteristic transcription factors. An assembly of a limited number of all identified genomic sub-regions is sufficient to represent the overall regulatory complexity and including all elements would not result in increased specificity but rather in unnecessarily large expression cassettes.

The method therefore further encompasses a step to select a minimal set of genomic sub-regions comprising transcription factor binding sites for a predetermined percentage of all transcription factors encoded by the selected signature genes.

By way of example, one can assume within the set of signature genes 100 transcription factors may be identified for which 100 transcription factor binding sites are known. In some embodiments, however, the number of transcription factors encoded by the selected signature genes does not necessarily equal the number of transcription factor binding sites. In some selected embodiments, not all the transcription factors may have known binding sites or multiple transcription factor binding sites matrices may be associated to some transcription factors.

In the quest for the lower possible number of genomic sub-regions to be used in the assembly of a sLCR, e.g. to keep the resulting regulatory sequence compact, the method then preferably ranks the genomic sub-regions according to the number of transcription factor binding sites, in addition to the diversity of the transcription factor binding sites. For instance, the highest ranked genomic sub-region may contain 35 transcription factor binding sites for the transcription factors of step d), wherein 3 of these binding sites are represented 5 times in the same genomic sub-region, while the remaining binding sites are present only once. This highest ranked genomic sub-region would then comprise 23 different (unique) transcription factor binding sites which represent binding sites for 23 transcription factors of the signature genes. This highest ranked genomic sub-region would thus cover 23% of the characteristic transcription factors of step d).

If for instance the predetermined percentage is set to 50%, a second (and potentially third) genomic sub-region(s) would be searched for that encompasses preferably transcription factor binding sites not yet contained within the 23 binding sites of the first genomic sub-region, and so on, such that the further genomic sub-region(s) would comprise at least 7 binding sites for transcription factors not already covered by the first, most highly ranked, genomic sub-region. Typically, a minimal set of 2-10 genomic sub-regions will comprise transcription factor binding sites that are binding targets for at least 50% of the transcription factors encoded by the signature genes.

When the expression cassette is introduced into the cell type of interest, the minimal set of genomic sub-regions act as a synthetic cis-regulatory DNA to which the characteristic transcription factors can bind. The minimal set of genomic sub-regions selected in step g) of the method is therefore herein therefore referred to as a synthetic locus control region (sLCR). In some embodiments, the cassette therefore comprises a regulatory region (sLCR) enriched for regulatory sequences that are bound by transcription factors that are e.g. expressed or highly expressed in the cell type of interest. This regulatory region is therefore unique/tailored to this particular cell type and lead to an expression level of the reporter gene unique to this cell type.

Considering the total amount of characteristic transcription factors identified in d) reflects the regulatory machinery of the cell type of interest, the predetermined percentage of coverage of transcription factors can be regarded as a "percentage of regulatory information" that is covered by the minimal set of genomic sub-regions. Theoretically, the higher the amount of regulatory information covered, the more specific the expression of the reporter or effector gene will be to the cell type. However, advantageously, a percentage covering at least 30% of regulatory information, preferably at least 40% or 50% yields excellent results in terms of a cell-type specific expression profile, as gauged by experimental validation.

In step h) of the method, a cell-type specific expression cassette is generated by assembling the set minimal of genomic sub-regions selected in step g) with a reporter or effector such that they are operably coupled, i.e. that the genomic sub-regions comprising the transcription factor binding sites as cis-regulatory elements are configured to regulate the expression of the reporter or effector gene.

The high coverage of regulatory information by means of the assembled genomic sub-regions without the need of prior information opens a vast potential of application for the methods and constructs described herein. The expression cassettes, as a part of a reporter vector, may be exploited in vitro and in vivo as a reporter for intrinsic cell states, for adaptive responses to external signaling or chemical inputs, cell fate transitions, reprogramming, forward and chemical genetic screenings. Furthermore when the cell-type specific sLCR are combined with endonucleases or suicide genes, the vectors can be used to deplete cell-type, developmental-stage or disease-specific populations in gene therapy or other genetic modification settings. Among these other genetic modification settings, sLCRs may drive the tumor-specific expression of structural components of an oncolytic virus and/or co-stimulatory molecules aiming at increasing the specificity and effectiveness of an oncolytic therapy.

In a preferred embodiment of the invention the method is characterized in that the gene expression profile comprises expression levels of genes in the cell type of interest, and

- according to step c) (i) a gene expression profile of a reference cell type is provided, comprising expression levels of genes in the reference cell type, and differentially regulated signature genes are selected by identifying genes that are up- or down-regulated compared to the expression levels in the reference cell type, preferably selecting genes that are 3- to 10-fold or more upregulated in the cell type of interest, or
- according to step c) (ii) the genes of the cell type of interest are ranked according to their gene expression level and signature genes are selected based on expression of a predetermined level or a predetermined number of signature genes, such as the 100 to 1000 most highly expressed, or 100 to 1000 most lowly expressed genes in the cell type of interest.

The second alternative allows for the selection of signature genes based upon a comparison of the expression level of the genes of said cell type as derivable from the gene expression profile. Such an embodiment is particularly well suited for the generation of expression cassettes that will represent the cell type of interest in different experimental settings. To this end the selection of the genes that are 3- to 10-fold or more upregulated than the average expression level have yielded excellent results.

The first alternative allows for tailoring of the expression cassette to distinguish a cell type of interest compared to a reference cell type. By way of example, the cell type of interest may be a certain tumor cell, while the reference cell type refers to a normal cell of the tissue type typically invaded by the tumor, or by the cell type from which the tumor cell originated.

The reference cell type may however also refer to the same type cell, but in a different cell state or before or after a fate transition. The gene expression profile of the cell type of interest may refer to the gene expression profile of a cancer cell in a mesenchymal state after an epithelial-to-mesenchymal transition (EMT), whereas the gene expression profile of the reference cell type may refer to the gene expression profile of the same type of cancer cell, but in its epithelial state, i.e. before epithelial-to-mesenchymal transition (ETM). In this case the expression cassette will be able to distinguish cells that have undergone EMT from those that did not.

Expression cassettes derivable by selecting the signature genes based upon a relative regulation in comparison to reference cell types are characterized by particularly high specificity allowing for a distinction of the reference cell type from the cell type of interest without the need of any additional marker.

In a preferred embodiment of the invention the method is characterized in that the predetermined percentage of transcription factors covered is 30% or more, preferably 40% or more, most preferably 50%, or more.

In a further preferred embodiment of the invention the method is characterized in that the genomic regions determined in e) correspond to genomic sequences of topological associating domains that contain the differentially regulated gene, wherein preferably a topological associating domain corresponds to a genomic sequence between two CTFC-binding sites.

By selecting the size of the genomic region based upon the topological associating domains an optimal coverage of the potential cis-regulatory elements governing the transcription of said signature genes can be achieved. Within a topological associating domain DNA sequences physically interact with each other more frequently than with sequences outside the topological associating domain, thereby forming a three-dimensional chromosome structures accessible for the transcriptional machinery. Particularly good results could be achieved by selecting genomic sequence between two CTFC-binding sites. Such embodiment yields an optimal balance between computational power resources, specificity of the non-coding cis-regulatory DNA to the genes they are most likely regulating and the size of the flanking DNA to cover the characteristic transcription factor binding sites.

In a preferred embodiment of the method the identification of genomic sub-regions of comparable, e.g. equal, size in step f) is performed by a sliding window algorithm of the genomic regions determined in e), wherein preferably the window has a length of 500 bp to 5000 bp, preferably 700 bp to 2000 bp, more preferably 800 bp to 1200 bp, most preferably 1000 bp and the sliding step has a length of 100 bp to 1000 bp, preferably 120 bp to 300 bp, more preferably 130 bp to 170 bp, most preferably 150 bp. In one embodiment the sliding window is fixed to 1000 bp in size sliding by 150 bp steps, although the genomic sub-regions size resulting out of the scanning may vary in size because it depends on the statistical score and distribution of the TFBS.

It is further preferred that the sliding window algorithm calculates the statistical enrichment of the transcription factor binding sites motifs from a relevant data base (e.g. JASPAR) restricted to the transcription factor bindings sites corresponding to the transcription factors identified in step d). Hereby a list of significant enrichment of characteristic transcription factor binding sites within specific regions is generated and used to identify genomic sub-regions of comparable, preferably equal, size that comprise at least one transcription factor binding site for at least one characteristic transcription factor encoded by a signature gene. Preferably and most likely, tens (10 to 200, preferably between 20 and 180) of TFBS are comprised within genomic sub-regions of comparable size.

According to the present invention, the multiple genomic sub-regions of comparable and limited size, preferably equal size, within the set of genomic regions determined in e) (according to step f), are typically the same size but may vary. Comparable in this context refers to multiple genomic sub-regions that exhibit preferably any window size of 500 bp to 5000 bp.

In a further preferred embodiment of the invention the genomic sub-regions have a length of 100 bp to 1000 bp, preferably 120 bp to 300 bp, more preferably 130 bp to 170 bp, most preferably 150 bp. If a sliding window algorithm is used, the length of the genomic sub-regions will preferably correlate with the sliding step. In other embodiments, the sliding window approach may use any given step size, from 1 bp up to those step sizes indicated for the window sizes above. The preferred length have been determined by employing the method to difference cell types and assay system and reflect the optimal results in terms of expression specificity and total size of the expression cassette.

In a further preferred embodiment of the invention the method is characterized in that the selection of a set of genomic sub-regions in g) is performed by calculating for each genomic sub-region identified in f):

- the enrichment for binding sites of the transcription factors according to d) in the genomic sequence data, and
- a score for the diversity of transcription factors for which binding sites are present,
- wherein the genomic sub-regions are ranked according to the cumulative percentage of transcription factors for which binding sites are present, and
- wherein a minimal set of genomic sub-regions is selected to comprise binding sites for a predetermined percentage of all transcription factors identified in d).

For instance, the number and type of transcription factor binding sites have been generated after identifying genes encoding a transcription factor within the set of signature genes selected in c). Furthermore a list of genomic sub-regions generated in step f) is provided. With this information, one may calculate the number of transcription factor binding sites (TFBS) per genomic sub-region (e.g. TFBS=35) representing the enrichment for binding sites of the transcription factors according to d) in the genomic sequence data. Furthermore it is preferred that the diversity of transcription factor binding sites per genomic sub-region is calculated. For instance, among the 35 TFBS 3 TFBS may be present 5 times, while the remaining TFBS are only present once yielding for said genomic sub-region a number of 35 TFBS with a diversity score of 23.

In a further step the preferred method will rank the genomic sub-regions based upon the highest number of TFBS and the best diversity score. As an example of a number one ranking, in the genomic locus chr10:6019558-6019708, there are 20 TFBS that the said method associated with a Mesenchymal GBM state, with some repeated 2 to 6 times. Once the best ranked genomic sub-region is determined one may calculate the second best in all the remaining genomic sub-regions, wherein TFBS present in the first genomic sub-region are excluded from the ranking. By iteration one may calculate how many different genomic sub-regions are required to cover the entire set of transcription factor binding sites or a predetermined percentage. When a percentage of all regulatory potential (TFBSn× TFBSd) is needed, two independents LCRs may be generated. Typically 4-5 elements are sufficient to reach up to 50% of the regulatory potential, and this was validated as sufficient to generate two independent sLCRs responding to the same signaling (see Examples).

In a further preferred embodiment of the invention, the method is characterized in that the configuration of genomic sub-regions in h) is such that genomic sub-regions comprising a transcription start site are assembled adjacent and upstream of the sequence encoding the reporter gene and the genomic sub-regions not comprising a transcription start site are preferably assembled further upstream from the closest transcription start site. In this case it is particularly preferred that the method may annotate all the genomic sub-regions elements (e.g. 150 bp elements) that contain a natural transcription start site and those which do not and the ranking will start from the transcription start site-containing genomic sub-regions. After the best ranked genomic sub-regions containing a transcriptional starting site is chosen, the ranking of additional genomic sub-region may be performed independent of whether those genomic sub-regions contain a transcription starting site or not.

According to the present invention, in some embodiments, the term “generating a cell-type specific expression cassette” relates to the design and physical production of a nucleic acid molecule. In some embodiments, the term “generating a cell-type specific expression cassette” relates to the design of a cell-type specific expression cassette without physically producing the corresponding nucleic acid molecule, for example the method may be a computer-implemented method or may comprise one or more computer-implemented steps in the method. In some embodiments the method is or comprises computer-implemented elements and produces, as the output of the method, an in silico design, product, simulation and/or computer representation of said construct. The “generating” of a cassette or construct may therefore in some embodiments occur in the computer, ie in computer software, for example the output may be a nucleic acid sequence, nucleic acid sequence information, ie in computer readable format.

The method of the present invention, in some embodiments, may also relate to a computer programme product, such as a software product.

The software may be configured for execution on common computing devices and is configured for carrying out one or more of the steps a) to h) of the method described herein. The computer programme product of the present invention therefore also encompasses and directly relates to the features as described for the method provided herein. Further details on preferred computer-based approaches are provided in the examples and relevant references as described herein. If the method is carried out in a computer programme, for example by way of simulation or computer design of an inventive cassette, the sequence may, in some embodiments, be subsequently synthesized by methods known to a skilled person in a laboratory and utilized in which ever in vitro or in vivo application is desired.

The invention also relates to a system for carrying out the method described herein, comprising one or more computing devices, data storage devices and/or software as system components, wherein said components may be preferably connected in close proximity to one another or via a data connection, for example over the internet, and are configured to interact with one or more of said components and/or to carry out the method described herein. The system may comprise computing devices, data storage devices and/or appropriate software, for example individual software modules, which interact with each other to carry out the method as described herein.

Regarding Computer Implementation:

Step a) regarding providing a gene expression profile of a cell type of interest, may be computer implemented, ie the information for a gene expression profile of a cell type of interest is preferably presented in a computer readable format, configured for processing in the further steps of the method.

Step b) regarding providing genomic sequence data of said cell type of interest, may be computer implemented, ie the information for genomic sequence data is preferably presented in a computer readable format, configured for processing in the further steps of the method.

Step c), regarding selecting a set of signature genes from the gene expression profile, wherein said signature genes are (i) differentially regulated compared to a reference cell type or (ii) selected according to a gene expression level, is preferably computer-implemented. In preferred embodiments genes and their expression profiles are represented as information in a format configured for processing by a computing device, such that a particular group of genes can be selected based on this information. This step may be automated or performed manually, depending on the selection characteristics employed/needed or skills of the user.

Step d), regarding identifying genes encoding a transcription factor within the set of signature genes selected in c), is preferably carried out in a computer implemented method, whereby the genes are annotated with function, such that a transcription factor function can be (optionally) automatically interrogated in any one or more of the identified signature genes. Appropriate databases may be employed, as mentioned by way of example herein.

Step e) regarding determining a set of genomic regions from the genomic sequence data, wherein each genomic region comprises a sequence encoding a signature gene identified in c) and additional genomic sequence adjacent to the sequence encoding said signature gene, is preferably carried out in a computer implemented method. Assessing and selecting genomic sequence adjacent to genes of interest can be carried out by a skilled person based on genomic sequence, ie as available from databases, either by using automatic selection criteria, or by manually assessing and selecting adjacent sequence.

Step f), regarding identifying multiple genomic sub-regions of equal size within the set of genomic regions determined in e), wherein said genomic sub-regions comprise one or more binding sites for one or more of the transcription factors identified in d), is preferably carried out using computer implemented methods. The identification of binding sites for one or more of the transcription factors can be carried out using methods established in the art, for example any given sequence is searched and/or interrogated for the presence of known binding sites, defined by particular sequences or sequence motifs. Software configured for screening sequences for the presence of such known sequences is available to a skilled person.

Step g), regarding selecting a minimal set of genomic sub-regions, preferably between 2 and 10, from those determined in f), wherein the set of genomic sub-regions is selected to comprise transcription factor binding sites for a predetermined percentage of all transcription factors identified in d), is preferably carried out using a (optionally) automated computer algorithm. Details on the determination of genomic sub-regions is provided above. Multiple options are available for software solutions suitable for selecting the desired genomic sub-regions, or the selection can be carried out manually by the skilled user assessing the various sub-regions and compiling them to comprise binding sites for a certain percentage of the relevant transcription factors identified in step d).

Software can be designed and/or configured by a skilled person using established programming, coding, and bioinformatic techniques to assess genomic sub-regions for the presence of transcription factor binding sites, comparison of these binding sites to the transcription factors identified as signature genes, and selecting a compilation of genomic sub-regions to cover a predetermined percentage of the relevant transcription factors.

According to step h) of the method a cell-type specific expression cassette, comprising the set of genomic sub-regions selected in step g) operably coupled with a reporter or effector gene, is generated. As described above, said "generating" may relate to the computer implemented production of nucleic acid sequence information in computer readable form and/or to the synthesis of a physical nucleic acid molecule based on and/or comprising said sequence.

The invention therefore further relates to a method for designing and/or manufacturing a nucleic acid molecule that corresponds, comprises or is based on the product DNA sequence information obtained from steps a) to g). The method preferably comprises comprising carrying out the method described herein and subsequently synthesizing, cloning and/or isolating said nucleic acid molecule.

The term "generating a cassette" may in such embodiments comprise any relevant molecular biological or chemical technique for cloning, mutation, recombination, PCR amplification and/or synthesis used in generating a nucleic acid molecule.

In preferred embodiments the cassette is synthesized using de novo nucleic acid synthesis based on the information obtained by the method of the invention.

In a further preferred embodiment, the invention relates to a cell-type specific reporter vector including an expression cassette generated by a method as described herein.

In a further aspect, the invention relates cell-type specific reporter vector, comprising a synthetic regulatory region comprising 2 to 10 genomic sub-regions of 100 bp to 1000 bp, positioned adjacently, without a linker or with a linker sequence of or less than 100 bp positioned between said sub-regions, wherein said sub-regions originate from separate (non-adjacent) locations in the same genome of a cell type of interest, wherein the sub-regions cumulatively comprise binding sites for at least 5, preferably at least 10, most preferably at least 20 transcription factors, and a reporter or effector gene, wherein the genomic sub-regions are operably coupled with a reporter or effector gene to regulate the expression of said reporter or effector gene.

It is particularly preferred that the genomic sub-regions are selected by a method according to the steps a) to g) as described herein. A person skilled in the art will appreciate that preferred embodiments disclosed for the method equally apply to the cell-type specific reporter vector described herein. The method of the invention leads to structural features of the vector, unique in this field.

A preferred embodiment of the invention relates to the construct design, where transcription factor binding sites from genomic subregions have a length of 100 to 1500 bp or 100 to 1250 bp, preferably 100 to 1000 bp, more preferably 120 bp to 300 bp, more preferably 130 bp to 170 bp, most preferably essentially 150 bp, combined with the origin of the genomic subregions from non-adjacent regions of the same genome. Through this combination, the constructs of the invention are defined by a novel de novo and non-biased construction, by pulling together distinct/separated but highly relevant regulatory regions, that reflect the relevant size of regulatory information, in particular for sizes of preferably 120 bp to 300 bp, more preferably 130 bp to 170 bp, most preferably 150 bp, which approximate the size of a histone particle upon which DNA is wrapped.

A preferred embodiment of the invention relates to the construct design, where 5 or more transcription factor binding sites are used, i.e. the higher numbers of TFBSs reflect a novel de novo and non-biased construction, by pulling together sufficient numbers of TFBSs to cover a large regulatory portion of relevant TFs in any given cell type/state.

The genomic sub-regions are characterized in that they originate from separate locations in the same genome of a cell type and cumulatively comprise binding sites for at least 5, preferably at least 10, most preferably at least 20, or more, transcription factors. In some embodiments, the 2-10 (i.e. 2, 3, 4, 5, 6, 7, 8, 9 or 10) genomic sub-regions are compiled to form a sLCR comprising at least 5, 10, 15, 20, 25, 30, 35, 40, or more, transcription factor binding sites. Thereby the genomic sub-regions cover binding sites for a large amount of transcription factors typically sufficient to cover the regulatory information of a cell type of interest. It is preferred that the binding sites for the transcription factors refer to transcription factors that characteristically expressed in the cell type of interest. To determine transcription factors that are characteristically expressed in the cell type of interest e.g. steps a) through d) of the method described herein may be employed.

Using synthetic regulatory regions comprising 2 to 10 of such genomic sub-regions with a length of 100 bp to 1000 bp have proven an optimal regime in terms of minimizing the size of the vector, while maintaining a high amount of regulatory information as represented by the transcription factor binding sites.

In this regard also the positioning the genomic sub-regions adjacently without a linker or with a linker sequence of less than 100 bp ensures a compact design of the reporter vector and an efficient transduction without comprising on the amount of regulatory information.

In a particular preferred embodiment of the invention the vector is characterized in that each of the genomic sub-regions has a length of 120 bp to 300 bp, more preferably 130 bp to 170 bp, most preferably 150 bp. Such lengths of the genomic sub-regions optimally cover the relevant transcription factor binding sites enriched with statistical significance over the background genomic regions. The optimal size of 150 bp may be due to the fact histones wrap around round 146 base pairs (bp) of the DNA genome around their core particles preventing access to transcription factors. In constrast, nucleosome free regions (NFRs) which are usually associated with active cis-regulatory DNA when upon unwrapping the DNA enables accessibility for transcription factors, which are therefore minimally 146pb. The average size of cis-regulatory DNA is generally inferred by the average size of NFRs—otherwise referred to as DNAseI hypersensitive sites—which is about 1000 bp and usually contains a clustering of relevant transcription factor binding sites on these length scales.

In a further preferred embodiment of the invention the vector is characterized in that the genomic sub-region adjacent to the reporter or effector gene comprises a transcription start site. This ensures that the effector and reporter are in frame and may positively be regulated by the upstream synthetic regulatory region.

The unique design of the invention described herein has the advantage that a variety of reporter or effector genes can be coupled to the synthetic regulatory region comprising the genomic sub-regions depending on the desired application.

In a preferred embodiment of the invention the vector is characterized in that the reporter or effector gene encodes a protein selected from a group comprising a fluorescent protein, a suicide gene, a luciferase, a β-galactosidase, a chloramphenicol acetyltransferase, a surface receptor, a protein tag, including but not limited to 6×His tag, V5 tag, GFP tag, a self-processing ribozyme cassette, a mevalonate kinase and derivates thereof, a biotin ligase and derivates thereof including but not limited to BirA, a engineered peroxidase and derivates thereof including but not limited to APEX2, an endonuclease or site-specific recombinase and derivates thereof, including but not limited to restriction enzymes, Cre, Flp, Tn5, SpCas9, SaCas9, TALENs, a gene correcting a monogenic disease, a viral antigen such as E1A and E1B to induce cell-type specific vaccination, or adjuvant cytockines/chemockines to enhance immune recognition, such as GM-CSF or IL-12.

Fluorescent proteins may be particularly useful for any kind of optical measurement of a signal indicative of the expression of the reporter gene. To this end the method may profit from using the state of the art microscopic and/or fluorescence-activated cell sorting devices and quantification techniques.

Furthermore, the invention can be readily employed using different kind of vector system and easily adapted to the cells of interests.

In a preferred embodiment of the invention the vector is a viral vector, preferably a lentiviral or Adeno-associated viral vector.

In a further preferred embodiment of the invention the vector comprises a nucleic acid sequence according to SEQ ID NO 1-6 or a nucleic acid sequence with an identity of at least 80%, preferably of at least 90%, to any one of SEQ ID NO 1-6.

As described herein the invention allows for the provision of cell-type specific vector construct that mediate a reliable expression of desired reporter or effector genes in the cell type of interest without the need of a prior knowledge. As such the vector construct allow for a variety of different application ranging from basic research to clinical studies or therapeutic strategies.

For instance the vector constructs can be used for the identification of a cell type or the determination of an intrinsic cell state or developmental state of cells. The vectors also allow to study how cells react to external signals or chemicals. Moreover, the vectors can be used in diagnostics, for example to determine the state or type of a cancer, e.g. whether an epithelial or mesenchymal glioblastoma is present and thereby allow for more effective therapeutic guidance. Furthermore, the vectors may also be employed as pharmaceutical agents themselves for instance in gene therapeutic approaches.

In a preferred embodiment the invention relates to the use of a vector for transforming a cell and/or determining a property of a cell, preferably a cell type, state or fate transition, for gene and viral therapy, drug discovery or validation.

The presence of a vector or sLCR as described herein inside an already-transformed cell, is covered in embodiments of the invention.

In one embodiment the invention relates to a method for determining a property of a cell, preferably a cell type, state or fate transition, comprising the steps of a. Providing a cell-type specific reporter vector as described herein,
b. Providing a cell,
c. Transducing the cell with said vector,
d. Measuring a signal indicative of the expression of the reporter or effector gene, wherein the quantity of the signal is instructive for the property of the cell, preferably a cell type, state or fate transition.

Any suitable measurement technique may be employed. For instance the reporter or effector gene may be a fluorescent protein, in which case microscopic devices may be used to quantitatively assess the fluorescent signal and thereby the expression of the reporter or effector gene in the cells probed.

In one embodiment the invention relates to a method for determining an intrinsic cell state, comprising the steps of a. Providing a cell-type specific reporter vector as described herein,
b. Providing cells in which an intrinsic cell state is present or absent, or optionally inducible,
c. Transducing the cells with said vector,
d. Optionally inducing the cells,
e. Measuring a signal indicative of the expression of the reporter gene, wherein the quantity of the signal is instructive of the intrinsic cell state of each of the cells.

In one embodiment the invention relates to a method for determining cell fate transitions, comprising the steps of a. Providing a cell-type specific reporter vector as described herein,
b. Providing cells which undergo a fate transition in response to external signaling and/or chemical perturbations,
c. Transducing the cells with said vector,
d. Exposing the cells to external signaling and/or chemical perturbations,
e. Measuring a signal indicative of the expression of the reporter gene, wherein the quantity of the signal is instructive for the fate transition of the cells.

In one embodiment the invention relates to a method for determining cell fate reprogramming factors, comprising the steps of a. Providing a cell-type specific reporter vector as described herein,
b. Providing cells which undergo a fate transition in response to reprogramming factor, including transcription factors, external signaling and/or chemical perturbations,
c. Transducing the cells with said vector, d. Exposing the cells to transcription factors, external signaling and/or chemical perturbations, e. Measuring a signal indicative of the expression of the reporter gene, wherein the quantity of the signal is instructive for factors introducing fate transition of the cells.

In one embodiment the invention relates to a method for determining the minimal requirements for in vitro cellular propagation of an intended phenotype, comprising the steps of a. Providing a cell-type specific reporter vector as described herein, b. Providing cells which have an intrinsic signature in vivo, c. Transducing the cells with said vector reflecting said signature, d. Exposing the cells to an array of biological and chemicals, e. Measuring a signal indicative of the intended phenotype, wherein the quantity of the signal is instructive of the phenotype.

In one embodiment the invention relates to a method for a targeted correction of diseased cells, comprising the steps of a. Providing a cell-type specific reporter vector as described herein, b. Providing cells which have an intrinsic diseased state which can be corrected by the expression or elimination of a given gene given cell c. Transducing the cells with said vector driving the expression of a gene correcting said disease, or a suicide gene, or an endonuclease d. Exposing the cells to a gene correcting said disease, to a drug activating a suicide gene or an endonuclease e. Measuring a signal indicative of the expression of the reporter gene and a signal indicative of the disease correction In one embodiment the invention relates to a method for Oncolytic viral therapy, comprising a comprising the steps of:

a. Providing a tumor cell-type specific reporter as described herein, b. Providing a vector encoding for an oncolytic viral genome including Adenovirus, Maraba, VSV, HSV-1, Measles, Reovirus, Retrovirus, and Vaccinia virus, which can be modified to transgenically express tumour-associated antigens (TAAs) and/or molecular adjuvants under the expression of tumor sLCRs, c. Generating viral particles with said vector, d. Transducing the target organism with said viral particles to infect tumor cells, e. Measuring viral genetic material within the tumor tissue and not in the surrounding tissues.

The methods described herein, for example those for determining a property of a cell, preferably a cell type, state or fate transition, may be employed in various biological, biotechnological or pharmaceutical (screening) settings.

A further embodiment of the invention relates to using DNA methylation and/or ATAC-seq profiles as an input for signature genes discovery.

ATAC-seq (Assay for Transposase-Accessible Chromatin using sequencing) is a technique used to assess genome-wide chromatin accessibility by probing open chromatin with hyperactive mutant Tn5 transposase that inserts sequencing adapters into open regions of the genome. The mutant Tn5 transposase excises any sufficiently long DNA in a process called tagmentation, whereby the simultaneous fragmentation and tagging of DNA is performed by Tn5 transposase pre-loaded with sequencing adaptors. The tagged DNA fragments are then purified, amplified by PCR and sent for sequencing. Sequencing reads can then be used to infer regions of increased accessibility as well as to map regions of transcription-factor binding sites and nucleosome positions.

The chromatin accessibility of several classes of cis-regulatory elements is a predictive marker of in vivo DNA binding by transcription factors. The repertoire of all accessible sites in chromatin is the strongest predictor of cell identity. Indeed, in cancer, chromatin accessibility is the strongest predictor of cancer type similarity and can be used to identify subtype identities within the common dimensional space of individual cancer types. To investigate whether the acquired heterogeneity depicted by sLCRs is accompanied by changes in genome-wide chromatin accessibility, ATAC-seq can be performed cells sorted according to expression levels of the reporter constructs described herein. Differential analysis of chromatin accessibility can therefore uncover many genes undergoing remodeling. These results described in the examples below highlight the efficacy of sLCRs in revealing e.g. intra-tumoral heterogeneity and enabling in-depth cellular and molecular characterization of tumor models together with primary cancer data.

A further embodiment of the invention relates to target discovery and validation for drug targets in the area of stress responses (e.g. killing cells with high ER stress or inflammatory signaling) and senolitics (e.g. killing senescent cells).

Using the method of the present invention, specific regulatory profiles can be identified for any given cell state, and a reporter construct effectively generated. In some embodiments, a sLCR can be generated for a cell type/state with high ER stress, or inflammatory signaling, or undergoing senescence. Such a reporter can therefore be used to measure whether any given drug candidate, ie.e. applied during a screen, leads to change in the cell state.

A further embodiment of the invention relates to target discovery and validation for drug targets in the area of cell identity/fate changes. As described herein in detail, specific regulatory profiles can be identified for any given cell identity, or for states before and after identity or fate changes, and a reporter constructs effectively generated. In some embodiments, sLCRs can be generated for cell types before and after identity change. Such reporters can therefore be used to measure whether any given drug candidate, ie.e. applied during a screen, leads to change in the cell state.

A further embodiment of the invention relates to target discovery and validation for synthetic peptides, using the methods and constructs described herein.

A further embodiment of the invention relates to target discovery and validation for therapeutic exosomes and antisense oligonucleotides, using the methods and constructs described herein.

A further embodiment of the invention relates to discovery of therapeutic potential of drug candidates in immunotherapy, including but not limited to, the role for innate immune cells in therapeutic response and resistance, and the use of sLCRs to engineer therapeutic adaptive immune cells (T-cells, NK) to resist exhaustion and main target specificity.

In some embodiments sLCRs can be generated as a readout for immune cell activity and/or target specificity, and candidate molecules can be tested and changes in sLCR readout measured in order to assess if immune cells (T-cells, NK) can resist exhaustion when enhanced/treated with a candidate compound.

In a further embodiment the invention relates to a computer-implemented method for determining the sequence of a synthetic locus control region (sLCR), comprising the steps a) to g) of the method as described herein. The invention therefore also relates to computer software products capable and adapted to carry out the method steps a) through g) as described herein as well as a computer program for use in a methods described herein comprising instructions which, when the program is executed by a computer, cause the computer to carry out the steps of a) to g) of the method described herein.

DETAILED DESCRIPTION OF THE INVENTION

The present invention is directed a method for generating cell-type specific expression cassettes, cell-type specific vectors using such an expression cassette as well as application of such vectors. Before the present invention is described with regards to the examples, it is to be understood that the terminology used herein is for the purpose of describing particular embodiments only and is not intended to limit the scope of the present invention.

All cited documents of the patent and non-patent literature are hereby incorporated by reference in their entirety. All terms are to be given their ordinary technical meaning, unless otherwise described herein.

As used herein the term “expression cassette” refers to a nucleic acid construct comprising nucleic acid elements sufficient for the expression of a gene product. The expression cassette also encompasses an electronic representation of an expression cassette, as described herein. Typically, an expression cassette comprises a nucleic acid (sequence) encoding as a gene product a reporter gene or a functional effector operatively linked to the selected genomic sub-regions comprising transcriptional binding sites that act as regulatory elements for the expression of the gene product.

As used herein, the terms “synthetic cis-regulatory DNA”, “synthetic regulatory region” or “synthetic locus control region (sLCR)” refer to an arrangement of multiple genomic sub-regions that comprise validated and/or potential (putative/predicted) cis-regulatory sequences arranged adjacently (with or without a spacer) in a non-naturally occurring order (i.e. not occurring in that order or arrangement in a naturally occurring genome). Examples of cis regulatory sequences are transcription factor binding sites (TFBS), promoters, enhancers, silencers, or other regulatory sequence capable of acting in cis on the expression of a coding region. These regulatory regions, when arranged into a synthetic regulatory region, are typically characteristic for a cell type. The method described herein preferably assembles these regulatory regions into a set of genomic sub-regions that comprises a relevant portion of transcriptional regulatory sequence information within the cell type of interest.

As used herein the term “reporter vector” refers to a nucleic acid construct comprising an expression cassette and further nucleic acid elements that allow for introducing the expression cassette into cells either in vitro or in vivo. The term “reporter vector”, “vector” and “effector vector” may be used interchangeably. A “vector” can have one or more restriction endonuclease recognition sites (whether type I, II or IIs) at which the sequences can be cut in a determinable fashion without loss of an essential biological function of the vector, and into which a nucleic acid fragment can be spliced or inserted in order to bring about its replication and cloning. Vectors can also comprise one or more recombination sites that permit exchange of nucleic acid sequences between two nucleic acid molecules. Vectors can further provide primer sites, e.g., for PCR, transcriptional and/or translational initiation and/or regulation sites, recombinational signals, replicons, selectable markers, etc. A vector can further contain one or more selectable markers suitable for use in the identification of cells transformed with the vector. Vectors known in the art and those commercially available (and variants or derivatives thereof) can be used with the expression cassettes described herein. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics, or can be freely distributed among scientists through Addgene.

As used herein, the term “viral vector” refers to a nucleic acid vector construct that includes at least one element of viral origin and has the capacity to be packaged into a viral vector particle, encodes at least an exogenous nucleic acid. The vector and/or particle can be utilized for the purpose of transferring any nucleic acids into cells either in vitro or in vivo. Numerous forms of viral vectors are known in the art. The term virion is used to refer to a single infective viral particle. “Viral vector”, “viral vector particle” and “viral particle” also refer to a complete virus particle with its DNA or RNA core and protein coat as it exists outside the cell.

The term “transfection” refers preferably to the delivery of DNA into eukaryotic (e.g., mammalian) cells. The term “transformation” refers preferably to delivery of DNA into prokaryotic (e.g., *E. coli*) cells. The term “transduction” refers preferably to infecting cells with viral particles. The nucleic acid molecule can be stably integrated into the genome generally known in the art. The terms “transduction”, “transfection” and “transformation” may however be used interchangeably herein and refer to the process of introducing a vector comprising an expression cassette into a cell.

As used herein the term “cell-type specific” relates to the specificity of the expression of a reporter or effector gene, when an expression cassette as described-herein is introduced into a cell of interest in comparison to other (e.g. reference cells). The term cell-type specific encompasses an expression (level) specific to the cell type of the cell of interest as well as its cell state or fate. The term cell-type specific expression cassette or vector therefore encompasses as well cell-state specific as well as cell-fate specific expression cassette or vectors.

The terms “reporter”, “effector” or “reporter or effector gene”, as used herein, refer to gene products, encoded by a nucleic acid comprised in an expression construct as provided herein, that can be detected by an assay or method known in the art, thus “reporting” expression of the construct and/or “effecting” the state or fate of the cell they are expressed in. Reporters and effectors and nucleic acid sequences encoding reporters are well known in the art. Reporters or effectors include, for example, fluorescent proteins, such as green fluorescent protein (GFP), blue fluorescent protein (BFP), yellow fluorescent protein (YFP), red fluorescent protein (RFP), enhanced fluorescent protein derivatives (e.g. eGFP, eYFP, mVenus, eRFP, mCherry, etc.), enzymes (e.g. enzymes catalyzing a reaction yielding a detectable product, such as luciferases, beta-glucuronidases, chloramphenicol acetyltransferases, aminoglycoside phosphotransferases, aminocyclitol phosphotransferases, or puromycin N-acetyl-tranferases), and surface antigens. Appropriate reporters or effectors will be apparent to those of skill in the related arts. Preferred proteins are selected from a group comprising a fluorescent protein, a suicide gene including but not limited to thymidine kinase, a luciferase, a β-galactosidase, a chloramphenicol acetyltransferase, a surface receptor, a protein tag, including but not limited to 6×His tag, V5 tag, GFP tag, a self-processing ribozyme cassette, a mevalonate kinase and derivates thereof, a biotin ligase and derivates thereof including but not limited to BirA, a engineered peroxidase and derivates thereof including but not limited to APEX2, an endonuclease or site-specific recombinase and derivates thereof, including but not limited to restriction enzymes, Cre, Flp, Tn5, SpCas9, SaCas9, TALENs, a gene correcting a monogenic disease, a tumour-associated antigen or a gene encoding for an immune modulator to facilitate immunotherapy including but not limited to MAGEA3m GM-CSF, IFNγ, IFNβ, CXCL-9-10-11.

The term "gene" means essentially the coding nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Gene expression" as used herein refers to the absolute or relative levels of expression and/or pattern of expression of a gene. The expression of a gene may be measured at the level of DNA, cDNA, RNA, mRNA, proteins or combinations thereof. Gene expression may also be inferred from protein expression.

"Gene expression profile" refers to the levels of expression of multiple different genes measured for a cell type of interest. Gene expression profiles may be measured in a sample, such as samples comprising a variety of cell types, different tissues, different organs, or fluids (e.g., blood, urine, spinal fluid, sweat, saliva or serum) by various methods including but not limited to RNA-SEQ by massively parallel signature sequencing (MPSS), Serial Analysis of Gene Expression (SAGE) technology, microarray technologies, microfluidic technologies, in situ hybridization methods, quantitative and semi-quantitative RT-PCR techniques or mass-spectrometry.

Any methods available in the art for detecting expression of the genes are encompassed herein. By "detecting expression" is intended determining the quantity or presence of an RNA transcript or its expression product e.g. on the protein level.

As used herein, the term "expression level" as applied to a gene refers to the normalized level of a gene product, e.g. the normalized value determined for the RNA expression level of a gene or for the polypeptide expression level of a gene.

The term "gene product" or "expression product" are used herein to refer to the RNA transcription products (transcripts) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc. The term "RNA transcript" as used herein refers to the RNA transcription products of a gene, including, for example, mRNA, an unspliced RNA, a splice variant mRNA, a microRNA, and a fragmented RNA.

Methods for detecting expression of the genes of the invention, that is, gene expression profiling, include methods based on hybridization analysis of polynucleotides, methods based on sequencing of polynucleotides, immunohistochemistry methods, and proteomics-based methods. The methods generally detect expression products (e.g., mRNA) of the genes.

Many expression detection methods use isolated RNA. The starting material is typically total RNA isolated from a biological sample, such as the cell type of interest, and a reference cell type, respectively.

General methods for RNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker (*Lab Invest.* 56:A67, 1987) and De Andres et al. (*Biotechniques* 18:42-44, 1995). In particular, RNA isolation can be performed using a purification kit, a buffer set and protease from commercial manufacturers, such as Qiagen (Valencia, Calif.), according to the manufacturers instructions.

Isolated RNA can be used in hybridization or amplification assays that include, but are not limited to, PCR analyses and probe arrays. One method for the detection of RNA levels involves contacting the isolated RNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 60, 100, 250, or 500 nucleotides in length and sufficient to specifically hybridize under stringent conditions to an intrinsic gene of the present invention, or any derivative DNA or RNA. Hybridization of an mRNA with the probe indicates that the intrinsic gene in question is being expressed.

An alternative the level of gene expression in a cell type of interest involves the process of nucleic acid amplification, for example, by RT-PCR (U.S. Pat. No. 4,683,202), ligase chain reaction (Barany, *Proc. Natl. Acad. Sci. USA* 88:189-93, 1991), self sustained sequence replication (Guatelli et al., *Proc. Natl. Acad. Sci. USA* 87:1874-78, 1990), transcriptional amplification system (Kwoh et al., *Proc. Natl. Acad. Sci. USA* 86:1173-77, 1989), Q-Beta Replicase (Lizardi et al., *Bio/Technology* 6:1197, 1988), rolling circle replication (U.S. Pat. No. 5,854,033), or any other nucleic acid amplification method, followed by the detection of the amplified molecules using techniques well known to those of skill in the art. These detection schemes are especially useful for the detection of nucleic acid molecules if such molecules are present in very low numbers.

In particular, gene expression may be assessed by quantitative RT-PCR. Numerous different PCR or QPCR protocols are known in the art. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR. However, preferred are cyclers with real-time fluorescence measurement capabilities.

Quantitative PCR (QPCR) (also referred as real-time PCR) is preferred under some circumstances because it provides not only a quantitative measurement, but also reduced time and contamination. As used herein, "quantitative PCR (or "real time QPCR") refers to the direct monitoring of the progress of PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time.

Furthermore microarrays may be used for gene expression profiling. By "microarray" is intended an ordered arrangement of hybridizable array elements, such as, for example, polynucleotide probes, on a substrate. The term "probe" refers to any molecule that is capable of selectively binding to a specifically intended target biomolecule, for example, a nucleotide transcript or a protein encoded by or corresponding to an intrinsic gene. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, for example, U.S. Pat. Nos. 6,040, 138, 5,800,992 and 6,020,135, 6,033,860, and 6,344,316. High-density oligonucleotide arrays are particularly useful for determining the gene expression profile for a large number of RNAs in a sample.

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains Sufficient information to uniquely identify transcript, provided that the tag is obtained from a unique position within each transcript. Then, many transcripts are linked together to form long serial molecules, that can besequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484-487 (1995); and Velculescu et al., Cell 88:243-51 (1997).

Nucleic acid sequencing technologies are suitable methods for analysis of gene expression. The principle underlying these methods is that the number of times a cDNA sequence is detected in a sample is directly related to the relative expression of the mRNA corresponding to that sequence.

These methods are sometimes referred to by the term Digital Gene Expression (DGE) to reflect the discrete numeric property of the resulting data. Early methods applying this principle were Serial Analysis of Gene Expression (SAGE) and Massively Parallel Signature Sequencing (MPSS). See, e.g., S. Brenner, et al., Nature Biotechnology 18(6):630-634 (2000).

The advent of "next generation" sequencing technologies has made DGE simpler, higher throughput, and more affordable. As a result, more laboratories are able to utilize DGE to screen the expression of more genes in more cell types of interest than previ ously possible. See, e.g., J. Marioni, Genome Research 18(9): 1509-1517 (2008); R. Morin, Genome Research 18(4):610 621 (2008); A. Mortazavi, Nature Methods 5(7):621-628 (2008): N. Cloonan, Nature Methods 5(7):613-619 (2008).

Next generation sequencing typically allows much higher throughput than the traditional Sanger approach. See Schuster, Next-generation sequencing transforms today's biology, *Nature Methods* 5:16-18 (2008); Metzker, Sequencing technologies the next generation. Nat Rev Genet. 2010 January; 11(1):31-46. These platforms can allow sequencing of clonally expanded or non-amplified single molecules of nucleic acid fragments. Certain platforms involve, for example, sequencing by ligation of dyemodified probes (including cyclic ligation and cleavage), pyrosequencing, and single-molecule sequencing. Nucleotide sequence species, amplification nucleic acid species and detectable products generated there from can be analyzed by such sequence analysis platforms. Next-generation sequencing can be used in the methods of the invention, e.g. to determine the gene expression profile or the genomic sequence data of the cell type of interest.

RNA Sequencing (RNA-Seq) uses massively parallel sequencing to allow for example transcriptome analyses of genomes at typically a far higher resolution than is available with Sanger sequencing- and microarray-based methods. In the RNA-Seq method, complementary DNAs (cDNAs) generated from the RNA of interest are directly sequenced using next-generation sequencing technologies. RNA-Seq has been used successfully to precisely quantify transcript levels, confirm or revise previously annotated 5' and 3' ends of genes, and map exon/intron boundaries (Eminaga et al., 201 3. Quantification of microRNA Expression with Next-Generation Sequencing. Current Protocols in Molecular Biology. 103:4.1 7.1-4.1 7.14).

As used herein, "sequencing" thus refers to any technique known in the art that allows the identification of consecutive nucleotides of at least part of a nucleic acid. Exemplary sequencing techniques include Illumina™ sequencing, direct sequencing, random shotgun sequencing, Sanger dideoxy termination sequencing, whole-genome sequencing, massively parallel signature sequencing (MPSS), RNA-seq (also known as whole transcriptome sequencing), sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, Illumina Hiseq4000, Illumina NextSeq500, Illumina MiSeq and Miniseq, MS-PET sequencing, mass spectrometry, and a combination thereof.

Gene expression profiles may also be deduced from information on the proteome. The term "proteome" is defined herein as the totality of the proteins present in a cell type at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics.

The term "genome," as used herein, generally refers to the complete set of genetic information in the form of one or more nucleic acid sequences, including text or in silico representations thereof. A genome may include either DNA or RNA, depending upon its organism of origin. Most organisms have DNA genomes while some viruses have RNA genomes. As used herein, the term "genome" need not comprise the complete set of genetic information. The term may also refer to at least a majority portion of a genome such as at least 50% to 100% of an entire genome or any whole or fractional percentage therebetween.

The term "genomic sequence data" refers to data, including text or in silico representations thereof, on a genome, wherein the genomic sequence data may also relate to a genome preferably the majority of the genome, such as at least 50% to 100% of an entire genome or any whole or fractional percentage therebetween.

The provision of genomic sequence data of may include the actual sequencing of the genome of a cell type of interest or the reliance upon publically available data bases on genome sequence data such as the annotated Genome Sequence DataBase (GSDB), operated by the National Center for Genome Resources (NCGR). The provision of genomic sequence data for a large number of species is publicly available through The UCSC Genome Browser created by the UCSC Genome Browser Group of UC Santa Cruz (CA, USA).

The term "genomic region" as used herein, generally refers to a region a genome. Typically a genomic region refers to a continuous nucleic acid sequence stretch of the genome of the cell type of interest comprising at least one gene.

The term "genomic sub-region" refers to a portion of the a genomic region that is identified as described herein to comprise one or more binding sites for one or more of the transcription factors that have been identified as signature genes based upon the gene expression profile(s).

The term "nucleic acid" refers to any nucleic acid molecule, including, without limitation, DNA, RNA and hybrids or modified variants and polymers ("polynucleotides") thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). Nucleotides are indicated by their bases by the following standard abbreviations: adenine (A), cytosine (C), thymine (T), and guanine (G).

An "exogenous nucleic acid" or "exogenous genetic element" relates to any nucleic acid introduced into the cell, which is not a component of the cells "original" or "natural" genome. Exogenous nucleic acids may be integrated or non-integrated, or relate to stably transfected nucleic acids.

"Functional variants" or "functional analogs" preferably refers to a nucleic acid or protein having a nucleotide sequence or amino acid sequence, respectively, that is "identical," "essentially identical," "substantially identical," "homologous" or "similar" to a reference sequence which can, by way of non-limiting example, be the sequence of an isolated nucleic acid or protein, or a consensus sequence derived by comparison of two or more related nucleic acids or proteins, or a group of isoforms of a given nucleic acid or protein. Non-limiting examples of types of isoforms include isoforms of differing molecular weight that result from, e.g., alternate RNA splicing or proteolytic cleavage; and isoforms having different post-translational modifications, such as glycosylation; and the likes.

As used herein, the term "variants" or "analogs" refers to a nucleic acid or polypeptide differing from a reference nucleic acid or polypeptide, but retaining essential properties thereof. Generally, variants are overall closely similar, and, in many regions, identical to the reference nucleic acid or polypeptide. Thus "variant" forms of a transcription factor are overall closely similar, and capable of binding DNA and activate gene transcription.

As used herein, the term "sense strand" refers to the DNA strand of a gene that is translated or translatable into protein. When a gene is oriented in the "sense direction" with respect to the promoter in a nucleic acid sequence, the "sense strand" is located at the 5' end downstream of the promoter, with the first codon of the protein is proximal to the promoter and the last codon is distal from the promoter. The opposite is referred to as the "anti-sense" strand.

As used herein, the term "operably linked" refers to that the regulatory elements in the nucleic acid construct are configured to enable functional coupling between the regulatory element and gene, leading to expression of the gene, ie the regulatory element is preferably in-frame with a nucleic acid coding for a protein or peptide.

As used herein the term "comprising" or "comprises" is used in reference to expression cassettes, reporter vectors, and respective component(s) thereof, that are open to the inclusion of unspecified elements.

The term "consisting of" refers to expression cassettes, reporter vectors, and respective component(s) thereof as described herein, which are exclusive of any element not recited in that description of the embodiment.

The term "signature genes" relates to genes that are selected from the genes of the cell type of interest genes that are characteristic for the expression profiles of said cell type of interest. Differentially regulated signature genes may be e.g. selected by identifying genes that are up- or down-regulated compared to the expression levels in the reference cell type, or by ranking the gene expression level for the cell type of interest and selecting signature genes based upon a threshold level or predetermined number of genes (e.g. most highly or most lowly expressed).

As used herein the term "transcription factor" refers to a protein that binds to specific DNA sequences and thereby controls the transfer (or transcription) of genetic information from DNA to mRNA. The function of transcription factors is primarily to regulate the expression of genes. Transcription factors may function alone or in combination with further proteins in a complex, by promoting (as an activator), or blocking (as a repressor) the recruitment of RNA polymerase to specific genes. Transcription factors contain at least DNA-binding domain, which attaches to a specific sequence of DNA ("binding sites") typically adjacent to the genes that they regulate.

The term "microscopic device" relates to a device that comprises means for microscopic analysis of cells. Microscopic analysis can be carried out, without limitation, by a light microscope, binocular stereoscopic microscope, bright field microscope, polarizing microscope, phase contrast microscope, differential interference contrast microscope, automatic microscope, fluorescence microscope, confocal microscope, total internal reflection fluorescence microscope, laser microscope (laser scanning confocal microscope), multiphoton excitation microscope, structured illumination microscope, transmission electron microscope (TEM), scanning electron microscope (SEM), atomic force microscope (AFM), scanning near-field optical microscope (SNOM), X-ray microscope, ultrasonic microscope. Microscopic devices can additionally comprise a camera and/or detector for recording pictures of cells, for example, and a computer system for controlling the microscopic device.

The presence and/or intensity of a signal produced by reporter gene can be determined by means of a microscopic device, but also by other devices that can detect signals generated by reporter genes without limitation, such as flow cytometers, luminometers, spectrometers, photometers, or colorimeters.

As used herein the term "topological associating domains" preferably refers to a self-interacting genomic region, meaning that DNA sequences within a topological associating domain physically interact with each other more frequently than with sequences outside the topological associating domain, thereby forming a three-dimensional chromosome structures. Topological associating domains can range in size from thousands to millions of DNA bases. A number of proteins are known to be associated with topological associating domains formation including the protein CTCF and the protein complex cohesin. In preferred embodiments the topological associating domains refers to a genomic sequence between two CTFC or cohesin binding sites.

As used herein, the term "generating a cell-type specific expression cassette" relates in some embodiments to the design of a cell-type specific expression cassette without physically producing the corresponding nucleic acid molecule, for example the method may be a computer-implemented method or may comprise one or more computer-implemented steps in the method.

As used herein, the term "generating a cell-type specific expression cassette" relates in some embodiments to the design and physical production of a nucleic acid molecule, preferably by de novo synthesis of the nucleic acid molecule.

Artificial gene synthesis (or de novo synthesis) is a preferred method of generating a cassette of the present invention and relates to methods used in synthetic biology to create any given nucleic acid sequence. In some cases based on solid-phase DNA synthesis, artificial synthesis differs from molecular cloning and polymerase chain reaction (PCR) in that the user does not have to begin with pre-existing DNA sequences. Therefore, it is possible to make a completely synthetic double-stranded DNA molecule with no major limits on either nucleotide sequence or size. Gene synthesis approaches may be based on a combination of organic chemistry and molecular biological techniques and entire genes may be synthesized "de novo", without the need for precursor template DNA. The method has been used to generate functional bacterial chromosomes containing approximately one million base pairs. Gene synthesis has become an important tool in many fields of recombinant DNA technology including heterologous gene expression, vaccine development, gene therapy, vector construction and various forms of molecular engineering. The synthesis of nucleic acid sequences is often more economical than classical cloning and mutagenesis procedures. Multiple techniques are well-established and known to a skilled person.

The term "gene therapy" preferably refers to the transfer of DNA into a subject in order to treat a disease. The person skilled in the art knows strategies to perform gene therapy using gene therapy vectors. Such gene therapy vectors are optimized to deliver foreign DNA into the host cells of the subject. In a preferred embodiment the gene therapy vectors may be a viral vector. Viruses have naturally developed strategies to incorporate DNA in to the genome of host cells and may therefore be advantageously used. Preferred viral gene therapy vectors may include but are not limited to retroviral vectors such as moloney murine leukemia virus (MMLV), adenoviral vectors, lentiviral, adenovirus-associated viral (AAV) vectors, pox virus vectors, herpes simplex virus vectors or human immunodeficiency virus vectors (HIV-1). However also non-viral vectors may be preferably used for the gene therapy such as plasmid DNA expression vectors driven by eukaryotic promoters or plasmid DNA sequence containing homology to the host genome in order to directly integrate the expression cassette at preferred locations in the genome of interest. DNA transfer may also be carried out using liposomes or similar extra-cellular vescicles. Furthermore preferred gene therapy vectors may also refer to methods to transfer of the DNA such as electroporation or direct injection of nucleic acids into the subject. The person skilled in the art knows how to choose preferred gene therapy vectors according the need of application as well as the methods on how to implement nucleic acid constructs such as the expression cassettes described herein into the gene therapy vector. (P. Seth et al., 2005, N. Koostra et, al. 2009., W. Walther et al. 2000, Waehler et al. 2007).

The method, system, or other computer implemented aspects of the invention may in some embodiments comprise and/or employ one or more conventional computing devices having a processor, an input device such as a keyboard or mouse, memory such as a hard drive and volatile or non-volatile memory, and computer code (software) for the functioning of the invention.

The system may comprise one or more conventional computing devices that are pre-loaded with the required computer code or software, or it may comprise custom-designed software and/or hardware. The system may comprise multiple computing devices which perform the steps of the invention. In certain embodiments, a plurality of clients such as desktop, laptop, or tablet computers can be connected to a server such that, for example, multiple users can provide data or perform calculations at different steps of the method. The computer system may also be networked with other computers or necessary databases, such as genomic databases, over a local area network (LAN) connection or via an Internet connection. The system may also comprise a backup system which retains a copy of the data obtained by the invention. The data connections necessary between the various steps of the method may be conducted or configured via any suitable means for data transmission, such as over a local area network (LAN) connection or via an Internet connection, either wired or wireless.

A client or user computer can have its own processor, input means such as a keyboard, mouse, or touchscreen, and memory, or it may be a terminal which does not have its own independent processing capabilities, but relies on the computational resources of another computer, such as a server, to which it is connected or networked. Depending on the particular implementation of the invention, a client system can contain the necessary computer code to assume control of the system if such a need arises. In one embodiment, the client system is a tablet or laptop.

The components of the computer system for carrying out the method may be conventional, although the system may be custom-configured for each particular implementation. The computer implemented method steps or system may run on any particular architecture, for example, personal/microcomputer, minicomputer, or mainframe systems. Exemplary operating systems include Apple Mac OS X and iOS, Microsoft Windows, and UNIX/Linux; SPARC, POWER and Itanium-based systems; and z/Architecture. The computer code to perform the invention may be written in any programming language or model-based development environment, such as but not limited to C/C++, C#, Objective-C, Java, Basic/VisualBasic, MATLAB, R, Simulink, StateFlow, Lab View, or assembler. The computer code may comprise subroutines which are written in a proprietary computer language which is specific to the manufacturer of a circuit board, controller, or other computer hardware component used in conjunction with the invention.

The information processed and/or produced by the method, ie as digital representations of nucleic acid sequences, gene expression profiles, lists of genes and/or particular sequence elements such as TF binding sites, can employ any kind of file format which is used in the industry. For example, the digital representations can be stored in a proprietary format, DXF format, XML format, or other format for use by the invention. Any suitable computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, cloud storage or a magnetic storage device.

In Table 1 the nucleotide sequence of preferred embodiments of minimal sets of genomic subregions for a cell-type specific reporter vector (i.e. synthetic locus regions) are listed

TABLE 1

Nucleotide sequences of preferred synthetic locus regions for cell-type specific reporters:

| | |
|---|---|
| SEQ ID NO 1:<br>MGT#1:<br>subtype-specific sLCR for mesenchymal glioblastoma (MES-GBM) generated using the method described herein (see Example 1).<br>MGT#1 is validated for use in several other solid tumors as reported for Epithelial/Mesenchymal fate transition, including lung and breast cancer. | ATATTTATTTTTAGGACCAGAAAGTTAAAGTGAATTGGATTTGATC<br>CATTTTCTGAAAGGCTGGCAAGAATTCTTGACATTGCACAGGAATT<br>TCCATGTCAGCATGTTCTCACATGTATGATCTAATTTAGAGATTAT<br>TTTGGGGGGCGGGGGTTGAGGAAATGGCATGACTCAGAGTTTAAAA<br>GCCCCAAATCTTAGCTGTGCCTGTGTAGCTTTACCACATAACCCAT<br>TGATAACTTAGTTGTGCAACCATCACCACCATCTGTTTTCAGAACT<br>CTTTTCATTTTGCGAAACTGAAACCCGTTAAGCACTGATTTCCCAC<br>TCTCCCTCCTCCCAGCCCATAGCAAACCACCATCCCACCAGCACTT<br>TCATTTCGCAAATGGCAAAACTGAAGCCGATATTGTGGTTGTGACT<br>TATCCCAAAGTAATATACACATAAACCTCTATGGATGAGGAAAAAG<br>ACAGAGGGAAACTAAAAATTCAAAAGAACAAATTTGACTCACAGAT<br>TTGCTGACTCATAGTTGTGACACTTCCTGGCTCAGGAAGTTGAATT<br>TCATTAAGCCTTTGTGGTTTGGGGCTCTGCTGTGCTTTGACAGCTC<br>TGATCTCCTCCCTTCCGGCTGGGCTGTCTGGGGCGCTCTAAATGAG<br>TGTTGATTTAATGCACTGCCTTCGCACCCGTGCTGGTGCGTCCCGG<br>GGACAGGGGTGGCTGTGCGGTGCCGCGGCGGCCGGCGGGGCTCCTT<br>CCCCAGCAGGGGTGGGGACGCTGAGTCACGGATCTGTCACCGCTTT<br>GCACCTCTCCGAGCCCTCGGGGGCCAAAGCAAAAGCGAAAGCGA |
| SEQ ID NO 2:<br>MGT#2<br>subtype-specific sLCR for mesenchymal glioblastoma (MES-GBM) generated using the method described herein (see Example 1) | CTAGAACAGCAGGGCCACCTCCTTCTCTCCCCCGCGGGCATGGGCC<br>CCCACCCCCACTGCCGGCAGAGTGCTGAGGACTCGTGCACCATGAG<br>AACTTCTGACCATGAGAACTTTGACTTCCGGATTTGGGGGATCTGC<br>CCAGGTGAACACAATGCAAGGGGCTGCATGACCTACCAGGACAGAA<br>CTTTCCCCAATTACAGGGTGACTCACAGCCGCATTGGTGACTCACT<br>TCAATGTGTCATTTCCGGCTGCTGTGTGTGAGCAGTGGACACGTGA<br>GGGGGGGGTGGGTGAGAGAGACAGGCCACATTGTGCAACAGATCTC<br>TAGAGCTTTTTCATCTTGCAAAACTGAAACTGTATACCCATGGAAC<br>AACAGCTCCCTGCTCCCCTCCCCCTCAGCTCCTGGGTAGTGACATT<br>TCTTGATTCTCAGTAAACTATCACAAGAACAAAAAACCAAACACCG<br>CATATTCTCACTCATAGGTGGGAATTGAACAATGAGATCACATGGA<br>CACAGGAAGGGGAATATCACACTCTGGGGACTGTGGTGGGGTGGGG<br>GGAGTGGGGAGGGATAGCACTGGGATGTCCCAAGAGAAGGGGAAGA<br>GGGGGAGGTGTTAGAGAACTTGTGTGTTCAACCGAAACATGATGAA<br>AACAGGGAAAGCCCCCAAGATACCTGTCATTCCCGATGATGTCAGA<br>TTCAGCAAATTCAATGATAACAAAACATTATGAAAAAATTAGTAAT<br>TAAAATAATACAGCAATGTGTATGAACAAAATAATCAATGAAAGTG |

TABLE 1-continued

| Nucleotide sequences of preferred synthetic locus regions for cell-type specific reporters: | |
|---|---|
| | AAACCTAATAGTAATTCCACAAACTTATTACAAAGCTATTAATTTA<br>AAGAGTAGTGGCAATTGAAAACCACAACCAACACCAGTGCTTACAG<br>CAGCAATACTTTTACTCAGACTTCCTGTTTCTGGAACTTGCCTTCT<br>TTTTTGCTGTGTTTATACTTCCCTTGTCTGTGGTTAGATAAGTATA<br>AAGCCCTAGATCTAAGCTTCTCTGTCTTCCTCCCTCCCTCCCTTCC<br>TCT |
| SEQ ID NO 3:<br>PNGT#1:<br>subtype-specific sLCR for proneural glioblastoma (PN-GBM) generated using the method described herein (see Example 1) | AGAGCTCCTGGCCAAGGTCTTTGTGTTCAGACCAGAAGAGGAAGGA<br>GGGCTCCCTCCCCCTGGGGCTGTGGAGGCTGAGGCTCCTGGGGGGT<br>TGTCCACATCTGGACCGTGGAGCTGTTGGGGGGAATGGGGGCAGG<br>TGGAGAAGAGGATAAGCAGCTGATTGGGCCCAGACTACTCTGGGCT<br>GGCTCCATCTTACATGACTGCCACAAACAGCTGCAGGAGTGTGACA<br>GATCACAACACTAGCATTGTACCTCAAAATATGCTTGTACCCTAAG<br>GCACAAGAACTGGTTTGACTTACAACCGCAGCCCCCGTCCGGGCAC<br>CCCGAGGCCCGCGGGAGCCACCCTCGAACCCCGGCCGCGCACGGGC<br>GGGGCGGGCGCGCACCTGCCGGGAGCCCGTGTTTGTAAACAAACCG<br>CGCGCCTAATTAGCCTGGCGGGAGCGCGCGCGGGGCGGGGGGCG<br>GGGCGTCGGTGCGCGCGGGCAGGTCGGCCCCGCCCGGGGAGGAGCC<br>GCGCTCTGCCGCGCCCTCCGTGTCACCATCTCCCCCACCCGACTTG<br>GCGGGGCGCGGGCTTGCTGGAGCCTGCGGGACCCAGAGCCCGCTCC<br>GGAGCCAGCCCTGGGAGTGGCCAGCTTGAACCCGAGGGCCCCGCAG<br>ACCGTTACTCCGGCCCCCGCCCGGGGCGGGGCGCGCGGGGGCGCGG<br>CGCAGCCCAACCCGCACAGCCGCGTCCCCAAACACCACCGAGGAGG<br>GAAAACAGACGGAGAGGGGTGGGGCTGCGGGCGGGGCCGGCGCCTA<br>ATTGGGCCGCGGGCGCCTCGAGGTGGGCGGGGCATAAGGGGGCGGG<br>GCCGCGGAGACCCCGGGCGGGAGCAGGGAGAGGAAAGAAGAGACTG<br>AGTACGCGGAGACCGAGATTCGGAAATATTTCTGCCTTAATTGTTC<br>TTCCATTGTCTTTCTCCTGTGGGTCCCCTCTCACCTTTCTGTATGG<br>TCCTGGATCACCCCCCGAGGCTTTGTCTCCCCCATCCACGGGCTTA<br>TTCTCTCGGCACCCCCTTCCTCTCCCGTCATCGGTTGAT |
| SEQ ID NO 4<br>PNGT#2:<br>subtype-specific sLCR for proneural glioblastoma (PN-GBM) generated using the method described herein (see Example 1) | TTAATTAATCCCTCCTCTAATCCCTCCAGCGGGATCAGGGAGGAGG<br>TGCGGGACCTGCTGCCCCGGGCTTGCCCCCATCCCGGCCTCACGCA<br>TGGGCGCCTGTCTCAGCCCTCTCCCAGGACGCTGCAGGTGTGGCTG<br>GGCCAGCGCTAATTAGTGGGCCGCGCGGGGGCCCCGCTGAGCCTTT<br>GACAGAAAAGGCGGTAGGGAGGTGGGGGCAGGGAGGCGCTCCACCA<br>GCCAGAAGTCCGGAGCGCAACCCAAAGTACTCCATCTCAAAAGAAA<br>AAAGGCGGGGGCGGTGGGGGGGGGGGTGATTTCAGTACAAAGCCT<br>ACAGACATTATAAAAATATTAAGATTTTTGTTCGTTTGTTTTTTGT<br>TTTTGAGACAGAGTCTCACTGTCACCCCCAGGCTGGAGTCTGTGCC<br>GGCGCCCGCTGCTTCGCATCTGCGCGCCCGCCCGGTGCCGGGCCCC<br>GCCCTCCGCCTCAGCCCCAAGCTCGGCCCGCGGGCCCGGCCACAGG<br>TGCCCCGGCGGCCCCGCCTGGCCCGAGGGAAGAGGGCAGCTGGGAG<br>GGGCCCATGAGAGAACCAAAACTGTGCCCCCAGGCTTGGAAAGAAA<br>TCACATGTATGGCCAGCAGGAAGGTTCCGGAAGGTTCCGGAGGACA<br>CCTGCAGGTGGGACTGAGAACAGGGGTCTCGGCTGGGAGTGGCTGA<br>GGCCATATGAGGACCTCGACTGCCACAAACAGCTGCAGGAGTGTGA<br>CAGATCACAACACTAGCATTGTACCTCAAAATATGCTTGTACCCTA<br>AGGCACAAGAACTGGTTTGACTTACAAAACTGATCTCAGAGTTGGG<br>ATCAAAGTTTTTCTACCACTCTACTATGAGCCCTCGGCCGGGCCCC<br>GCCCCGCCAGCTCCGCGCGGCTCTGGGCTCTCTAGGGGTGGGGCTG<br>CGGGCGGGGCCGGCGCCTAATTGGGCCGCGGGCGCCTCGAGGTGGG<br>CGGGGCATAAGGGGGCGGGGCCGCGGAGACCCCGGGCGGGAGTTTT<br>TTTCTGCAAGCGAGAGGGGGGGTGTTGTTGGTATCGCCCCCTCCTT<br>CTCCTCCCCCCAGGGGTGAAAGTGCAAGAGGAAGTGCAGCCGCTGC<br>CATCTTTCCTCCGCTCCGAACACACGGAGCCCGGGGCCGCACAGCC<br>GCCGCTCCTGTACA |
| SEQ ID NO 5<br>CLGT#1<br>subtype-specific sLCR for classic glioblastoma (CL-GBM) generated using the method described herein (see Example 1) | ATGGTCTCAATCTCCTGACCTTGTGATCCGCCCACCTCGGCCTCCC<br>AAAGTGCTGGGATTACAGGTGTGAGCCACCACGCCCAGCCGACAGT<br>CCCTTATCTGGTTCATCTTCGTACCTCTAAAAGTCAGCATGGATGC<br>TCTATTAATGATATATTTATACATATTAGCAACAAACAATTGGAAA<br>CTAAAACTTTAAAAAGACATTCTCACACCTGTAATCCCAGCATGTT<br>GGGAGGTCGAGGCAGGCGAATCACGAGGTCAGGAGTTCGAGACCAG<br>CCTGGCCAACATGGTGAAACTCTGGAAGACCGAAACTATTCAGCAA<br>GAACTAAGAACCACAATGTTAAGGGGGTCCATTGTTTATTTTTTTT<br>TCTTTAGAGGATGAAAACCAAAGGTCAGGTGATTTAATTTAAAATT<br>AACACTCTTATTTTTTGCCCGCCCGCCTGCCTGCCTCTTTACAATT<br>TACAGAATGTCTTAAGGTAGTTAAGTTTCAAGTTTTTCTTTCTCAG<br>TATCCTACCTTCATGCATCAAAGTGGGTGGCCTTTATCCCATTAAC<br>GGCAATTACGTAAGACAGATGTCCCTAGATGAAATCTTACAGTTCT<br>TTTAGTCAGACCCCCCACCCCGCCACCGCCACCAGACACCACCATC<br>GCTGTGTAGTGTGGGTTTTTATTCGTGTTCGTGTGTGTGTGTGGAC<br>ACATTTTCCTTTTCGGTTGCTCTGTCCTTTGGTTCGTGCTCGCCTC<br>GCTTTTTCCACACTCCTGCTCTCTGGCTCTCTGTGTCTCTCGCTCT<br>TTCGAAAATTTTCCTAAGTCCGGGCGCGCGCTCCCTCCCCTTCCGC<br>CCACCCCAGCCCCTCGGCGGCGCCCGCGGGAGGGGGAGGAGGCCTC |

TABLE 1-continued

| Nucleotide sequences of preferred synthetic locus regions for cell-type specific reporters: | |
|---|---|
| | GGGGGCGCCGGGCGACGCGGTCCGGGGGGTGGAGCGTTGGCGTCGT GCGAGGGGTCGTCACTGGCGCGGAGACGCCCCCTCTCCCCCCTCGG CTCAGCCGGGCTGCTGCCCGAGCCCGGGGGGTGGGGGGCGTCTCCC CGGCCCGTCCCGTCCCCGGCCGGGCGCGGGCGGAGGGACCCCCTCC CCGGGCTCCCGGGGGGCCGCCTCCCTCCGCCGGCTCCCGCCCTCCC AGCCGC |
| SEQ ID NO 6 CLGT#2 subtype-specific sLCR for classic glioblastoma (PN-GBM) generated using the method described herein (see Example 1) | TTAATTAAGAATATCTGGCTGGCCACGTGTTTGTAAAGAAAAACCA AGACGGCCAGGCGAGGTGGCTCACACCTGTAATCCCAGCACTTTGG GAGGCCGAGGCGGGCGCTGCCCTTCGGCCTTCAAGGAGGAATTCCT ACTGTTTATGAAGATCGGGTTTGGGTTTTTGGTTTTTTTTTTCTTT TTCTTTTTTCCGTGGTGGTGGTGGGTGGGCTTTTGTTCTTTTTGTT TTTTCTGTGGTGGTGGTGGGTGGGCTTTATGAATATACCATATTTT GCCTATTGTTTTTCTATTTATCAGGTGGTGTCATTTGAGTTGTTTT CACCCTCTTGTGACTATGAATAATGATACTATAAACAATCTTATAC AGCATCAGTGTCAAAAATCACTAACATTCCTATACACAGACGTGAC TAAACTTCCAGCTTGGGGTCCCGTGGACCTGCAGCCAGGTGCAGCA GGTCACAGGGCAAGGACACGTGTCATTGGTGACCTTCACTATTCAG TGCCCAGATGCTCAGTGCTCTGTGCAGGCCACCTGGCTGGTCTCAG GTACCGCTGCTCTGTCTCGCTCACCGGCCGGGCTATGTTGATTGTC CCCTCGCGGCGCCCGGAAGCGACCCTCAGTAAACAAAGCCGTGTGT GGGCGCAGCCCCAGAAGCCTGGGGCGCGCAGTCCAGCCCAAGAGAG GCGGGGGAGGAATGTTGTGAATGAACCCCGGGCCCGCCCCGAAACT CCGCATAAGGCCTGGGCCGCGGGGGTCCTCCCACTCTGATTGGCCT CTGGCGCCCCGTGATTGACAGCGCCCCTCGCTGTGCGCTCTGGTTG GGTAAACAAGAAAAGACTGGCATCGCAGTCATCGAGTGAGCAGCGA GGCTTGGACACGGGTCTGGCGGCGCAGCCAATGGCGGGGGAGGGCC GAGGAGGCCGAGGGGGGGCCAATAGGGACAGGCGGTGGGGGCGGGA CGACGGCGGAGCTAAAGCGGCGGCTGAAGCAGCTTCATTGTTGTGA AGAGTCTTAAAGGGGCCGCATCACCCTGCCGGCCCGGCGCGGGTCG GGGGTGGGTGCGGTAGGGGTCCCGGGGCGGCCGAGCGCAGAGGACG GATGTACA |

In one embodiment the invention therefore encompasses a vector comprising a nucleic acid molecule selected from the group consisting of:

a) a nucleic acid molecule comprising or consisting of a nucleotide sequence according to SEQ ID NO 1-6
b) a nucleic acid molecule which is complementary to a nucleotide sequence in accordance with a);
c) nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 70%, 80%, preferably 90%, more preferably 95%;
d) a nucleic acid molecule according to a nucleotide sequence of a) through c) which is modified by deletions, additions, substitutions, translocations, inversions and/or insertions and functionally analogous/equivalent to a nucleotide sequence according to a) through c).

Functionally analogous sequences refer preferably to the ability of the synthetic regulatory regions to promote transcription of an operably coupled reporter or effector gene in a cell type of interest.

In one embodiment the invention encompasses a vector for oncolytic viral therapy comprising a nucleic acid molecule selected from the group consisting of:

a) a nucleic acid molecule comprising or consisting of a nucleotide sequence according to SEQ ID NO 1-6
b) a nucleic acid molecule which is complementary to a nucleotide sequence in accordance with a);
c) nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 70%, 80%, preferably 90%, more preferably 95%;
d) a nucleic acid molecule according to a nucleotide sequence of a) through c) which is modified by deletions, additions, substitutions, translocations, inversions and/or insertions and functionally analogous/equivalent to a nucleotide sequence according to a) through c).
e) a nucleic acid molecule generated according to the method Functionally analogous sequences refer preferably to the ability of the synthetic regulatory regions to promote transcription of viral essential genes and/or effector genes such as co-stimulatory molecules (e.g. cytokines/chemokines) in the diseases target cell of interest and not in non-diseased cells.

FIGURES

The invention is further described by the following figures. These are not intended to limit the scope of the invention but represent preferred embodiments of aspects of the invention provided for greater illustration of the invention described herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE FIGURES

Figure 1:
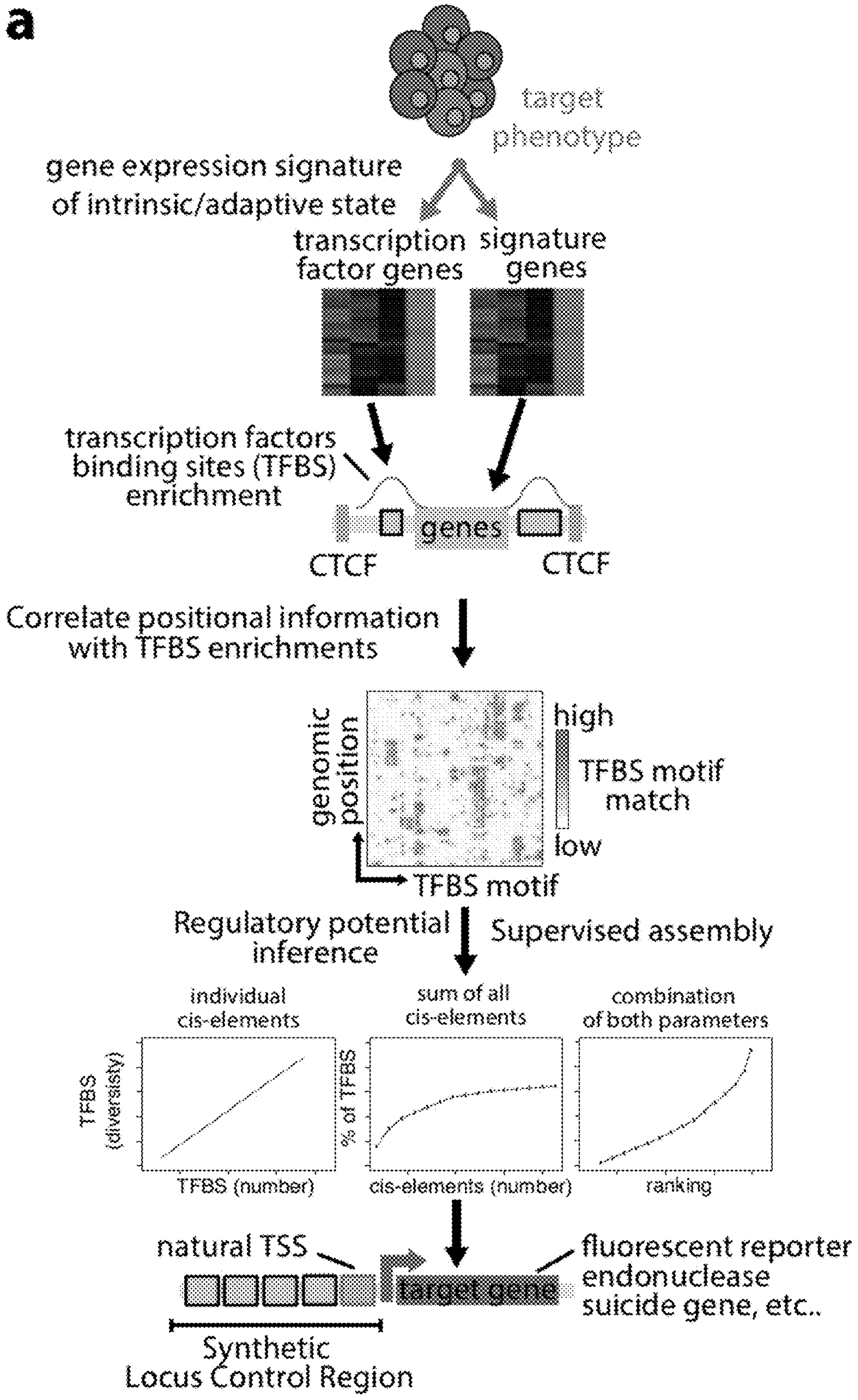
FIG. 1: Generation and validation of Synthetic Locus Control Regions (sLCRs)
Figure 1:
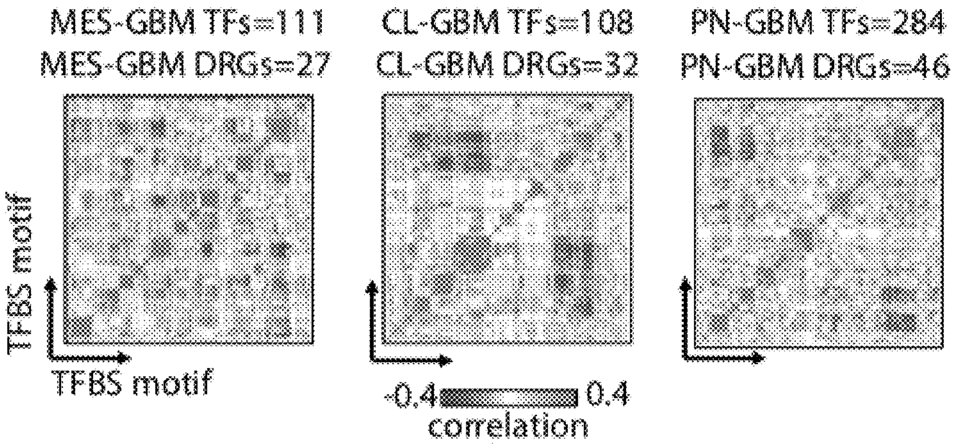
Figure 1:
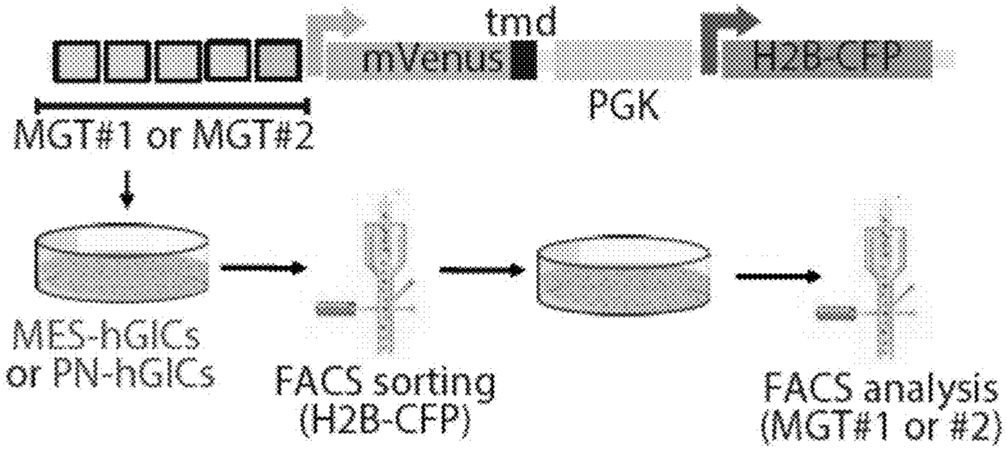
Figure 1:
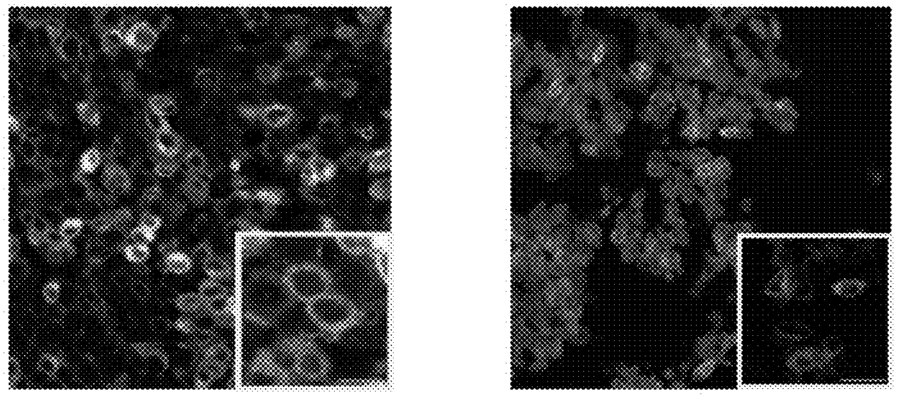
Figure 1:
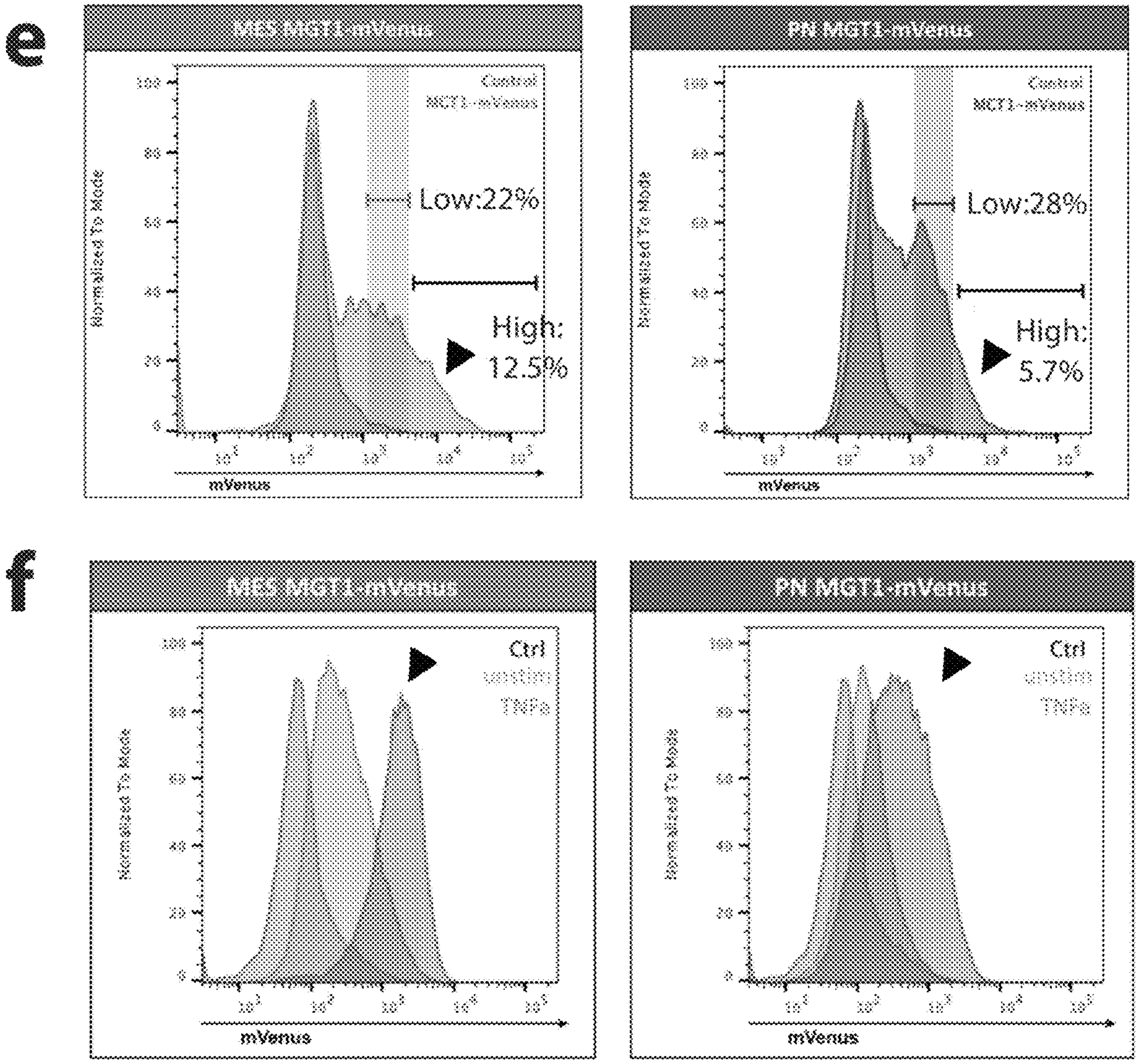
Figure 1:
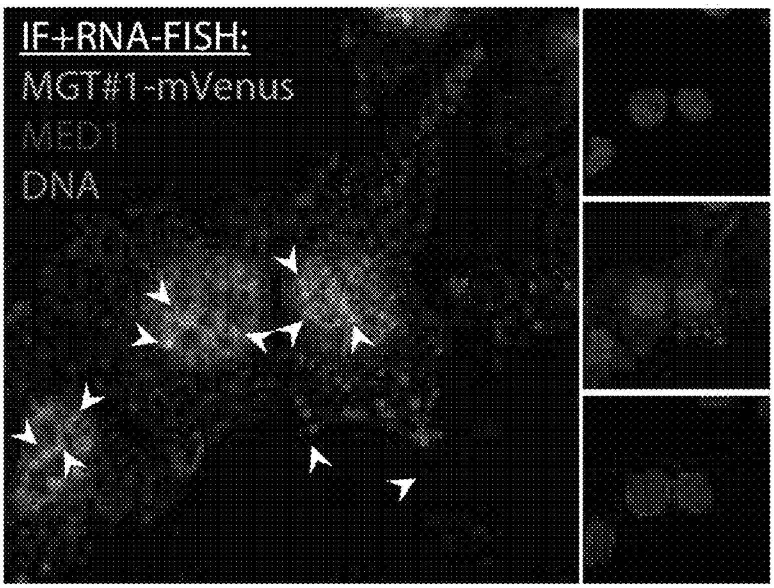
Figure 1:
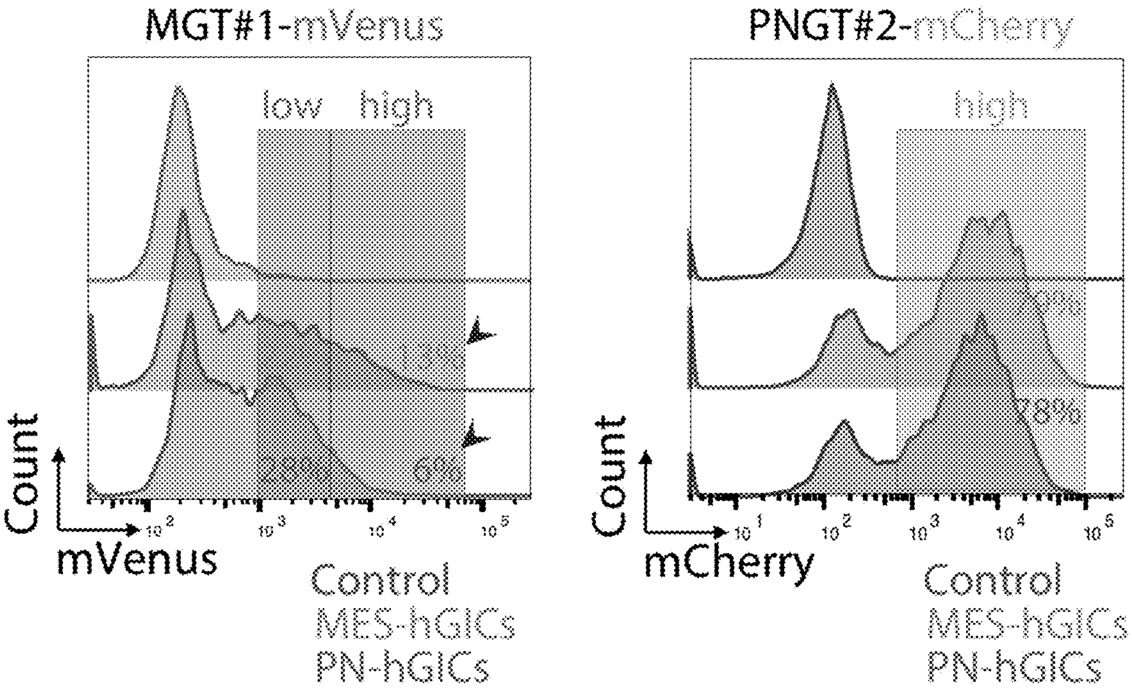

FIG. 1: Generation and validation of Synthetic Locus Control Regions (sLCR). a) Schematic representation of sLCRs generation starting from differentially regulated genes (DRGs). b) Pair-wise correlation heatmap of TFBS motifs detected with significance at genomic GBM subtype-specific loci. The number of TFBS and DRGs in analysis is indicated above each panel. c) Schematic representation of a sLCR and of the experimental steps to generate reported Glioma-initiating-cells (GICs). d) Left; confocal imaging of MGT #1-transfected 293T or (right)—lentivirally transduced cryosected MES-hGICs neurospheres. Scale=10 μM e) Representative mVenus FACS profile of MES-hGICs and PN-hGICs modified with sLCR and FACS sorted for H2B-CFP. MES-hGICs express higher levels of MGT #1 (arrowheads). f) Representative quantification of the response to Tumor Necrosis Factor alpha (TNFa) treatment in the indicated GICs. MES-hGICs express higher levels of MGT #1 (arrowheads). MES=Mesenchymal; PN=Proneural; CL=Classical. MGT #1-2=MES genetic tracing #1-2. tmd=PDRGFRa transmembrane domain. g) Dual IF and smRNA-FISH. Images of the merged (left) and separate channels (right) are shown. Overlapping signal in yellow and arrowheads denote co-localization between MED1 and MGT #1-driven mVenus. h) mVenus FACS profile of MES-hGICs and PN-hGICs transduced with the indicated sLCR and FACS sorted for H2B-CFP. Gating and arrowheads show MES-hGICs expressing higher levels of MGT #1 than PN-hGICs.

Figure 2:
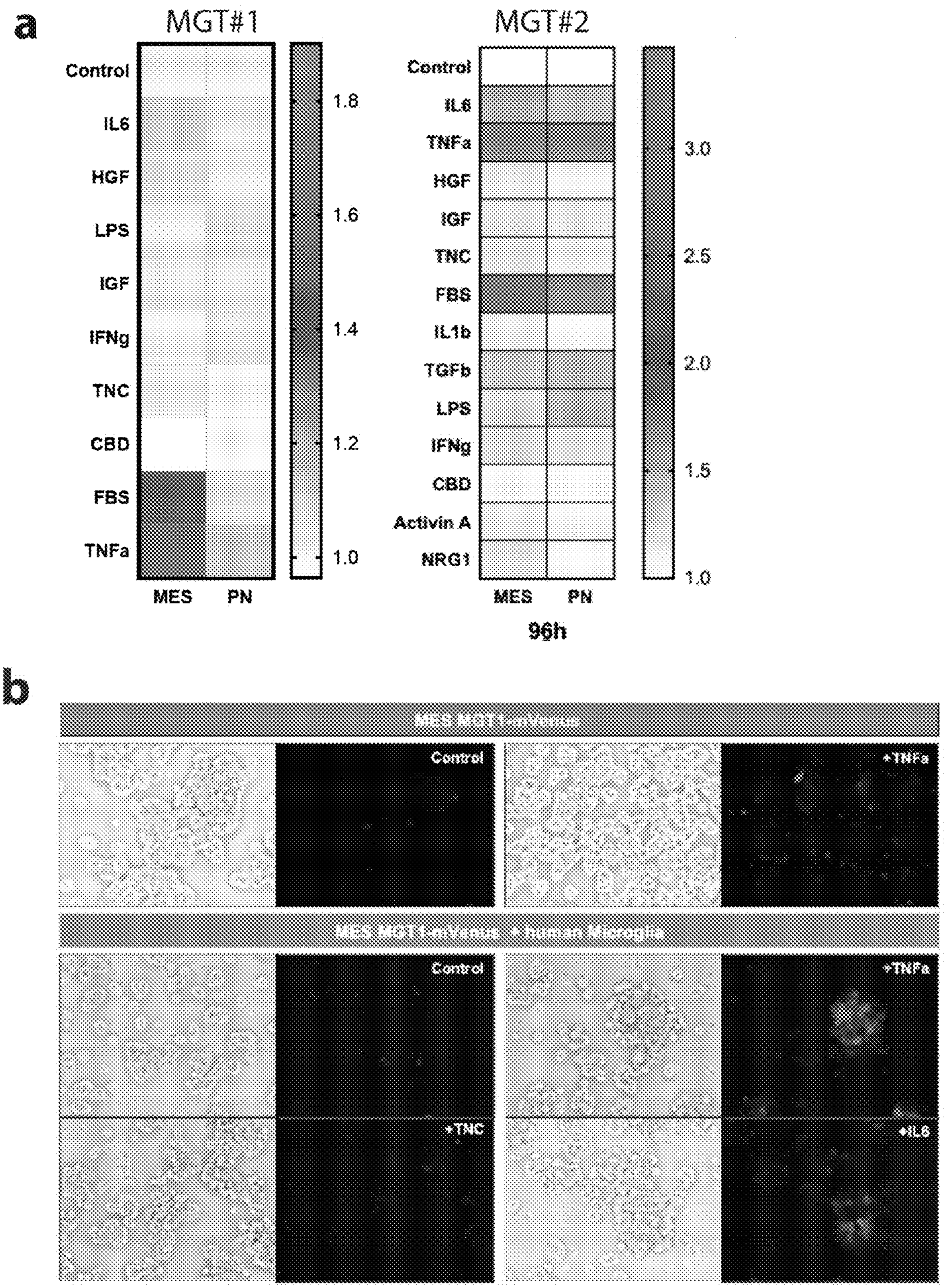
FIG. 2: Intrinsic and Adaptive responses in MES- and PN-GICs revealed by sLCRs.
Figure 2:
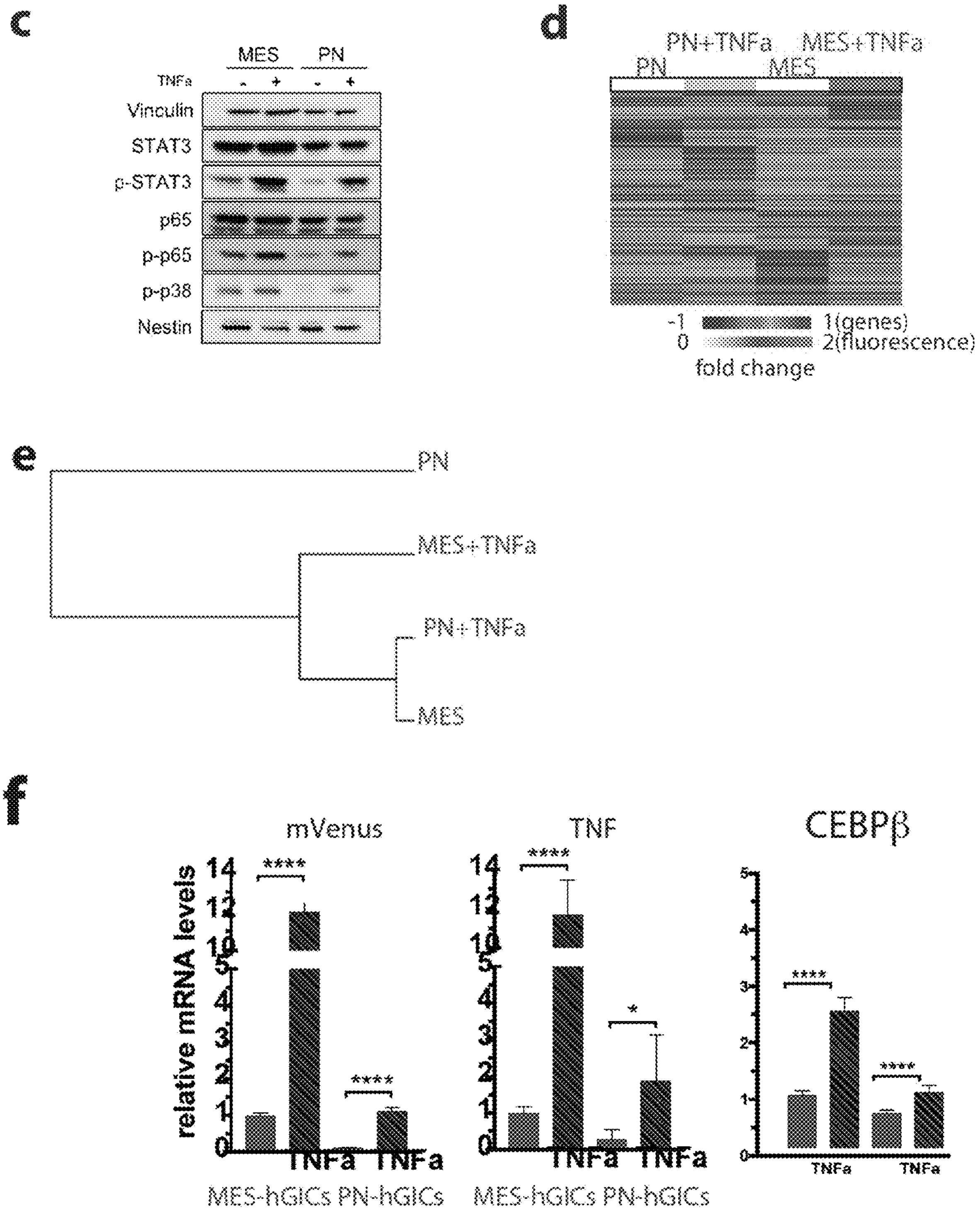
Figure 2:
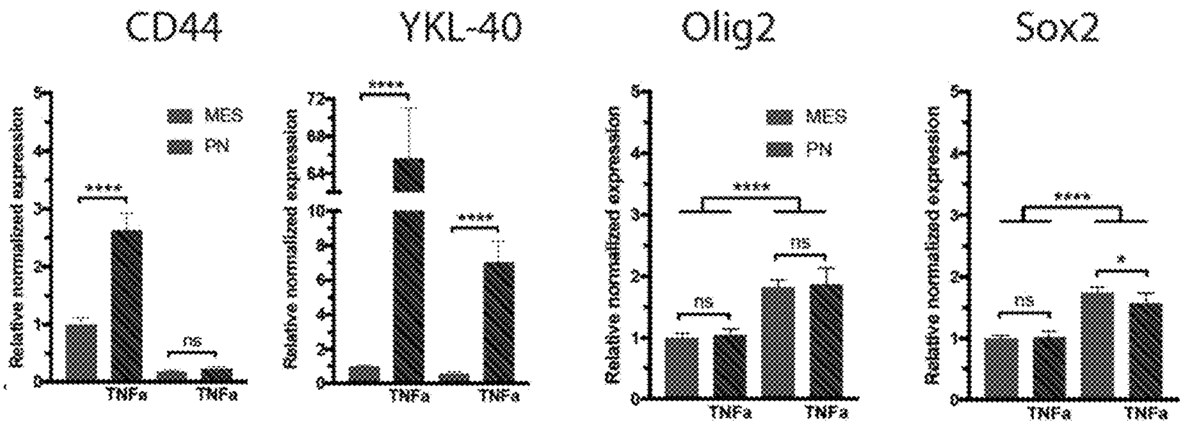
Figure 2:
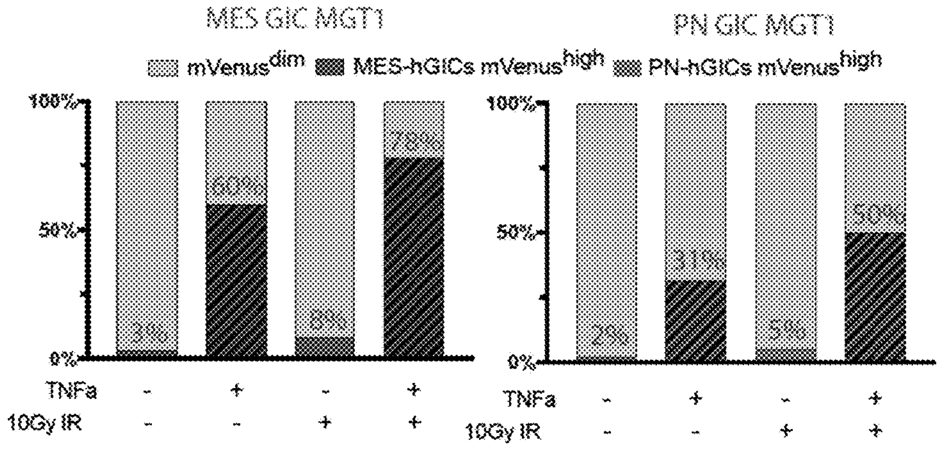
Figure 2:
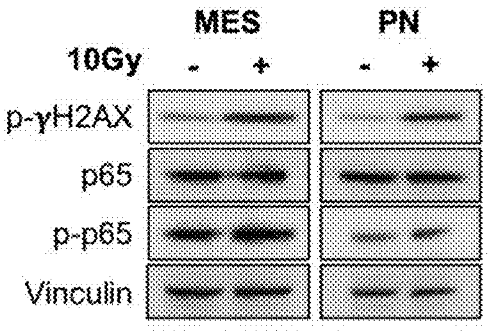
Figure 3:
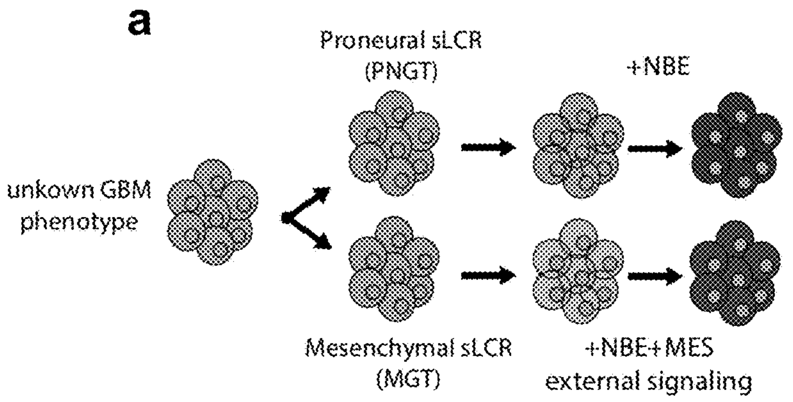
FIG. 3: GBM subtyping and Reprogramming using sLCRs.
Figure 3:
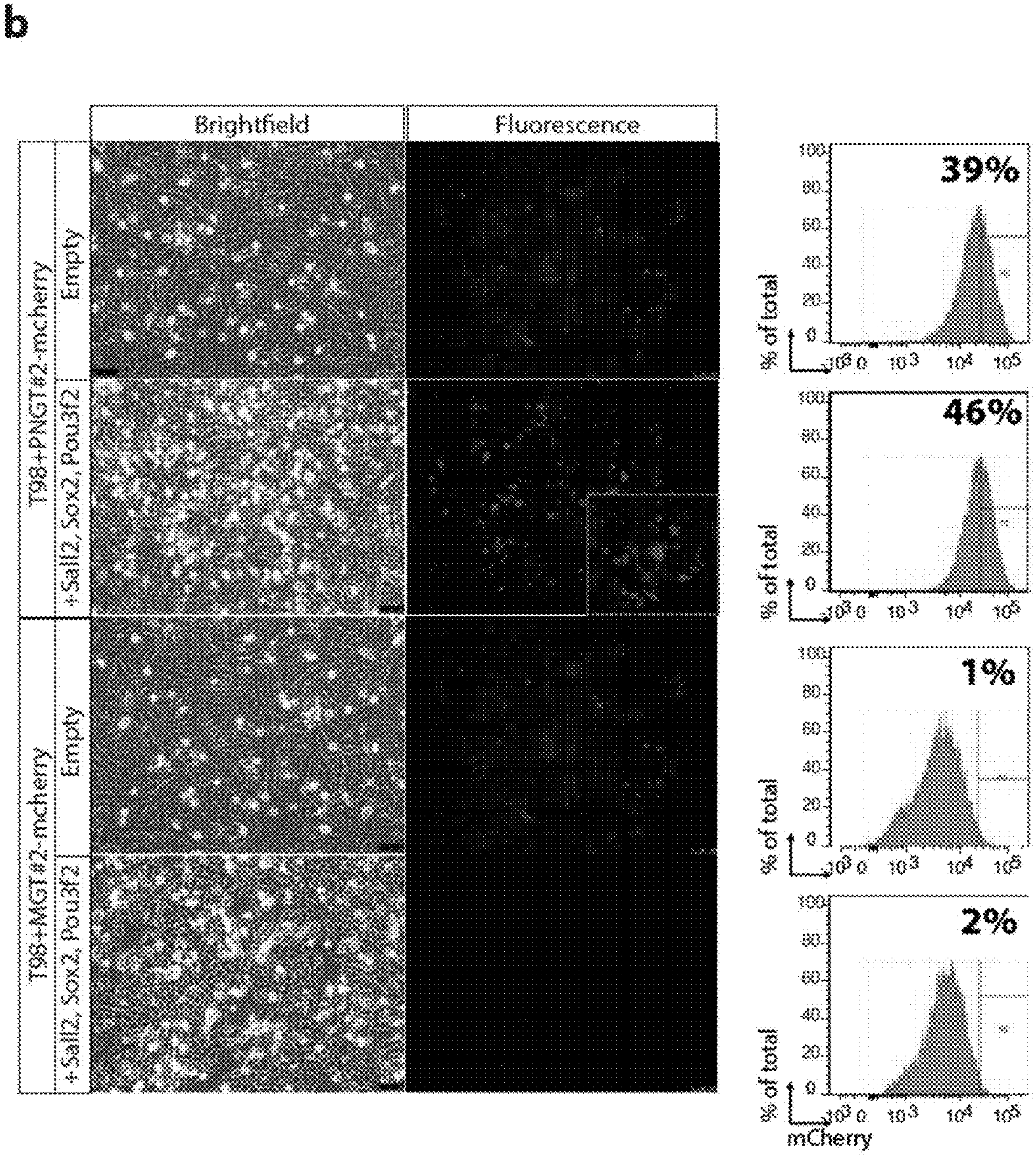
Figure 4:
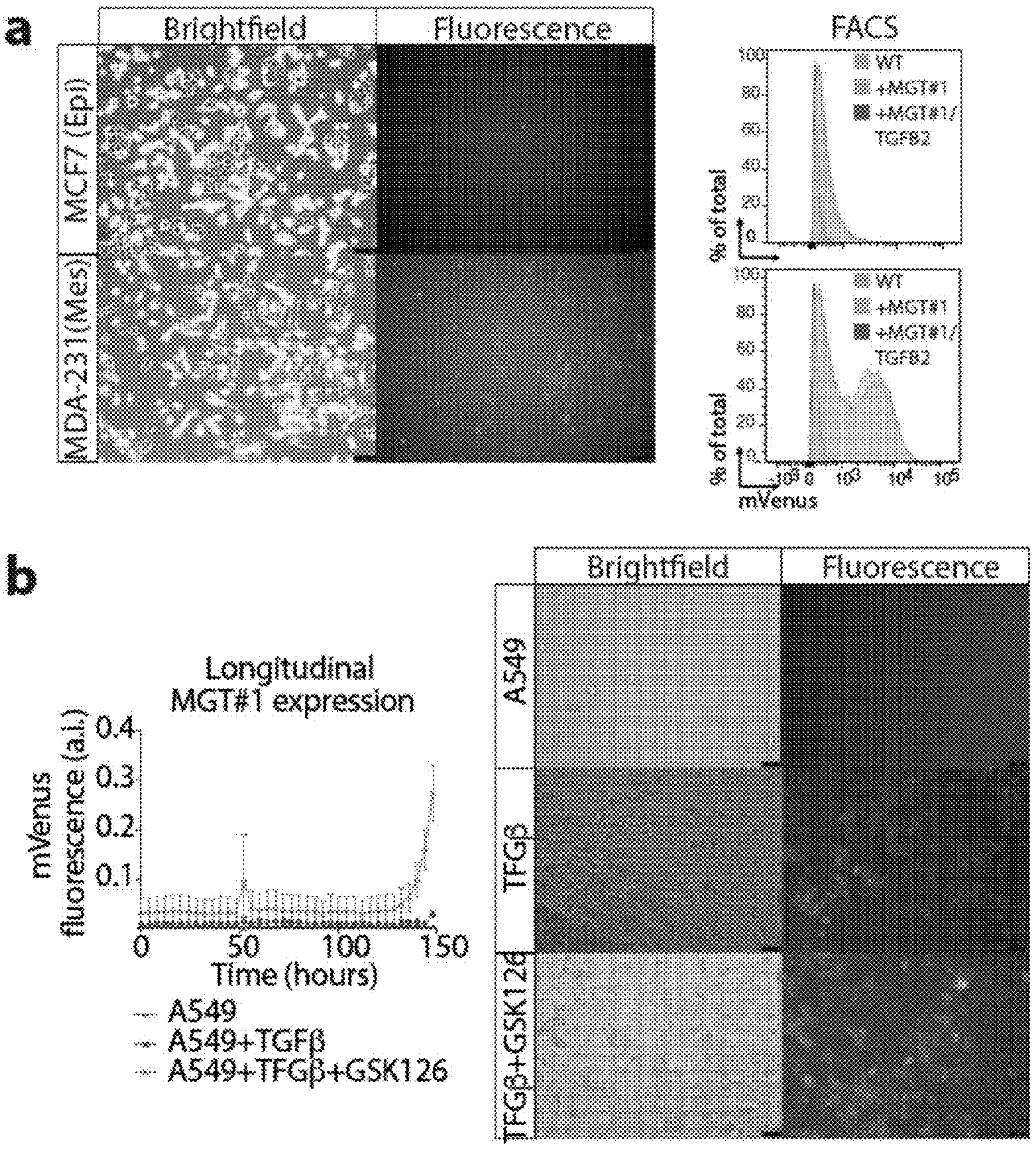
FIG. 4: Tissue-independent Epithelial-Mesenchymal homeostasis revealed by sLCRs.
Figure 4:
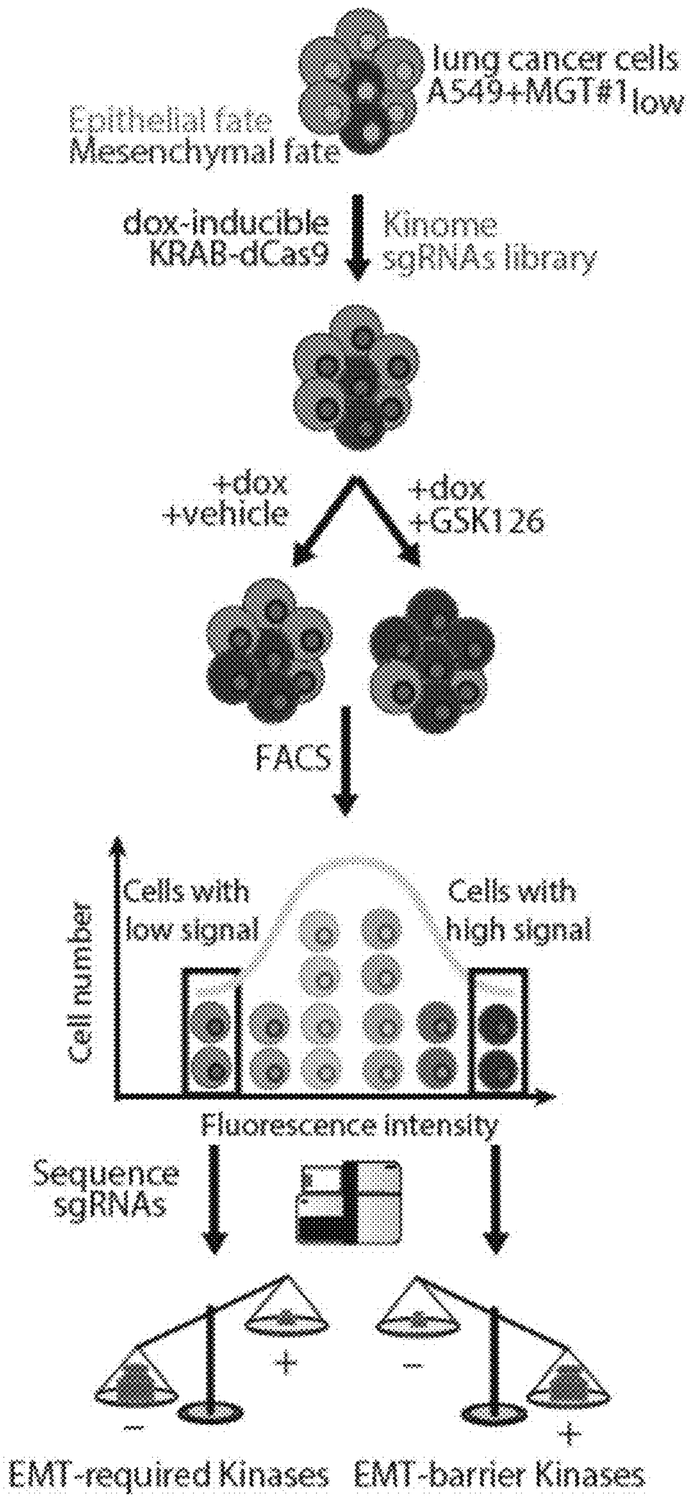
Figure 4:
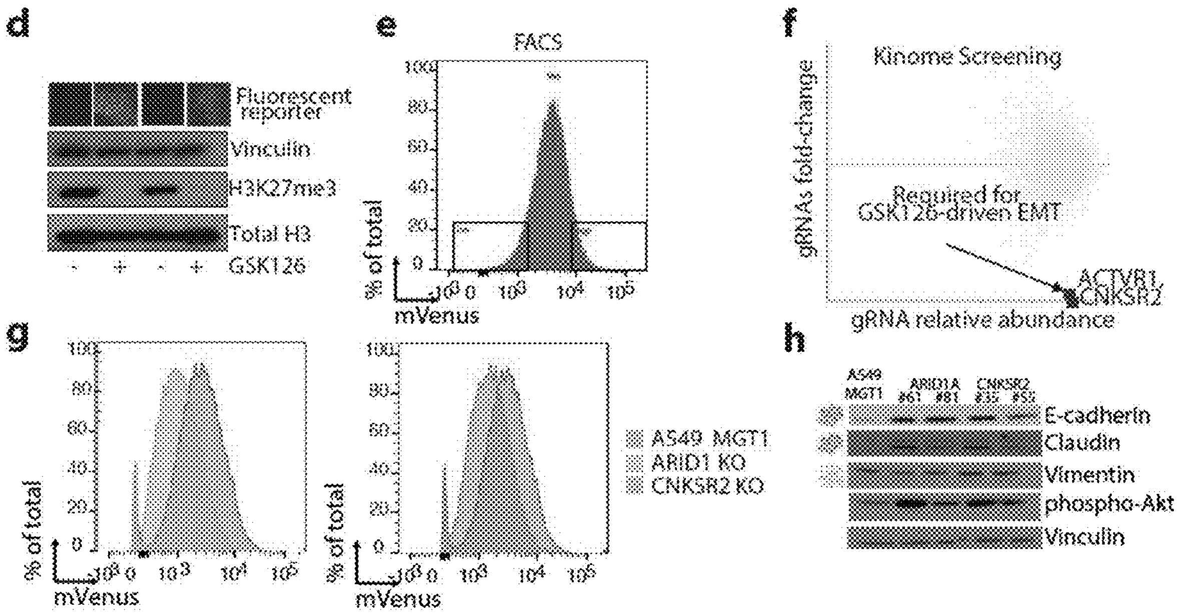

FIG. 2: Intrinsic and Adaptive responses in MES- and PN-GICs revealed by sLCR. a) TFNa is the leading signaling contributing to the Mesenchymal GBM phenotype. Left, TNFa identified as top regulator as activator of two independently designed MES-GBM reporters (MGT #1-MGT #2) in MES-hGICs by adaptive response screening using the indicated cytokines up to 48 hours. Data are normalized to control. MES-hGICs express higher basal levels of MGT #1 compared to PN-hGICs. b) Cooperation between IL-6 and microglia cells in MGT #1-induction. Live cell imaging of MGT #1 expression in MES-hGICs upon the indicated treatments. c) Immunoblotting of the indicated conditions and antibodies. d-e) Differential MGT #1 activation informs on differential adaptive responses to TNFa. Expression changes for genes regulated by TNFa in either MES-hGICs or PN-hGICs measured by RNA-seq and hierarchical sample clustering. f) RT-qPCR validation of the indicated genes in response to Tumor Necrosis Factor alpha (TNFa) treatment in the indicated GICs. n=3 biologically independent samples, ANOVA test; ****P<0.0001; g) Cooperativity between TNFa- and Therapy-induced mesenchymal commitment revealed by MGT #1 expression. FACS quantification of Mesenchymal transdifferentiation upon the indicated stimuli. h) Immunoblotting of the indicated conditions and antibodies. MES=Mesenchymal; PN=Proneural; CL=Classical. MGT #1-2=MES genetic tracing #1-2. FBS=fetal bovine serum, CBD=Cannabidiol. IRR=Ionizing Radiation FIG. 3: GBM subtyping and Reprogramming using sLCR. a) Schematic depiction of the use of GBM subtype-specific sLCR to determine the intrinsic GBM subtype and to reinforce the subtype identity using cellular reprogramming or external signaling. b) Reinforcing the Proneural identity in a conventional glioma cell line. T98 cells were transduced with either a Proneural sLCR or Mesenchymal sLCR driving mCherry as reporter and transfected with the indicated master regulators of PN subtype identity[50] or emtpy transfected. Representative micrograph of T98cells (left) and FACS plot (Right) showing higher high intrinsic and TF-induced expression of the PNGT #2 but not MGT #2 reporter in T98 cells; Scale=100 μM FIG. 4: Tissue-independent Epithelial-Mesenchymal homeostasis revealed by sLCR. a) MGT #1 reveals intrinsic cell fate differences in breast cancer cells. Left, representative expression of the MES-GBM reporter MGT #1 transduced into epithelial (top) and mesenchymal (bottom) breast cancer cells. FACS plot showing higher high intrinsic expression of the reporter in MDA-231 than in MCF7 cells. Note that reporter expression is independent of the mesenchymal inducer 10 μM TGFβ2. Scale=100 μM. b) MGT #1 reveals adaptive responses to chemicals/morphogens in lung cancer cells. Left, representative MGT #1 expression in A549 cells seeded in 96-well and propagated for the indicated time. 300,000 cells/plate were propagated in RPMI medium. 10 μM TGFβ1+2 and 5 μM GSK126 were supplemented at 0 and 48 hours. Fluorescence was measured and Right, representative micrograph (right) were taken by IncuCyte imaging system. Error bars represent s.d. of independent wells (n=3). c) CRISPRi and MGT #1 reveal mechanistical regulators of lung cancer EMT. Schematic diagram depicting screen. Dox, doxycycline. d) Immunoblotting of representative intermediate time-point of the CRISRPi screening. MGT #1-uorescence micrograph was taken before lysis. e) FACS sorting gating strategy for purifcation of MGT #1 high and low populations. f) MA plot showing relative enrichment of gRNAs in the MGT #1 high-MGT #1 CRISPRi screen. Note the two dropout gRNAs identifying a known and a novel regulator of EMT. g) CRISPR-mediated knockout of ARIDIA and CNKSR2 using two independent gRNAs and followed by FACS validation of MGT #1 expression. h) Immunoblotting of EMT markers in wild-type and ARID1A and CNKSR2 KO cells.

Figure 5:
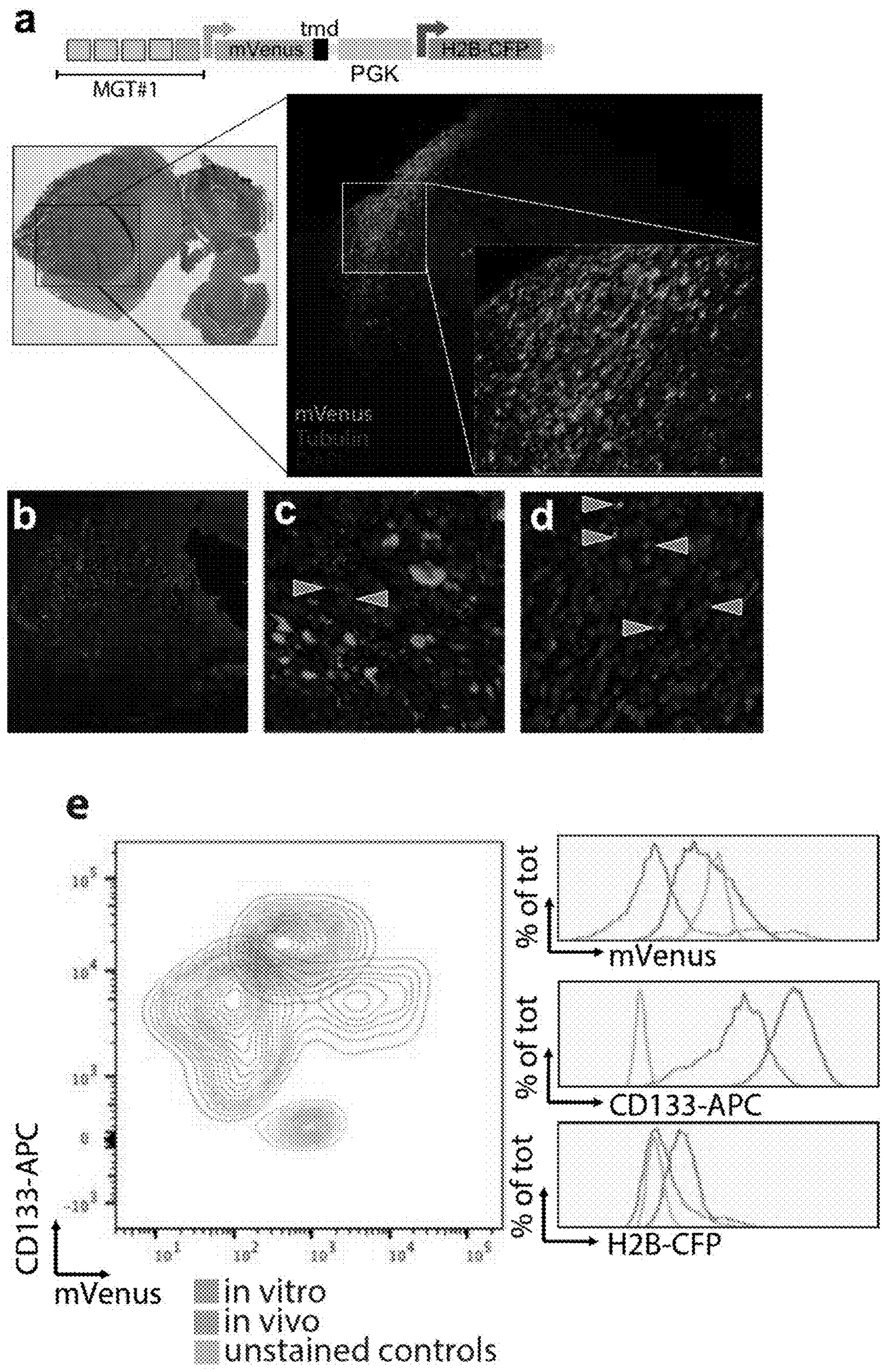
FIG. 5: Heterogenous Mesenchymal trans-differentiation revealed by sLCRs in vivo.
Figure 5:
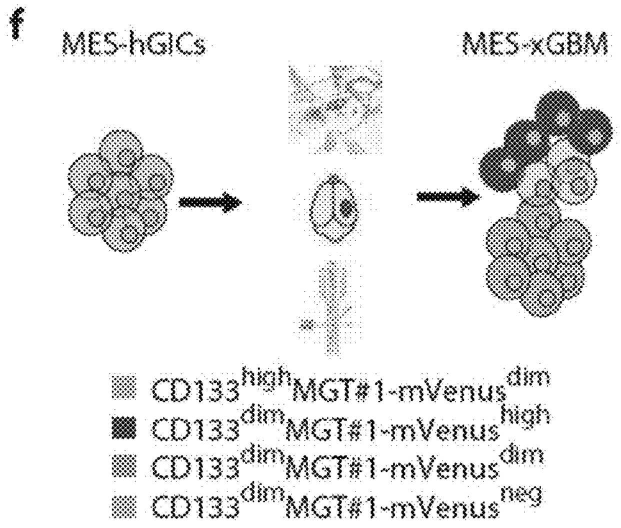

FIG. 5: Heterogenous Mesenchymal transdifferentiation revealed by sLCRs in vivo. a) Representative coronal forebrain images of MES-hGICs; MGT #1-mVenus$^{dim}$ xenografts in NSG mice (n=10) at humane end point. Left, HE staining; right progressive insets showing magnification of GFP, Tubulin and DAPI counterstained tissue. Note the invasive glioma front being homogeneously MGT #1-mVenus$^{high}$. b) Representative mixed MGT #1-mVenus$^{high}$/MGT #1-mVenus$^{neg}$ lesion. c-d) Representative H2B-CFP expression (arrowhead) in MGT #1 positive and negative lesions, respectively. e) Representative Flow cytometry plots showing CD133 and MGT #1-mVenus expression in MES-hGICs;MGT #1-mVenus$^{dim}$ xenografts in NSG mice or in vitro (left). Individual components are shown to the right. Note the profole shift from in vitro to in vivo. f) Schematic representation of data presented in a-e.

Figure 6:
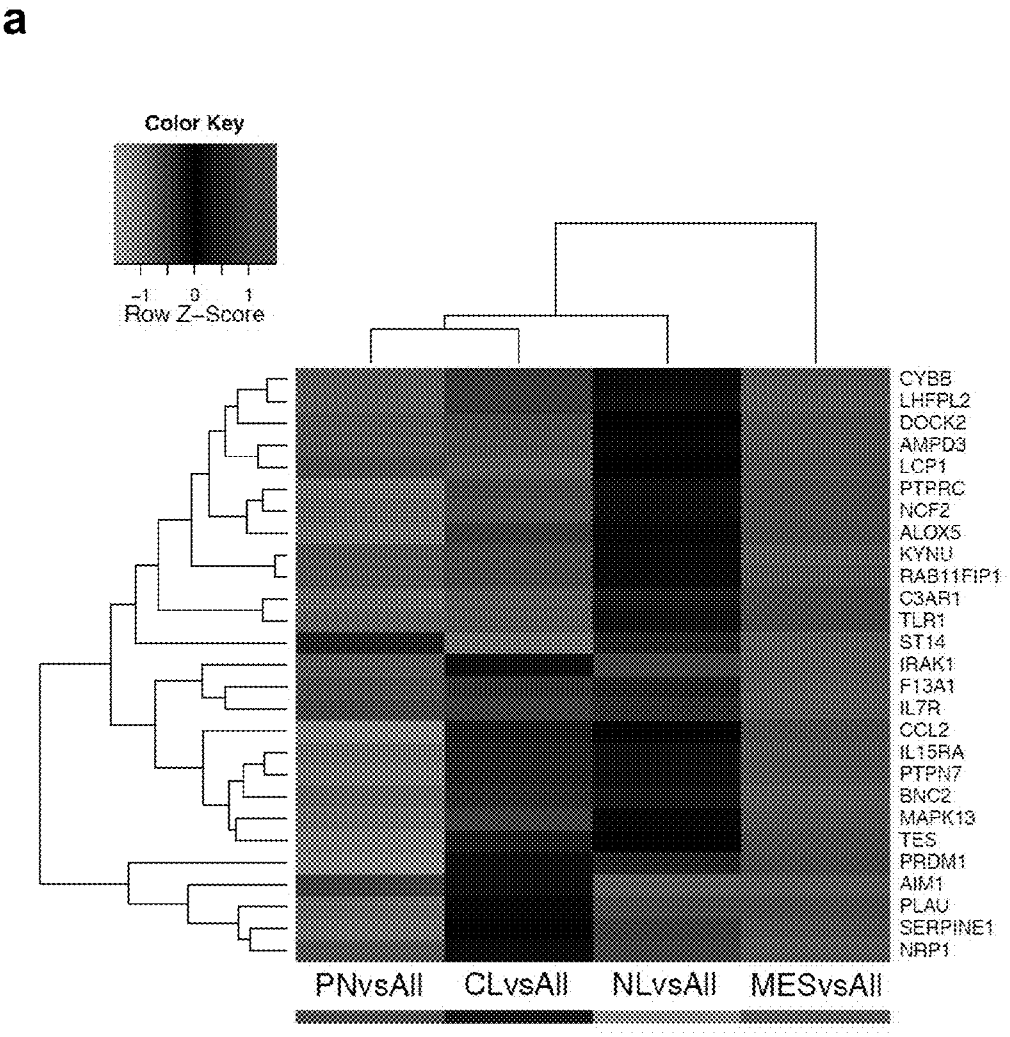
FIG. 6: Selection of MES GBM-subtype subtype-specific genes.
Figure 6:
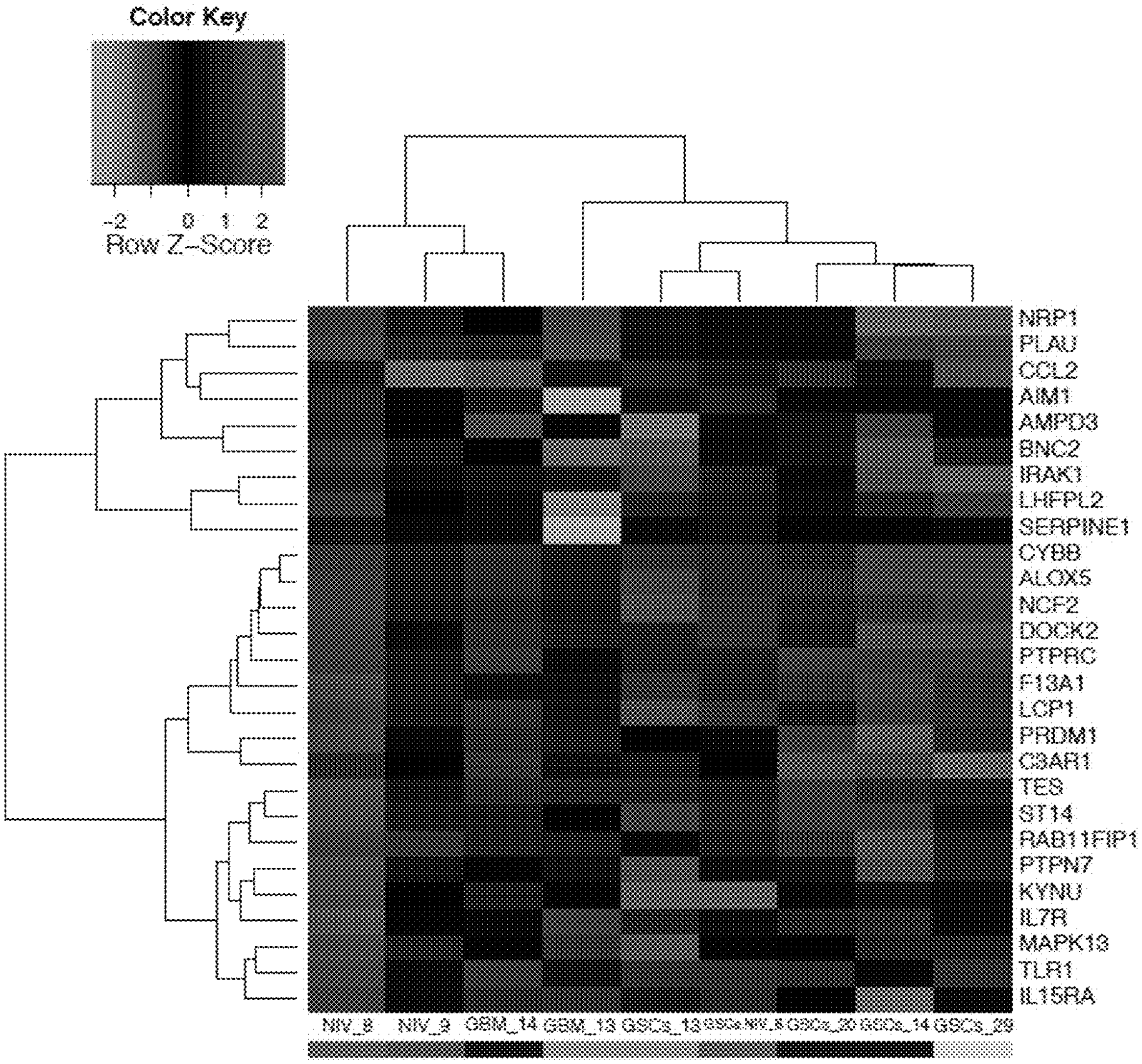

FIG. 6: Selection of MES GBM-subtype subtype-specific genes. a) Heatmap representing the fold change for selected genes from TCGA rank-ordered Significance Analysis of Microarrays (SAM) lists for the indicated pair wise comparisons. Below, color code indicating the metadata-associated GBM subtype expression profile. b) Heatmap representing the expression level for the selected genes illustrating their expression and fold-changes in primary biopsies and glioma-stem-like cells (GSCs) derived from these. Below, color code indicating the metadata-associated GBM subtype expression profile. All genes have absolute CPM>4 and most genes show a fold-change within the GSCs, suggesting their expression to be contributed also in cell autonomous manner. Spearman Rank Correlation was used for samples and Pearson Correlation was used for genes.

Figure 7:
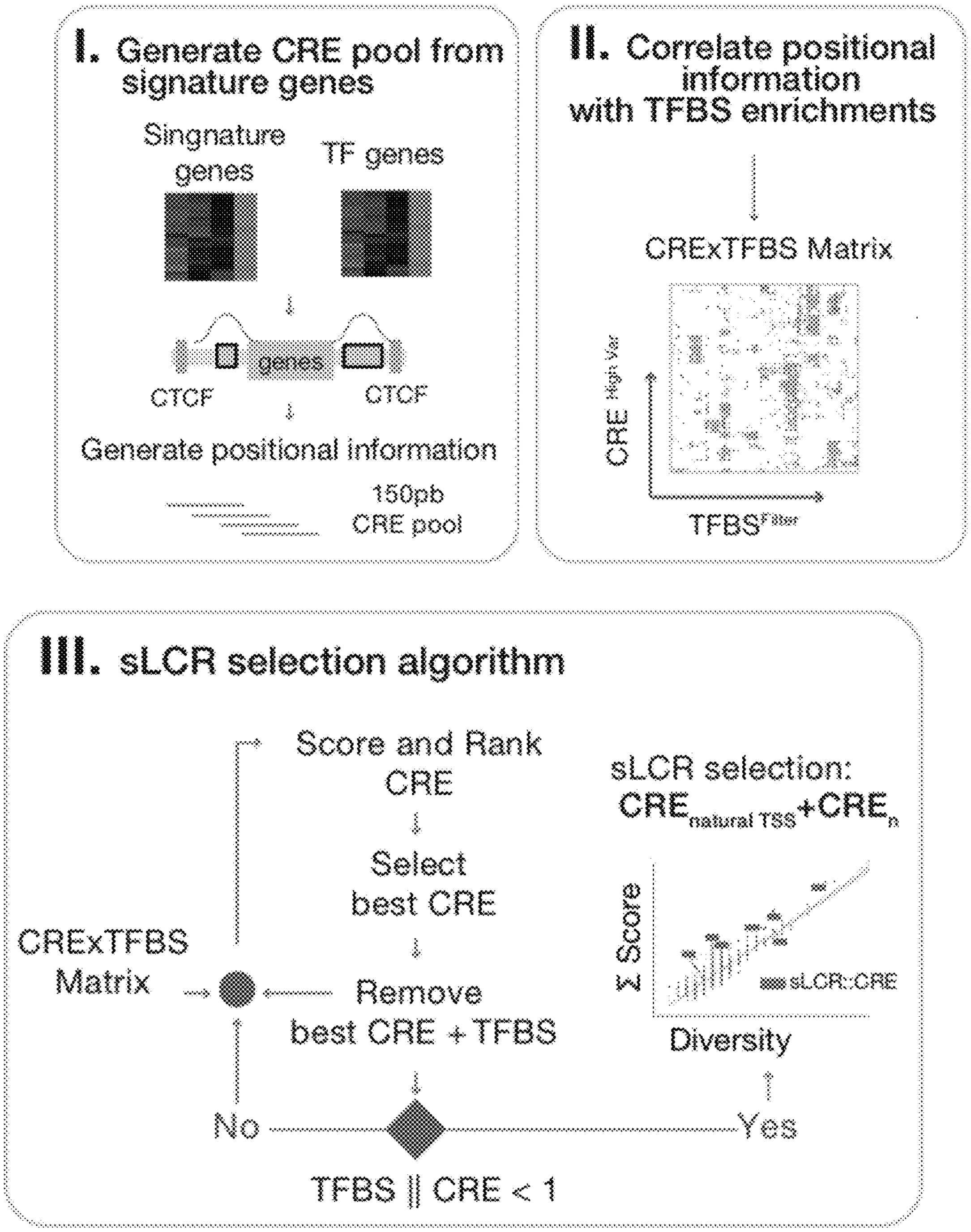
FIG. 7: Automated Synthetic Locus Control Regions (sLCR) generation.
Figure 7:
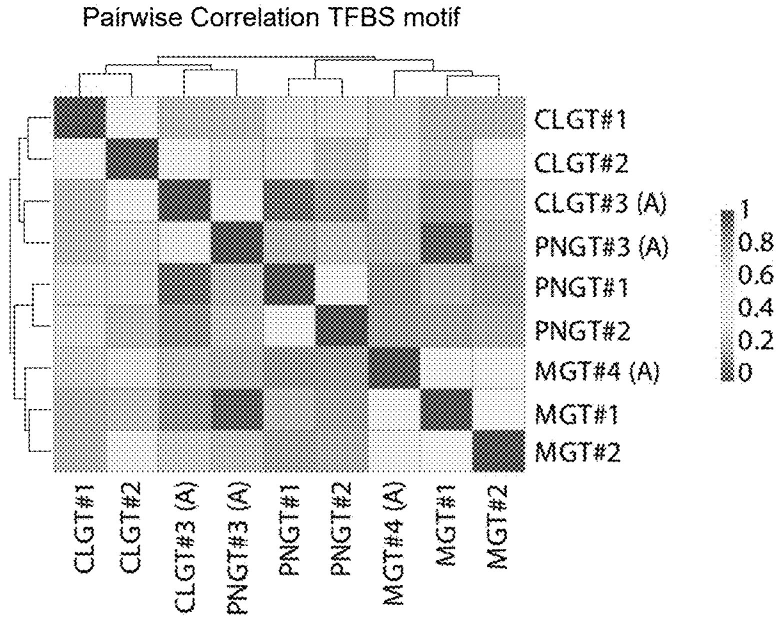

FIG. 7: Automated Synthetic Locus Control Regions (sLCR) generation. a) Upper left (I), schematic representation of identification of cis-regulatory elements (CREs) associated with specific gene signatures; upper right (II), annotation of CRE to genomic positions; below (III), iterative selection of 150 bp CREs based on TFBS diversity and score [Σ-log 10(pvalue)+num TFBS)]. sLCR generation involves assembly of n CREs from the closest to a natural TSS to the farthest distal-CREs, up to >50% of the TFBS diversity (MES-GBM in the example). b) Spearman correlation of individual sLCRs based on TFBS score/diversity. (A) denotes sLCRs generated by an automated algorithm.

Figure 8:
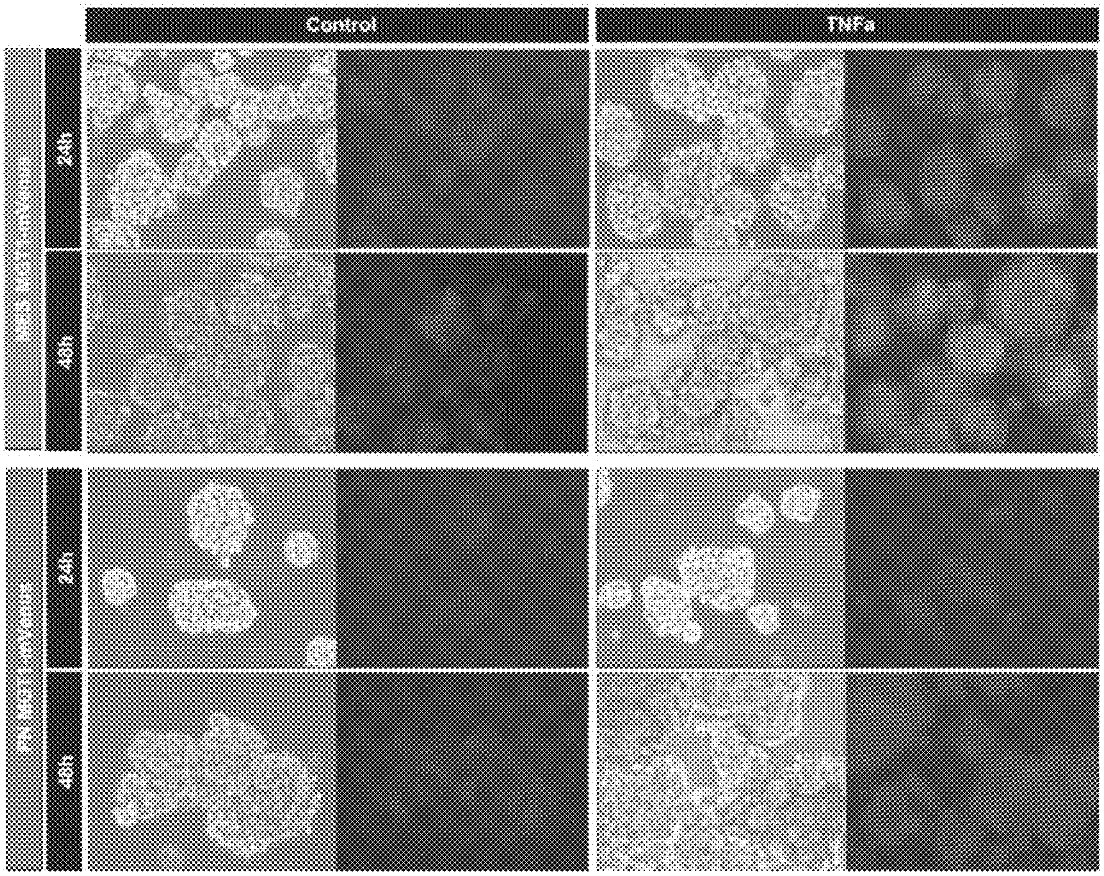
FIG. 8: Intrinsic and Adaptive responses in MES- and PN-GICs revealed by sLCR.

FIG. 8: Intrinsic and Adaptive responses in MES- and PN-GICs revealed by sLCR. Representative live cell imaging of MGT #1 expression in GICs from FIG. 2*a*.

Figure 9:
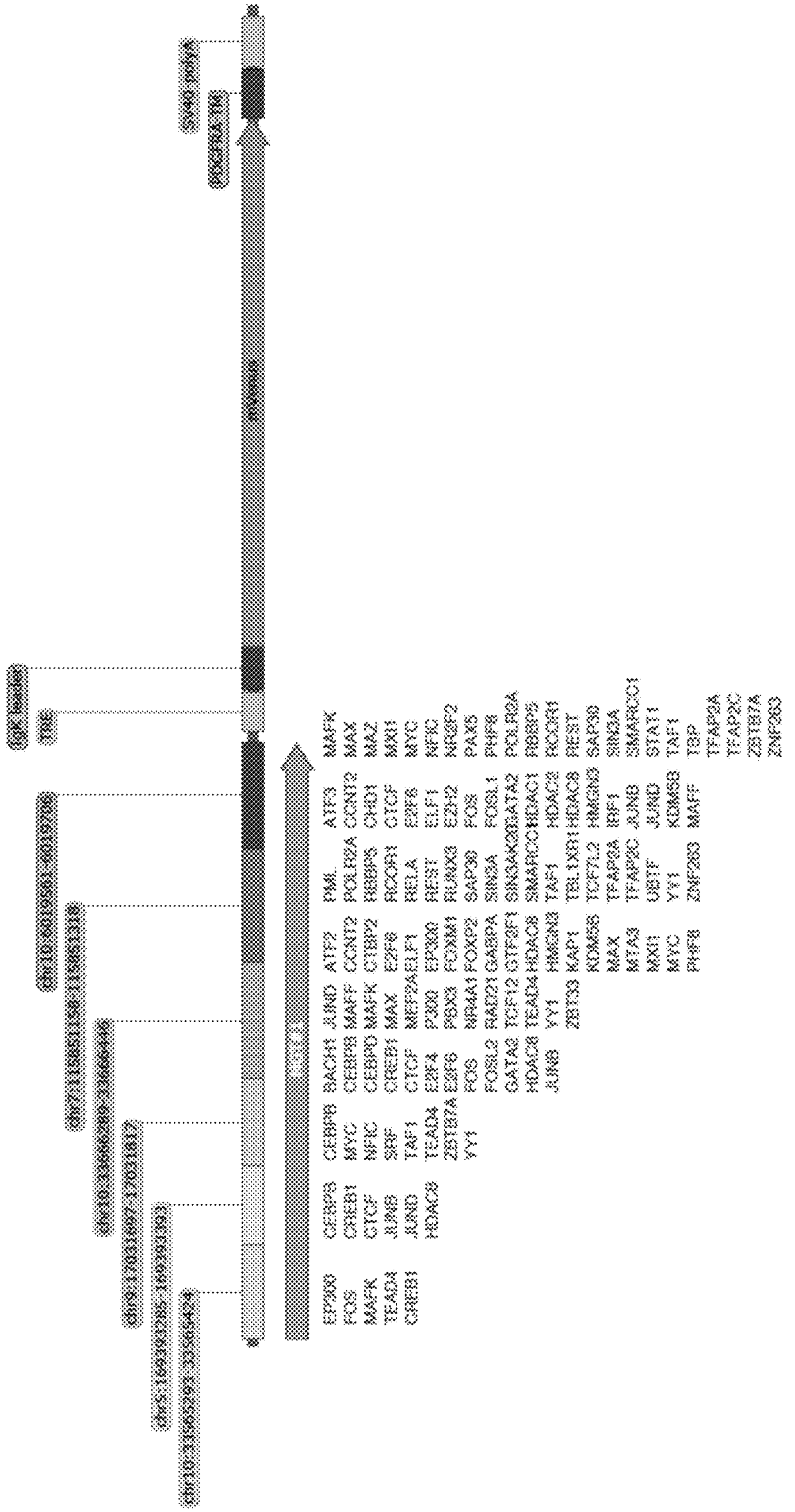
FIG. 9 Transcription Factors binding to mesenchymal glioblastoma (MGT) #1 cis-regulatory DNA.

FIG. 9: Transcription Factors binding to MGT #1 cis-regulatory DNA. a) Above, schematic representation of MGT #1 sLCRs. Below, a list of TFs for which ChIP-seq signal can be observed in the ENCODE public database in any of the cell lines used.

Figure 10:
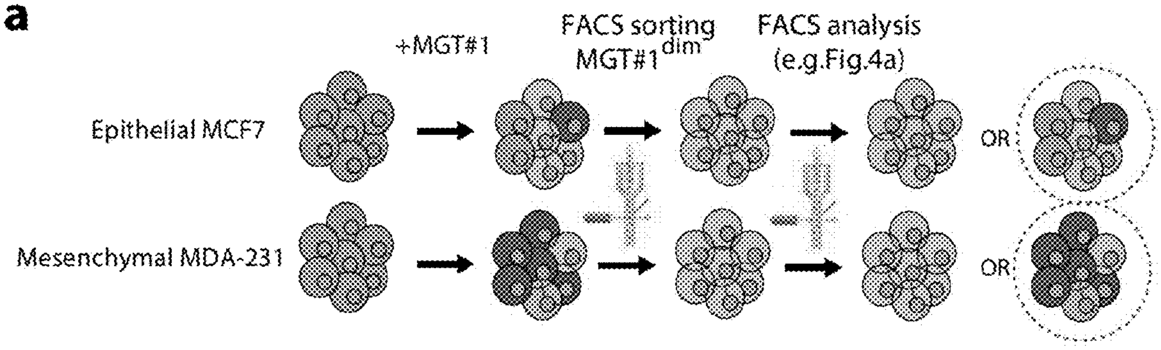
FIG. 10: Homeostatic maintenance of MGT #1 expression in breast cancer cells.
Figure 10:
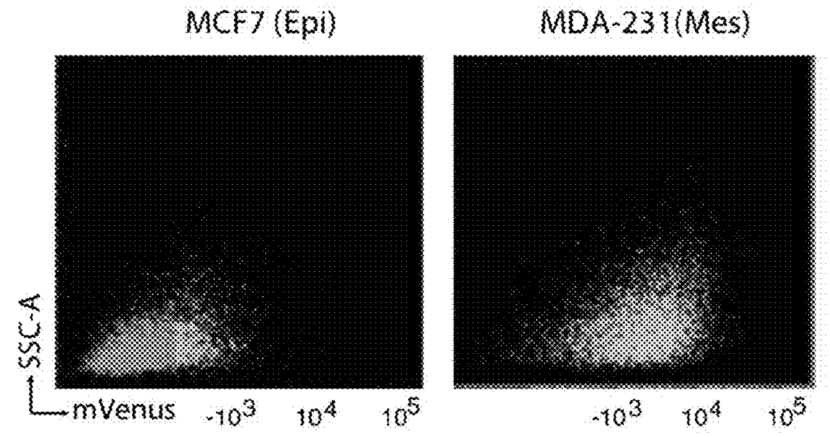

FIG. 10: Homeostatic maintenance of MGT #1 expression in breast cancer cells. a) Schematic depiction of the two hyphoteses being tested: MGT #1 statically reflects a cell state or MGT #1 dynamically reflects cell homoestasis and in vitro homeostatic regulation is reestablished after perturbation (i.e. FACS purification of a MGT #1 dim population). The green dashed circles highlight results in FIG. 4*a* in which MCF7 and MDA-231 are shown to have intrinsic low or high MGT #1 expression, respectively, owing to their cell identity. b) MCF7 and MDA231 were FACS sorted based on the best comparable MGT #1 intensity and propagated in vitro before FACS analysis shown in 4a.

Figure 11:
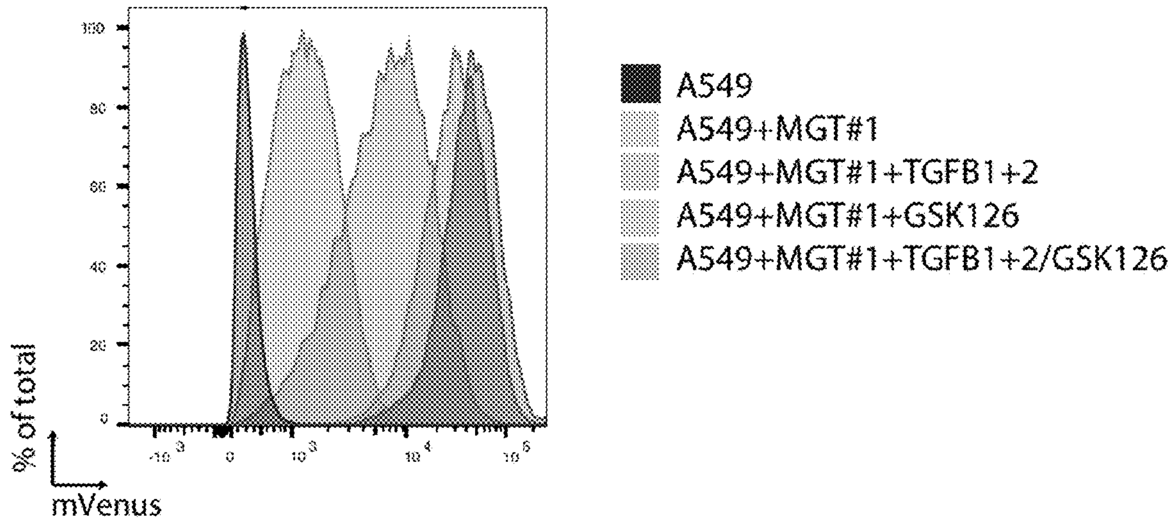
FIG. 11: MGT #1 reflects single and combinatorial contribution for TGFB and GSK126 to EMT.
Figure 11:
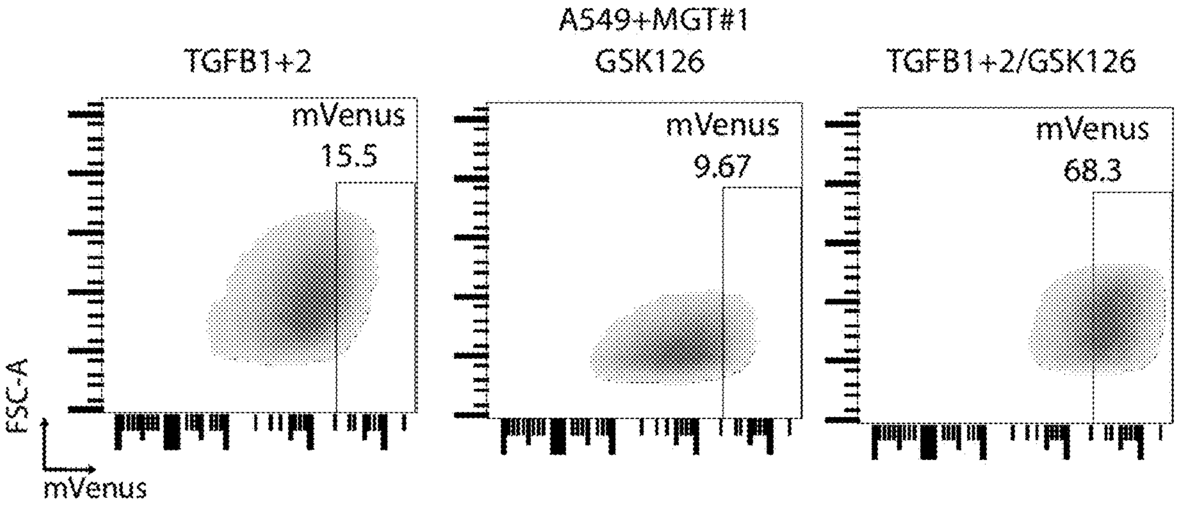

FIG. 11: MGT #1 reflects single and combinatorial contribution for TGFB and GSK126 to EMT. a) FACS profile of MGT #1 expression in A549 cells exposed for 5 days to the indicated treatments. A minimum of 10,000 cells were acquired per sample. b) FACS profile of MGT #1 expression and cell morphology in A549 cells exposed for 5 days to the indicated treatments. Note the TGFB-dependent change in cell shape and the cooperativity between TGFB1+2 and GSK126.

Figure 12:
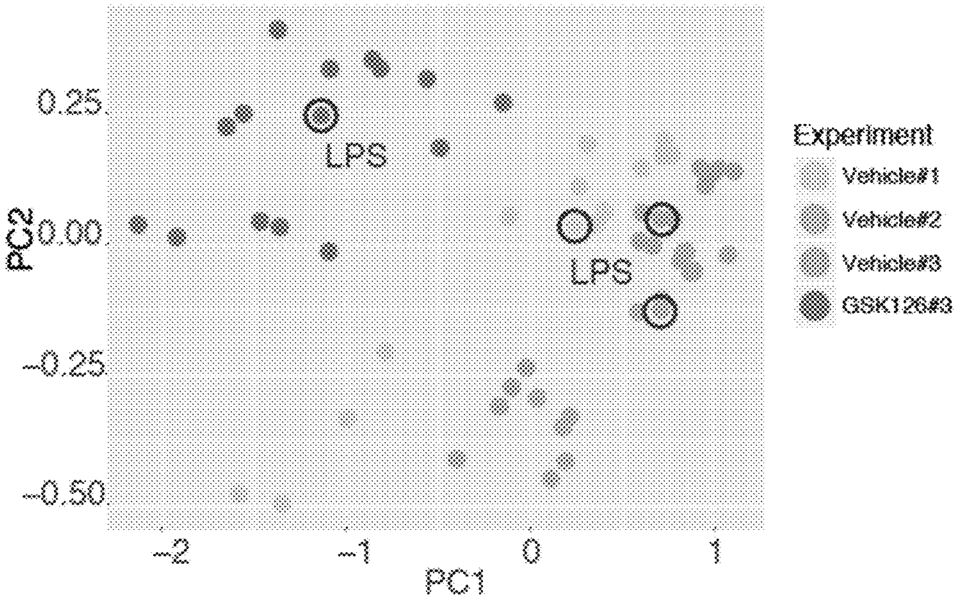
FIG. 12: MGT #1 enables screening for cell fate transitions driven by external signaling and/or chemical perturbations.

FIG. 12: MGT #1 enables screening for cell fate transition driven by external signaling and/or chemical perturbations. Shown is the Principal Component Analysis (PCA) of the data obtained from the screen. The two components PC1 and PC2 explain the largest variation in experiment. To generate the data, A549-MGT #1 cells were propagated and cell images were taken at the end of the procedure for naive epithelial A549-MGT #1 and GSK126-treated cells. Note the mesenchymal transition consistent with previously published data. Hierarchical clustering was carried out of normalized florescence data from A549-MGT #1 cells were propagated and bottom reading fluorescence was scanned using a SPARM 20M TECAN plate reader. Clustering used Pearson correlation. The color codes indicate fluorescence intensity fold changes (blue-white-red) and biological replicas (yellow/orange=vehicle, green=GSK126). Live cell imaging showing response to LPS in GSK126 treated and control A549-MGT #1 cells, was carried out.

Figure 13:
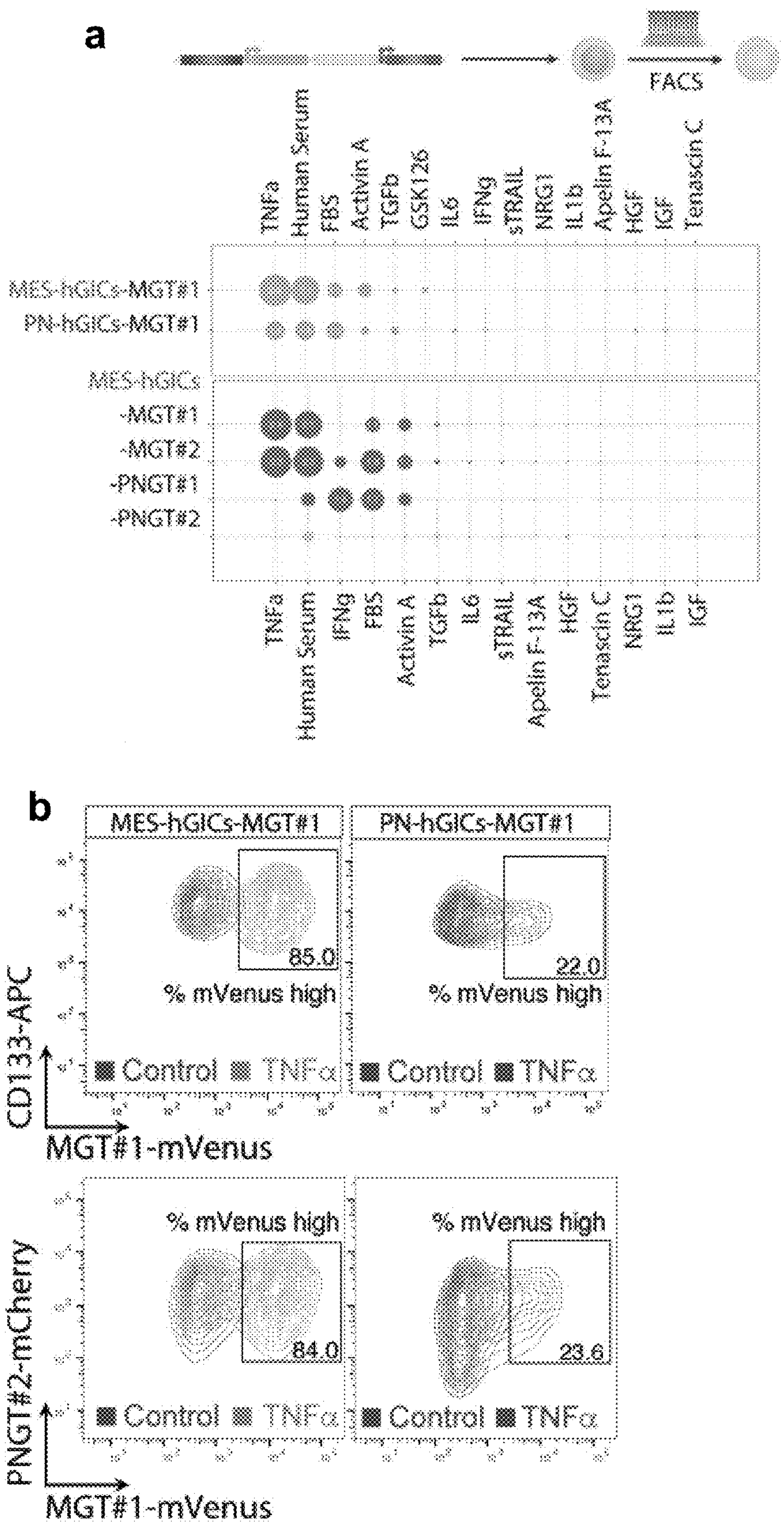
FIG. 13: Intrinsic and Adaptive responses in MES- and PN-GICs revealed by sLCR—expanded.
Figure 13:
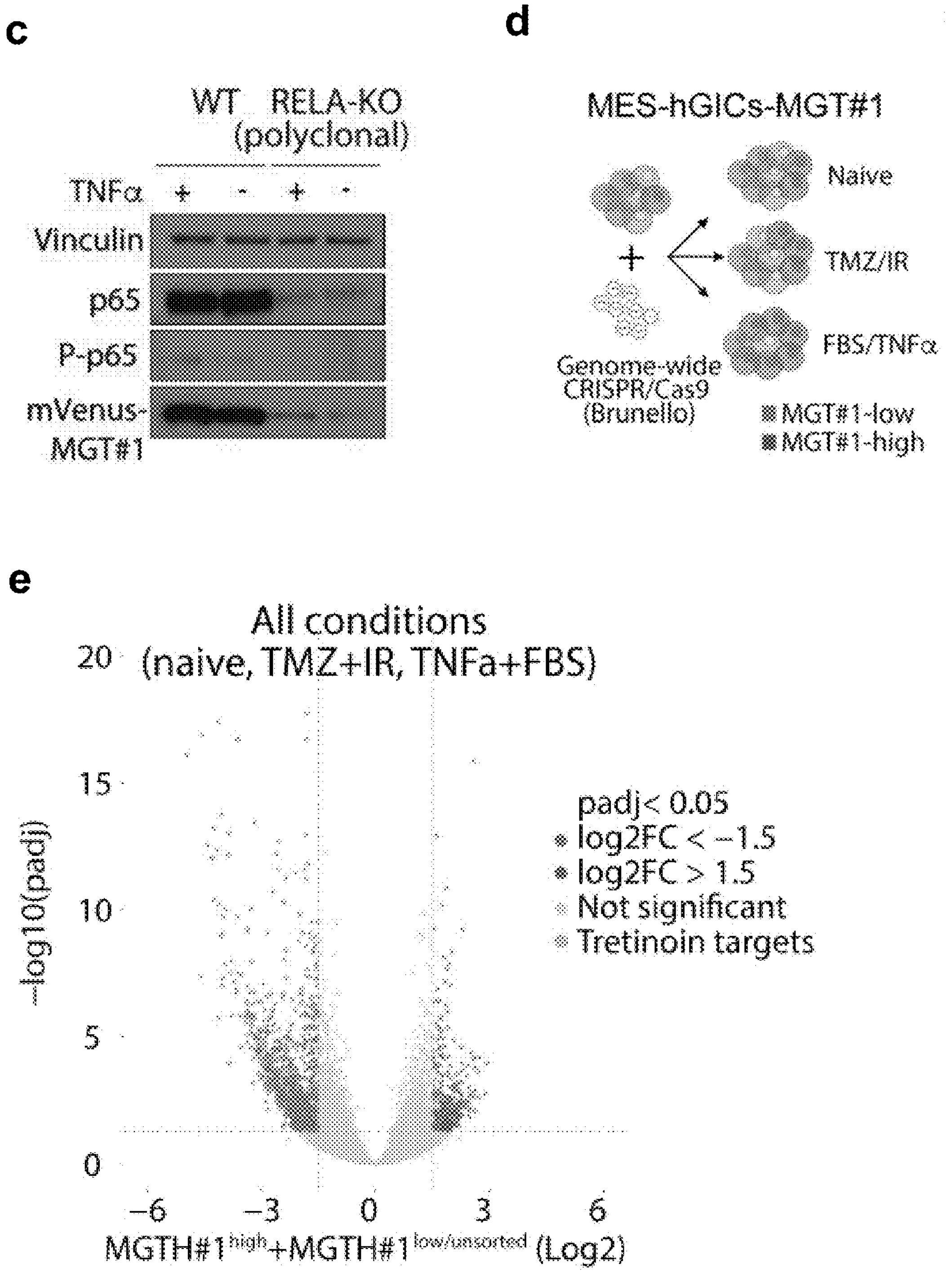

FIG. 13: Intrinsic and Adaptive responses in MES- and PN-GICs revealed by sLCR. a) Schematic description of phenotypic screening using sLCRs (above) and bubble plot visualization of the outcome (below). For each GICs and sLCR, bubble size shows the magnitude of the change for each treatment over control (log 2-fold-change), with bubble color indicating the sign of the change (red or orange for enrichment, light blue for depletion). b) FACS validation of the phenotypic screening. Surface expression of CD133 and PNGT #2 were endogenous markers of cell identity. Note higher MES-hGICs MGT #1 expression compared to PN-hGICs. c) Representative FACS quantification of Mesenchymal trans-differentiation upon the indicated stimuli. d) Experimental design for the functional dissection of MGT #1 activation. e) Volcano plot of drug-associated sgRNAs from the screen in d (red, positive regulators; blue, negative regulator; grey, not significant). Fold-changes for all MGT #1$^{high}$ fractions (n=3, average of naïve, TMZ+IR, TNFa+FBS) were calculated relative to all MGT #1$^{low}$ fractions and unsorted controls (n=6). Padj was calculated by DeSeq2 (see methods). Selected sgRNA-compound-pairs are highlighted. f) RT-qPCR of the indicated genes upon sequential treatment with the indicated treatments and TNFa. Padj is indicated for representative comparisons and denotes results from overall 2-way ANOVA and Dunnett's multiple comparisons. MES=Mesenchymal; PN=Proneural; MGT

#1-2=MES genetic tracing #1-2. FBS=fetal bovine serum, TNFa=Tumor-necrosis factor-alpha. IR=Ionizing Radiation. TMZ=Temozolomide.

Figure 14:
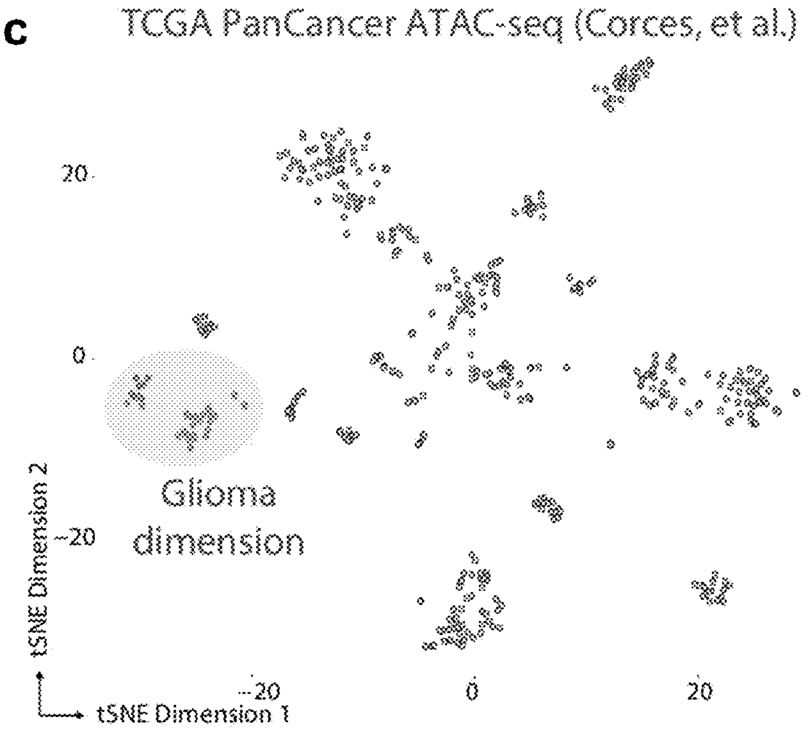
FIG. 14: Heterogeneous Mesenchymal trans-differentiation revealed by sLCRs in vivo—expanded.
Figure 14:
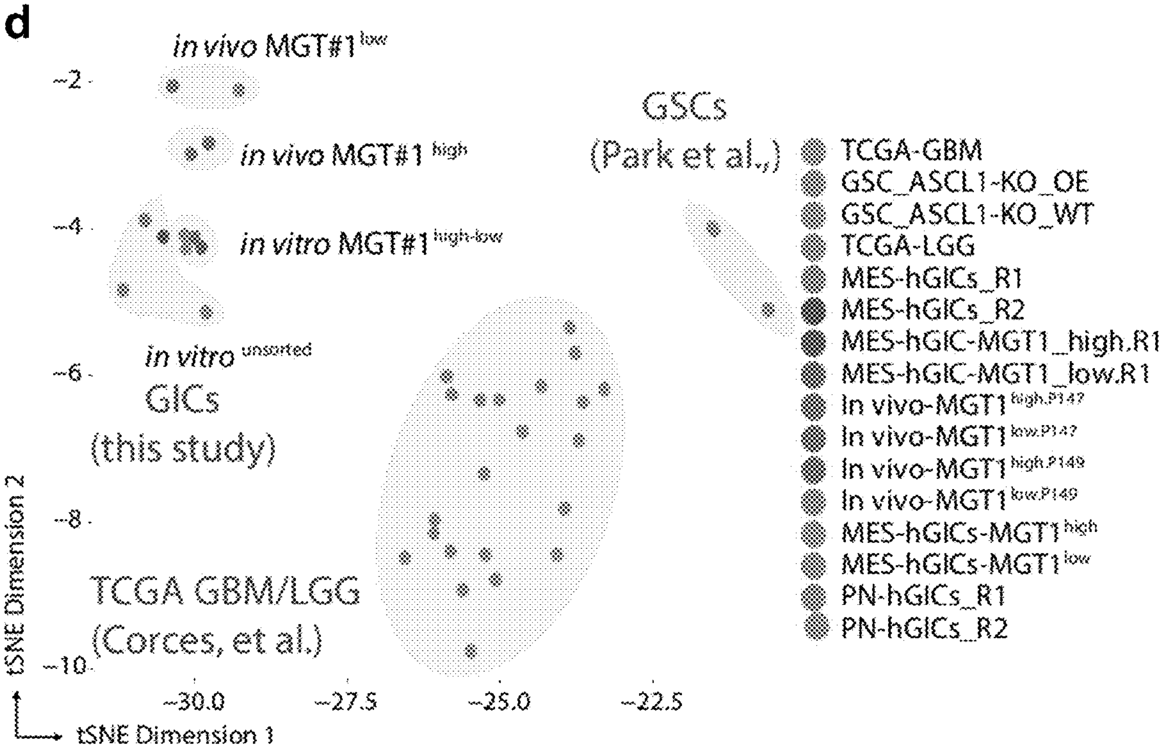

FIG. 14: Heterogeneous Mesenchymal trans-differentiation revealed by sLCRs in vivo. a) Scatter plot of ATAC-seq profiles for the indicated conditions, denoted by yellow and blue boxes in 5e). Open chromatin at TNF-receptor superfamily (TNFRS) loci is highlighted. b) UCSC genome browser view of the FADD/TNFRS6 locus. Changes in accessibility between in vitro and in vivo MGT #$1^{high}$ cells are denoted by arrows and colors (red-up, grey-neutral). c) Unsupervised t-SNE for the ATAC-seq profiling of the PanCancer dataset and indicated conditions. Each dot represents a given sample or the merge of all technical replicates, when available. The analysis includes top principal components for the 250,000 most variable peaks across all samples. Grey dots are all TCGA cancer types but GBMs/LGGs, which are colored along with the glioma stem cells from (Park et al., 2017, Cell Stem Cell 21, 209-224 Aug. 3, 2017) and GICs from this study. The circle denotes the dimension occupied by the primary GBM/LGG and GICs/GSCs. d) Unsupervised t-SNE for the ATAC-seq profiling limited to the samples within the Glioma dimension.

Figure 15:
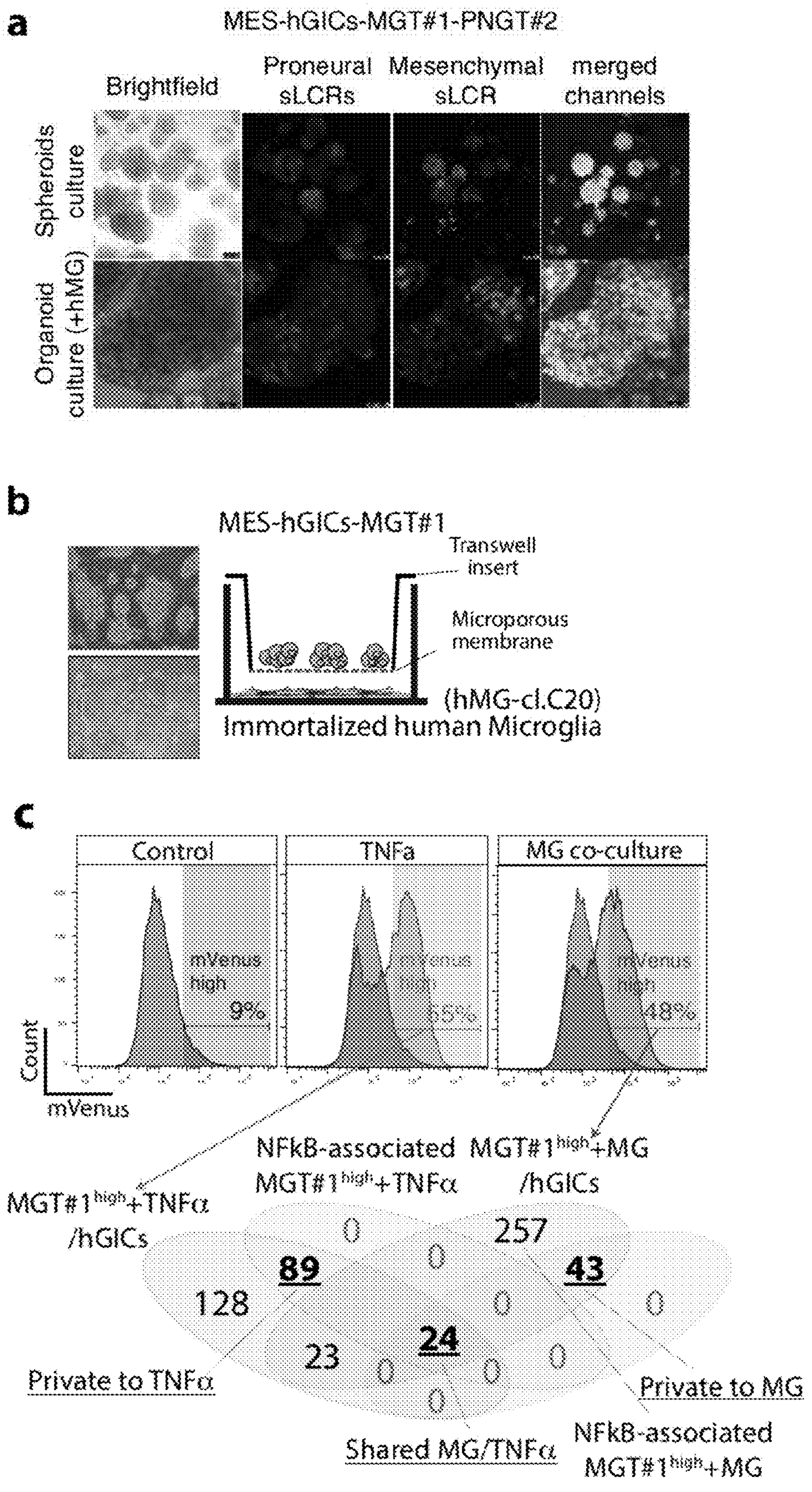
FIG. 15: sLCRs facilitate the discovery of therapeutic implications for non-cell autonomous crosstalk between tumor and immune cells.
Figure 15:
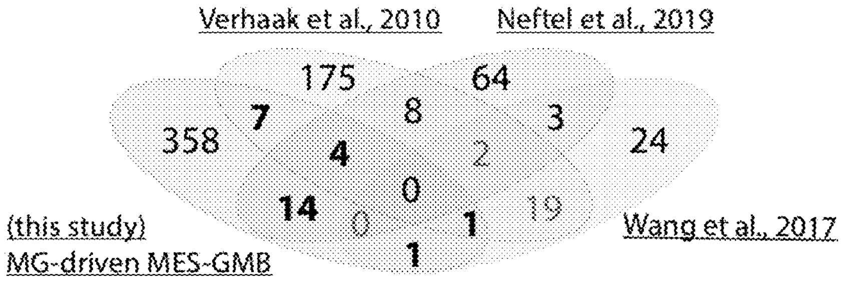
Figure 15:
Figure 15:
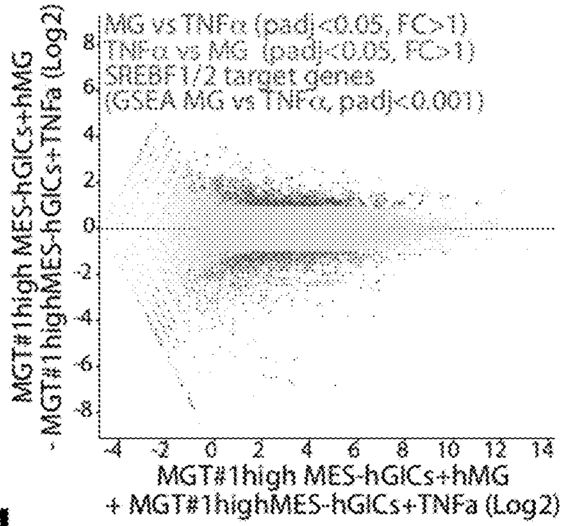
Figure 15:
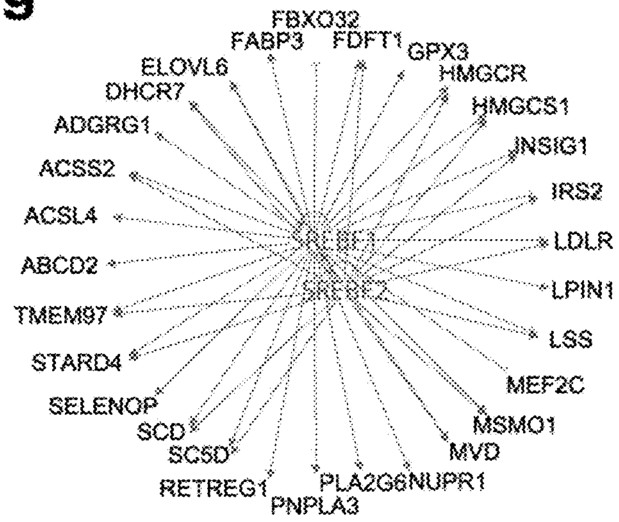
Figure 15:
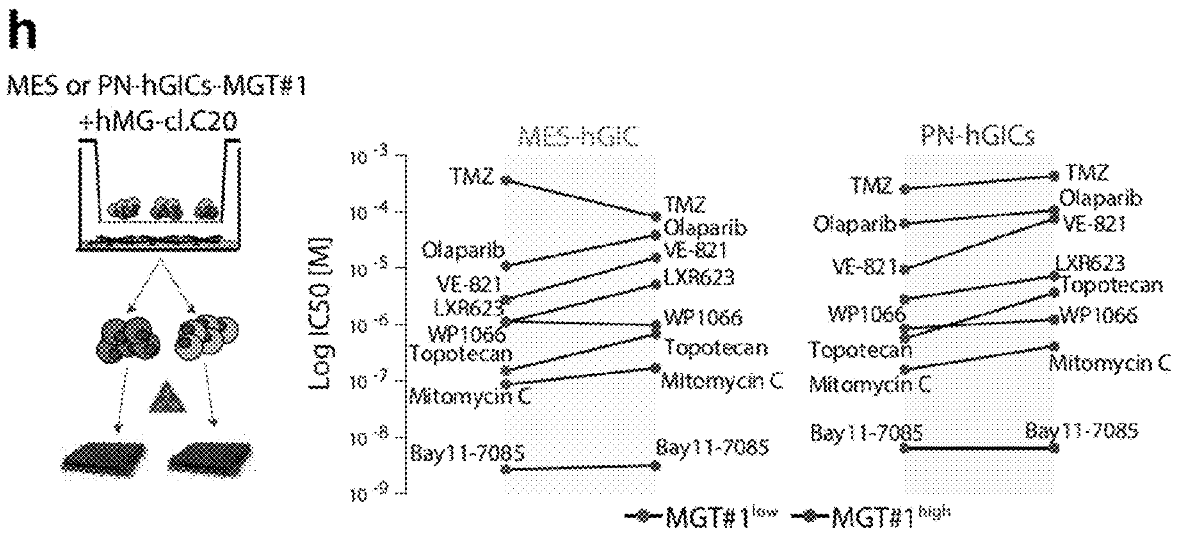

FIG. 15: sLCRs facilitate the discovery of therapeutic implications for non-cell autonomous crosstalk between tumor and immune cells. a) Bright-field view and IF of representative MES-hGICs with the indicated reporters propagated as spheroid or organoids with immortalized human Microglia (hMG; upper and lower panels, respectively). Scale bar=50 um. b) Schematic representation of contact-free hGICs-hMG co-culture. Left; Brightfield images of hGICs and MG in co-culture. c) Representative FACS profiles and gating strategy of MES-hGICs-MGT #$1^{high}$ alone or stimulated with TNFa or hMG co-culture. Below, Venn diagram of NFkB-related genes by Ingenuity Pathway Analysis of DRGs for the indicated conditions. DRGs are enriched compared to control GICs (FC>1, padj<0.05). d) Venn diagram of hMG-driven MES GBM signature overlap with patients' ones. Note the higher overlap with Neftel et al. compared to others. e) Heatmap of DRGs for the indicated conditions. RNA-seq reads were normalized as transcript per million, Log 2 transformed and Z-scored. Statistical significance was assessed by using R-package LIMMA (control, n=3, hMG, n=3; TNFa n=2; padj<0.05). f) MA plot for the indicated comparisons. Significant DRGs are highlighted and color-coded. g) Ingenuity Upstream Regulator Analysis of genes up-regulated by hMG co-culture compared to TNFa in MES-hGICs-MGT #$1^{high}$. h) Left, schematic depiction of chemosensitivity profiling assay for sLCR high and low states. Right, log IC50 values calculated for FACS-sorted MES-hGICs-MGT #$1^{high}$ and -MGT #$1^{low}$ fractions viability in response to increasing concentration of the indicated drugs.

Figure 16:
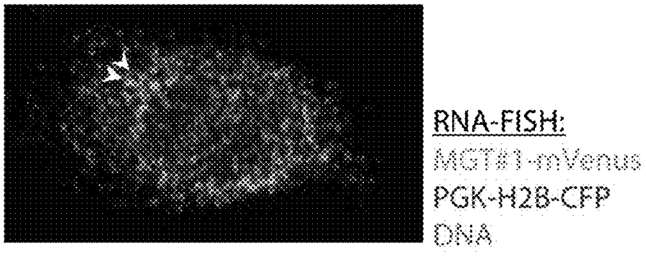
FIG. 16: Extended characterization of Synthetic Locus Control Regions (sLCR).

FIG. 16: Extended characterization of Synthetic Locus Control Regions (sLCR). Single-molecule RNA FISH quantification of MGT #1- and PGK-driven gene expression. Arrowheads/yellow denote cytoplasmic colocalization.

Figure 17:
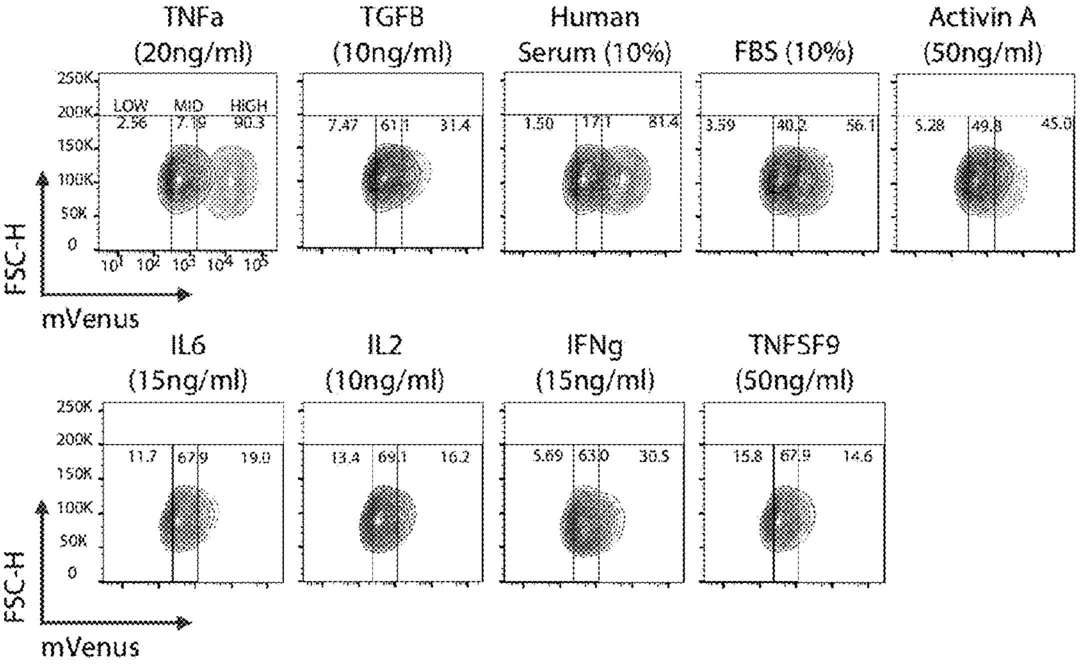
FIG. 17: Further examples of adaptive responses revealed by sLCR

FIG. 17: Further examples of adaptive responses revealed by sLCR. Representative MGT #1 activation upon the indicated stimuli.

Figure 18:
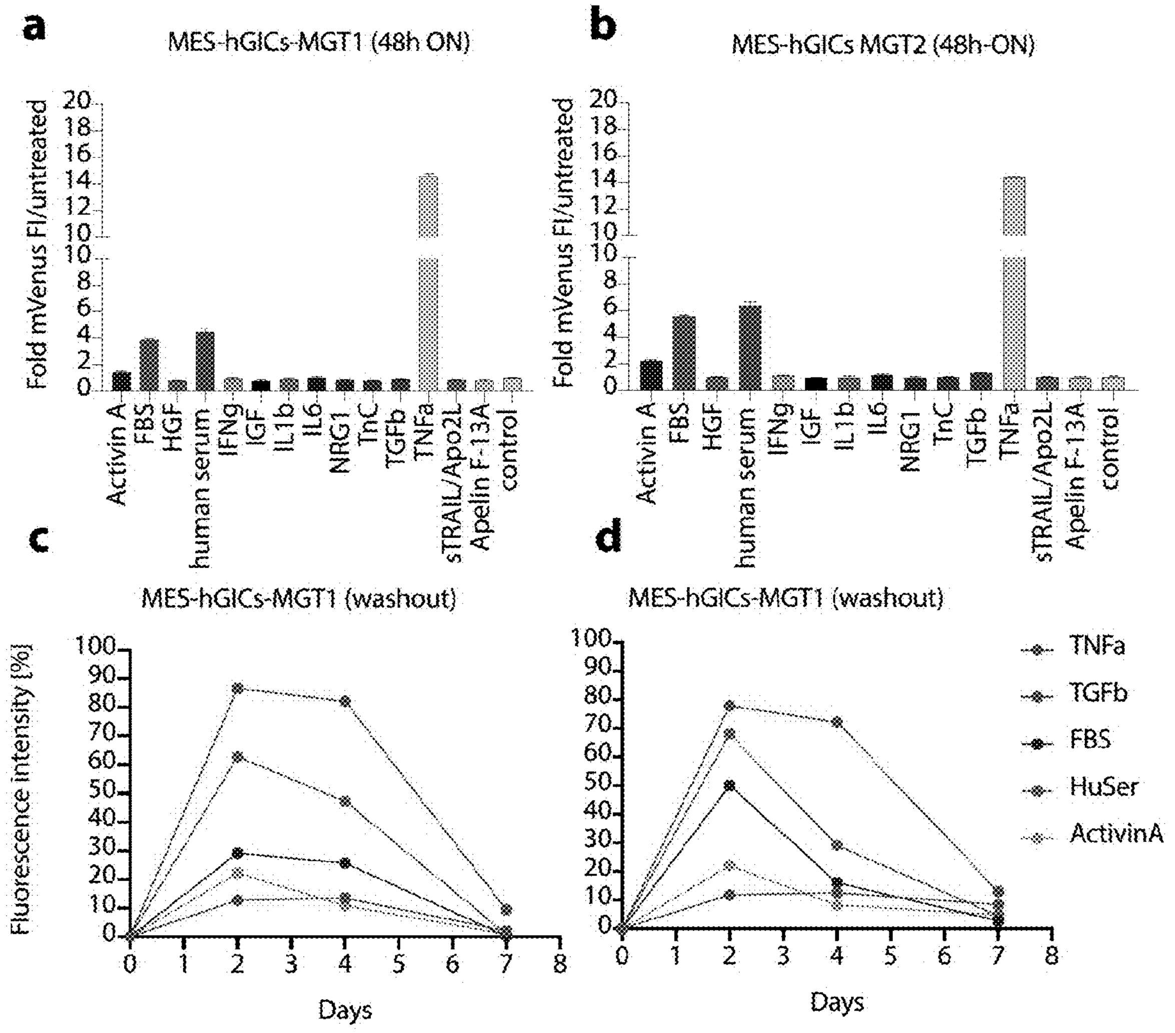
FIG. 18: The MES-GBM state induction measured by sLCRs in GICs is specific and reversible.

FIG. 18: The MES-GBM state induction measured by sLCRs in GICs is specific and reversible. a-b) Bar plot showing the individual response to the indicated factors/sLCRs after forty-eight hours of induction. c-d) Line plot showing the longitudinal expression of the indicated factors/sLCRs.

Figure 19:
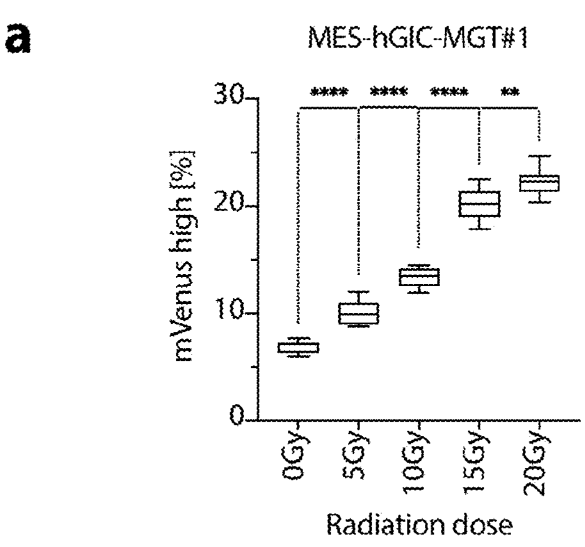
FIG. 19: MES-sLCRs to dissect the role for ionizing radiation and NFkB signaling in MES-GBM.
Figure 19:
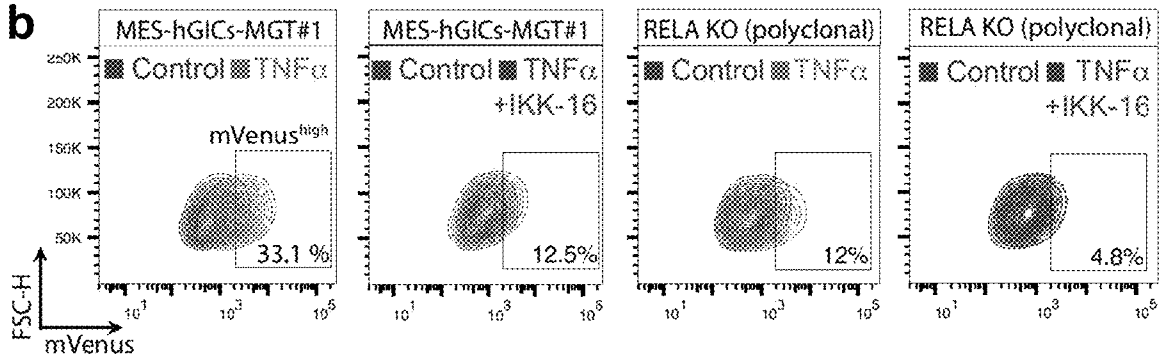

FIG. 19: MES-sLCRs to dissect the role for ionizing radiation and NFkB signaling in MES-GBM. a) Right, dose-response between IR and MGT #1 activation. An example of the experimental setting is shown to the left. b) Representative FACS quantification of Mesenchymal trans-differentiation upon the indicated stimuli.

Figure 20:
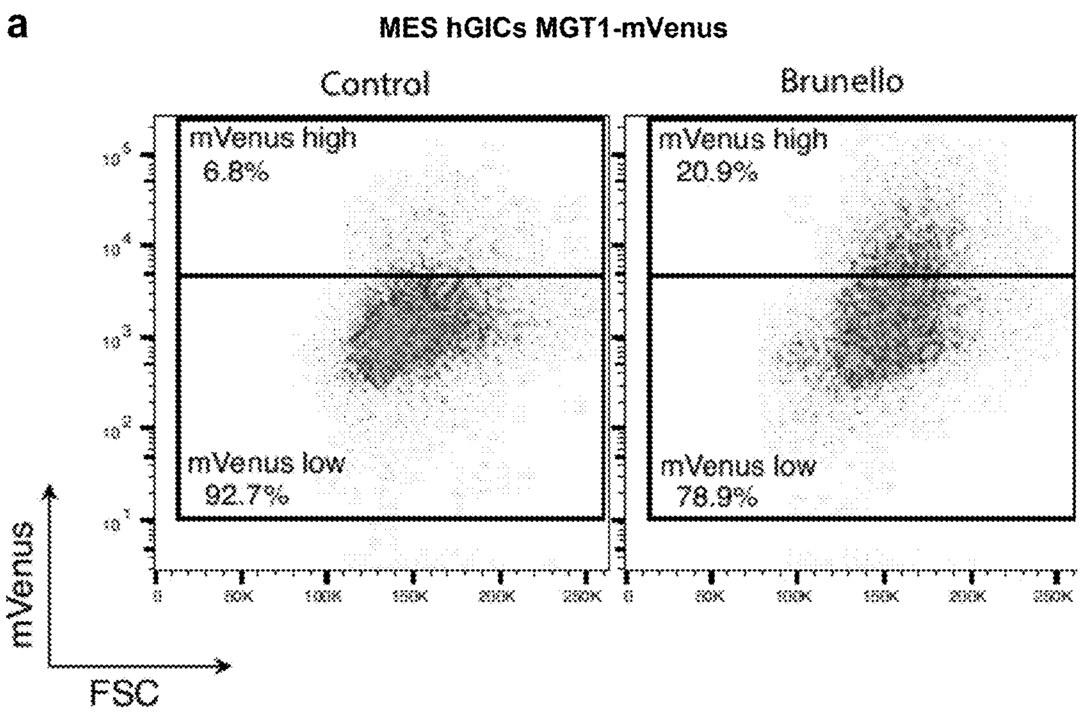
FIG. 20: Further evidence in support of sLCRs use in Phenotypic CRISPR/Cas9 forward genetic screens
Figure 20:
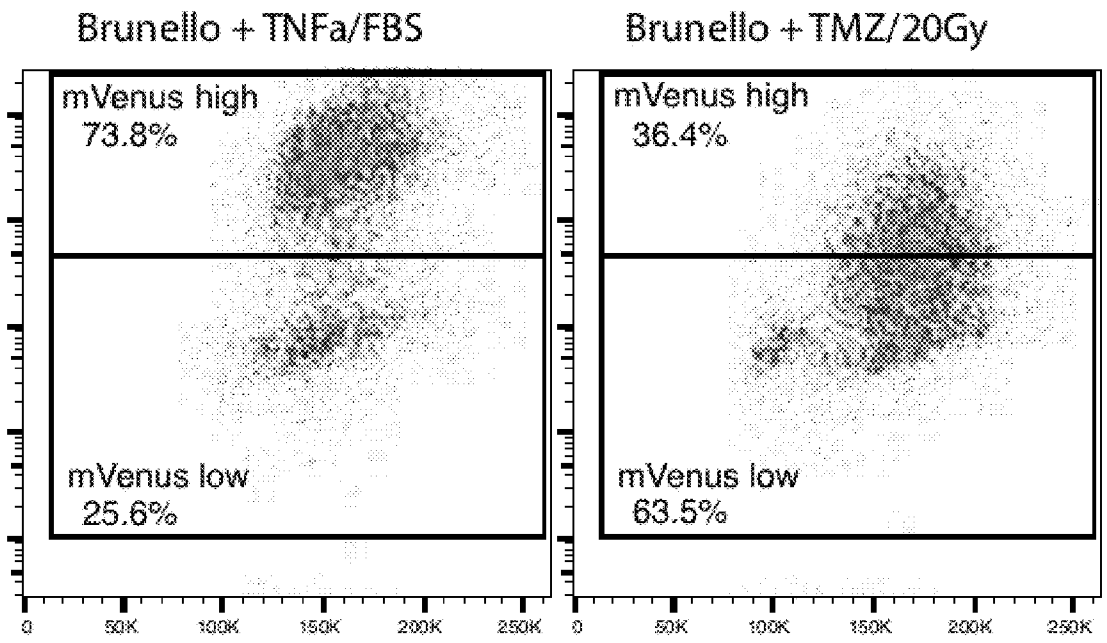
Figure 20:
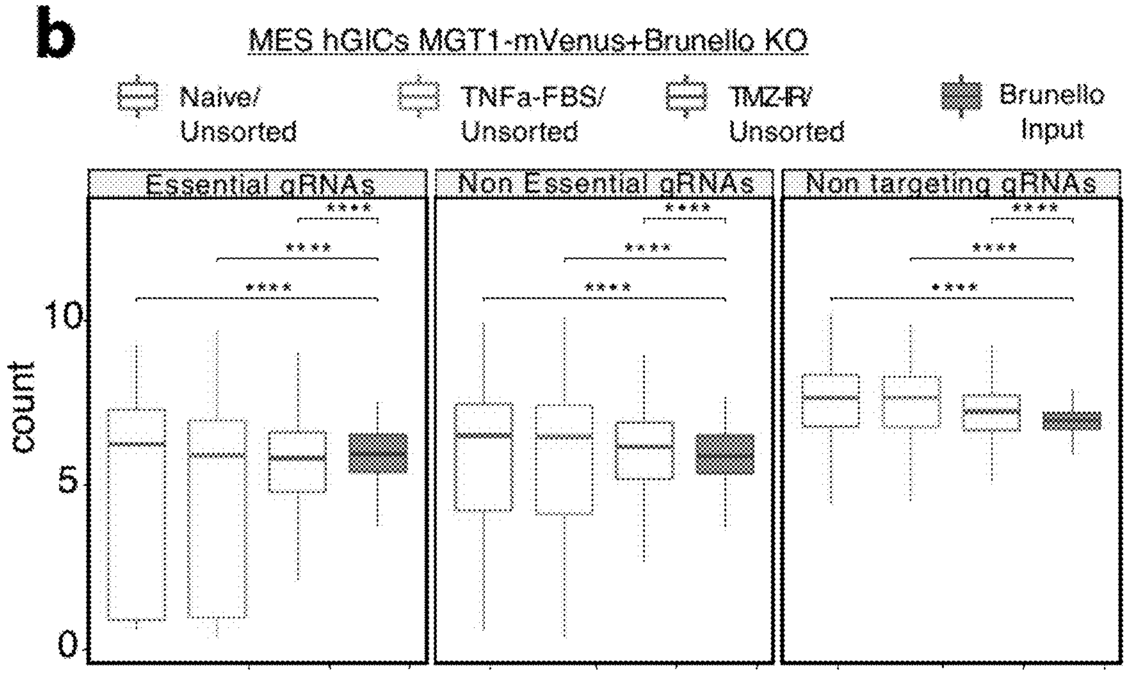
Figure 20:
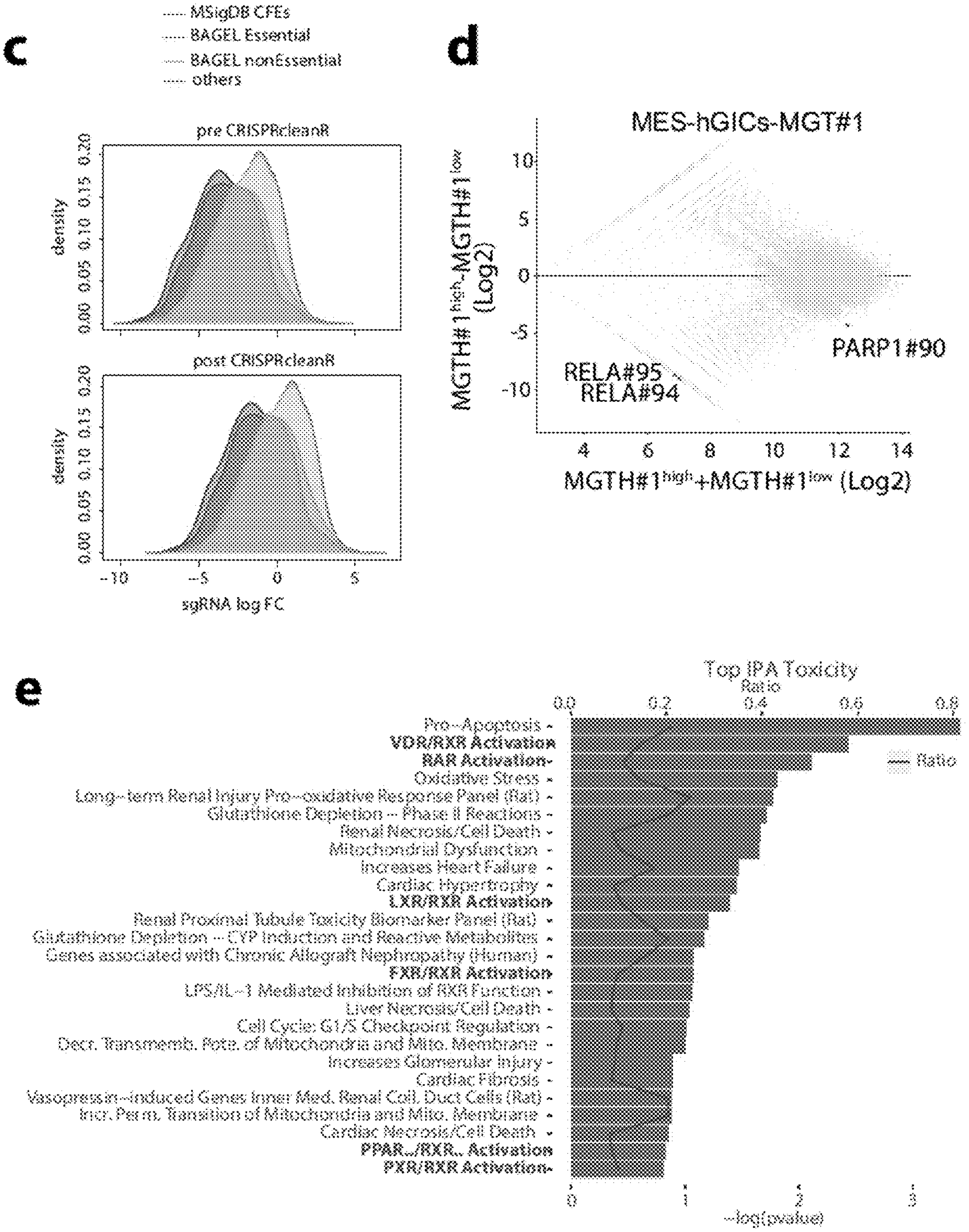
Figure 20:
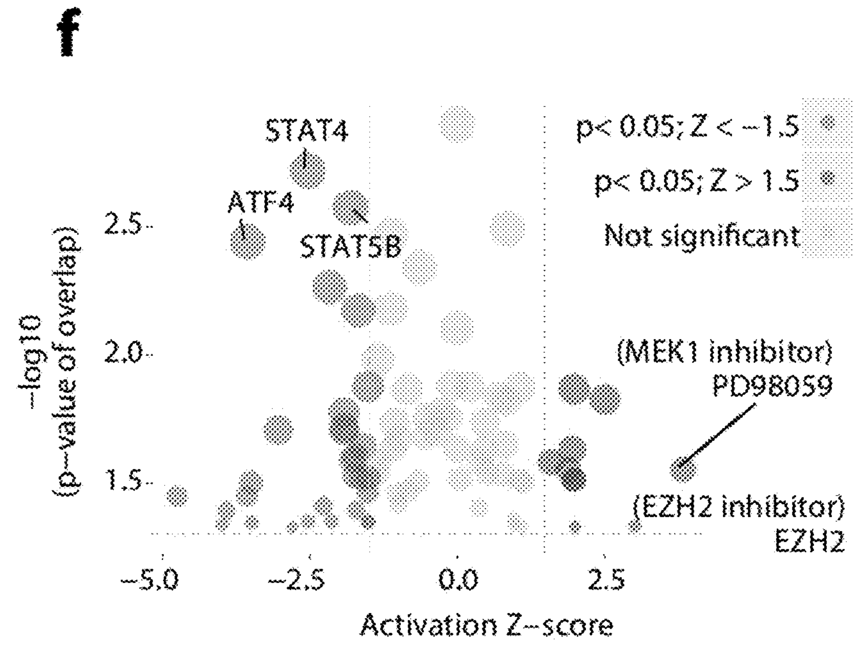

FIG. 20: Further evidence in support of sLCRs use in Phenotypic CRISPR/Cas9 forward genetic screens. a) From the genome-wide CRISPR-screen, FACS plots for indicated conditions before sorting MGT #1high and MGT #1low for gRNA amplification. b) Box plot showing data quality assessment by comparing the distribution of highly-informative essential and all non-essential or non-targeting gRNAs in the unsorted screen conditions (P value=Student's t-test). c) Distributions the sgRNA fold change values between Brunello library and unsorted MES-hGICs+Brunello conditions for the indicated gRNA sets (see Methods). d) Representative MA plot of sgRNA abundance (X-axis) and fold-change (Y-axis). Naive MES-hGICs carrying the Brunello library were FACS sorted in MGT #1high and MGT #1low and gRNAs normalized to the largest dataset and Log 2 converted (see methods). The indicated gRNAs are depleted compared to MGT #1high fraction. e) Ingenuity Pathway Analysis (IPA) Top 25 Toxicity categories of all hits from the CRISPR/Cas9 KO screen (FC±1.5; padj<0.05). Only "positive regulators" are beyond the statistical cut-off. In bold, categories associated with retinoic receptors signaling. IPA Upstream Regulator Analysis of all hits from the CRISPR/Cas9 KO screen (FC±1.5; padj<0.05). Positive and negative regulators of MES-GBM phenotype and significant categories without directional enrichment are depicted. f) Volcano plot of top regulated sgRNAs from the screen in e. Fold-changes for all MGT #1high fractions (n=3, naïve, average of TMZ+IR, TNFa+FBS) were calculated relative to all MGT #1low fractions and unsorted controls (n=6). Padj were calculated by DESeq2 and selected sgRNA-FDA approved compound-pairs are highlighted (see Methods).

Figure 21:
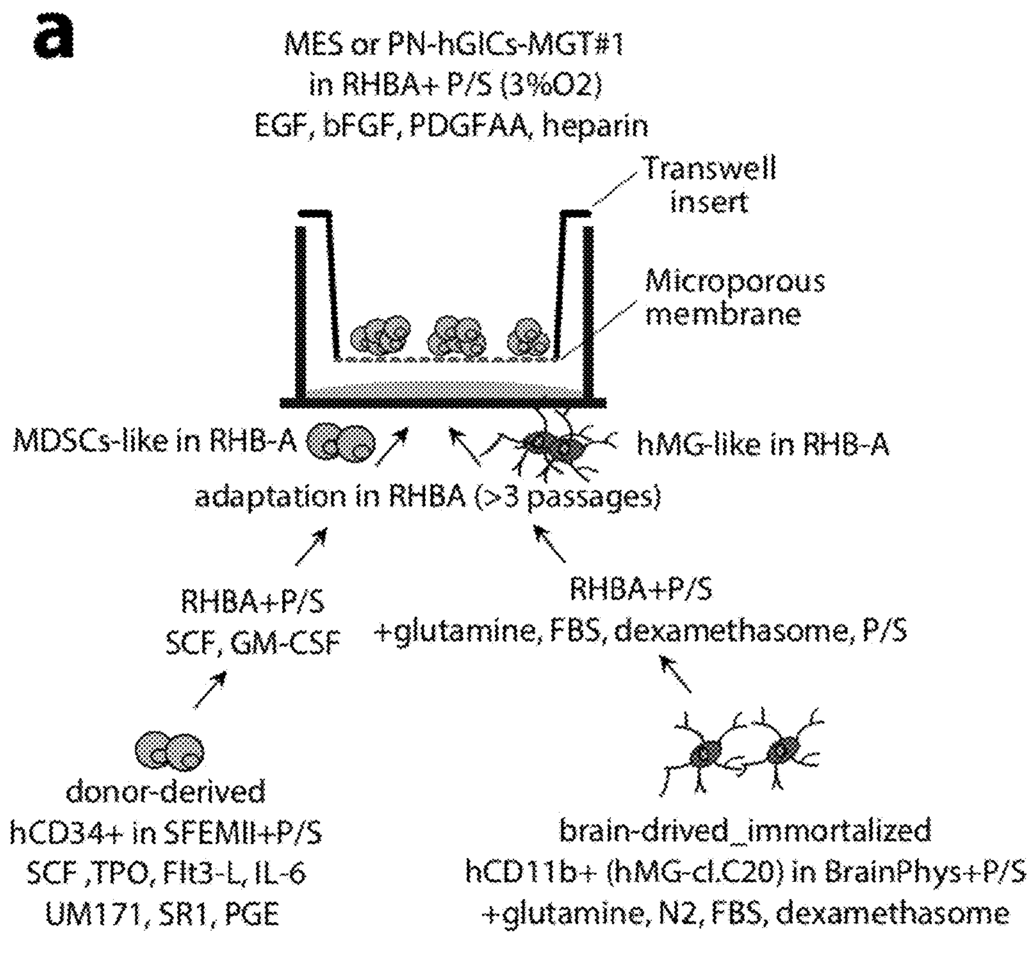
FIG. 21: Further evidence in support of hMG cells to induce MGT #1 expression in hGIC and differential sensitivity to therapeutics and hMG cells
Figure 21:
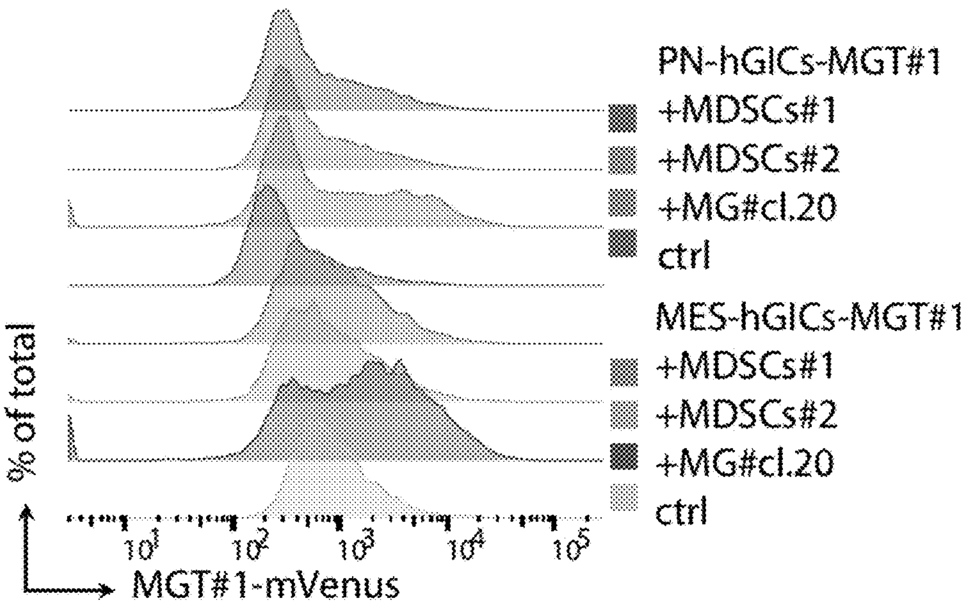
Figure 21:
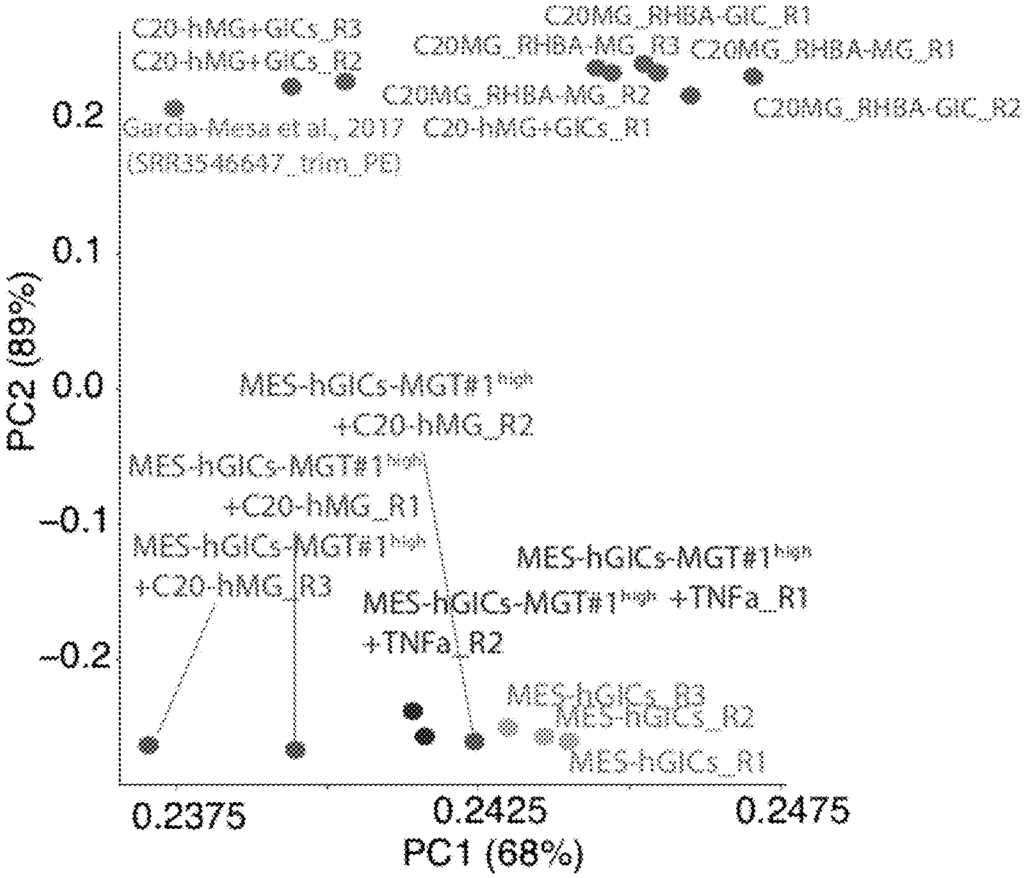
Figure 21:
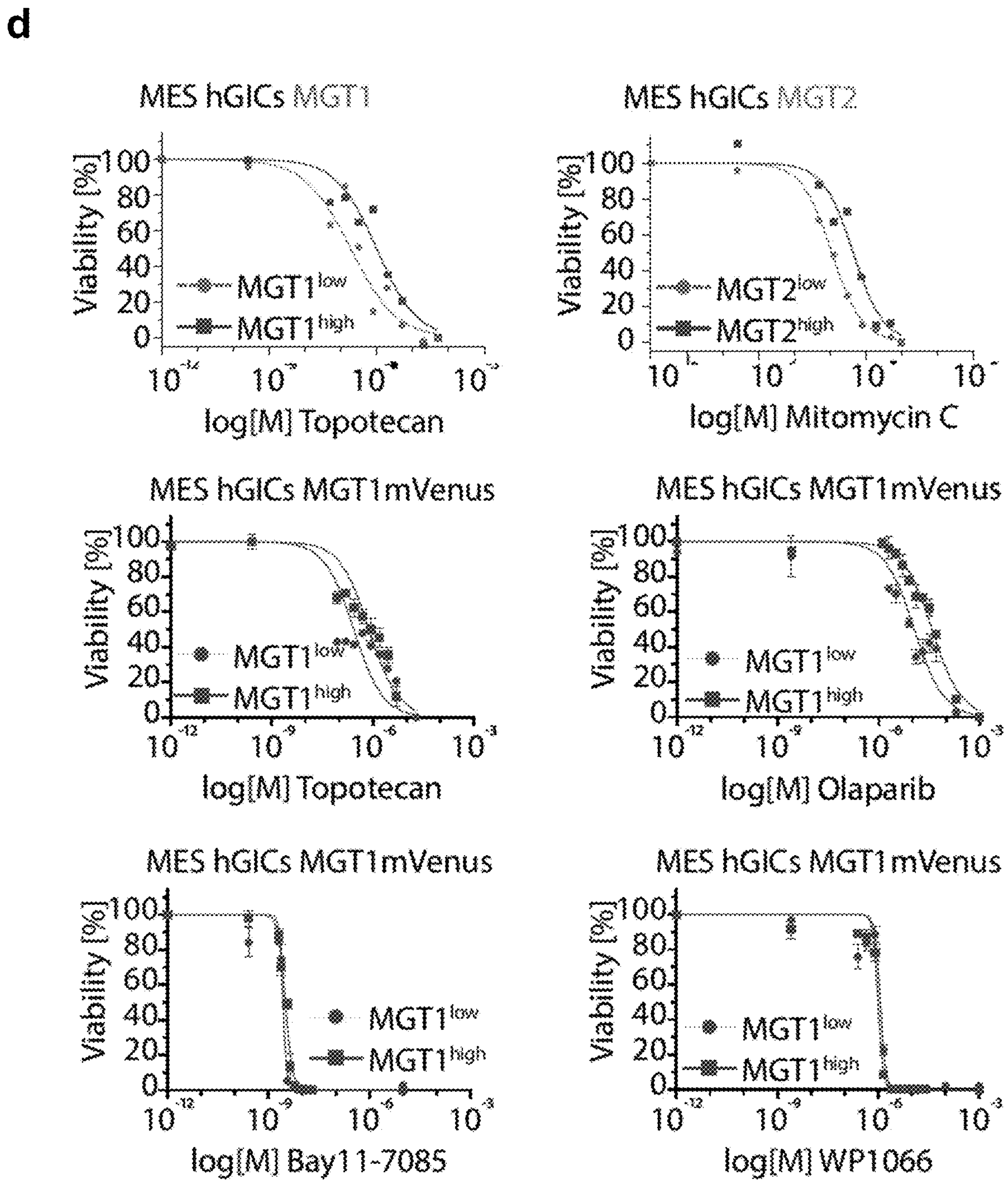
Figure 21:
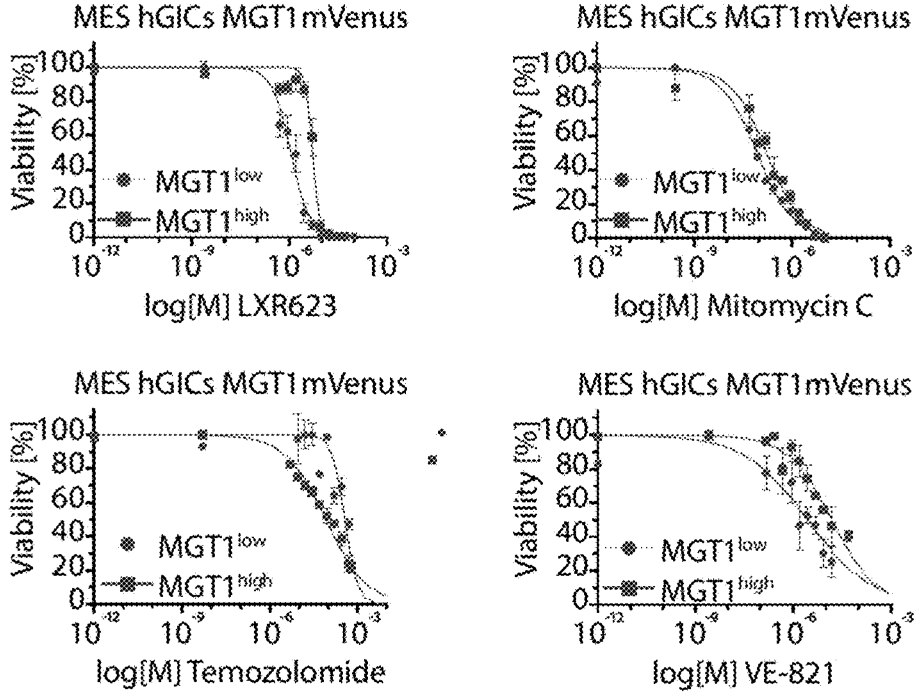
Figure 21:
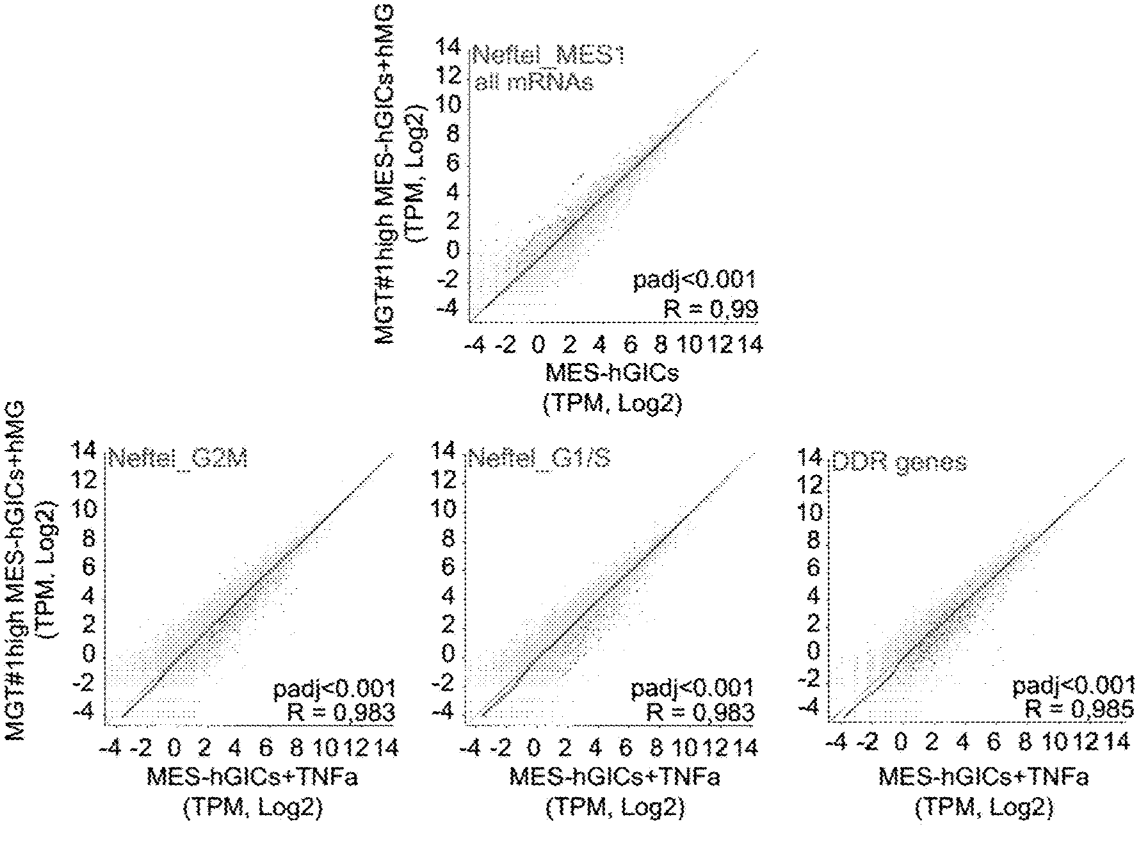
Figure 22:
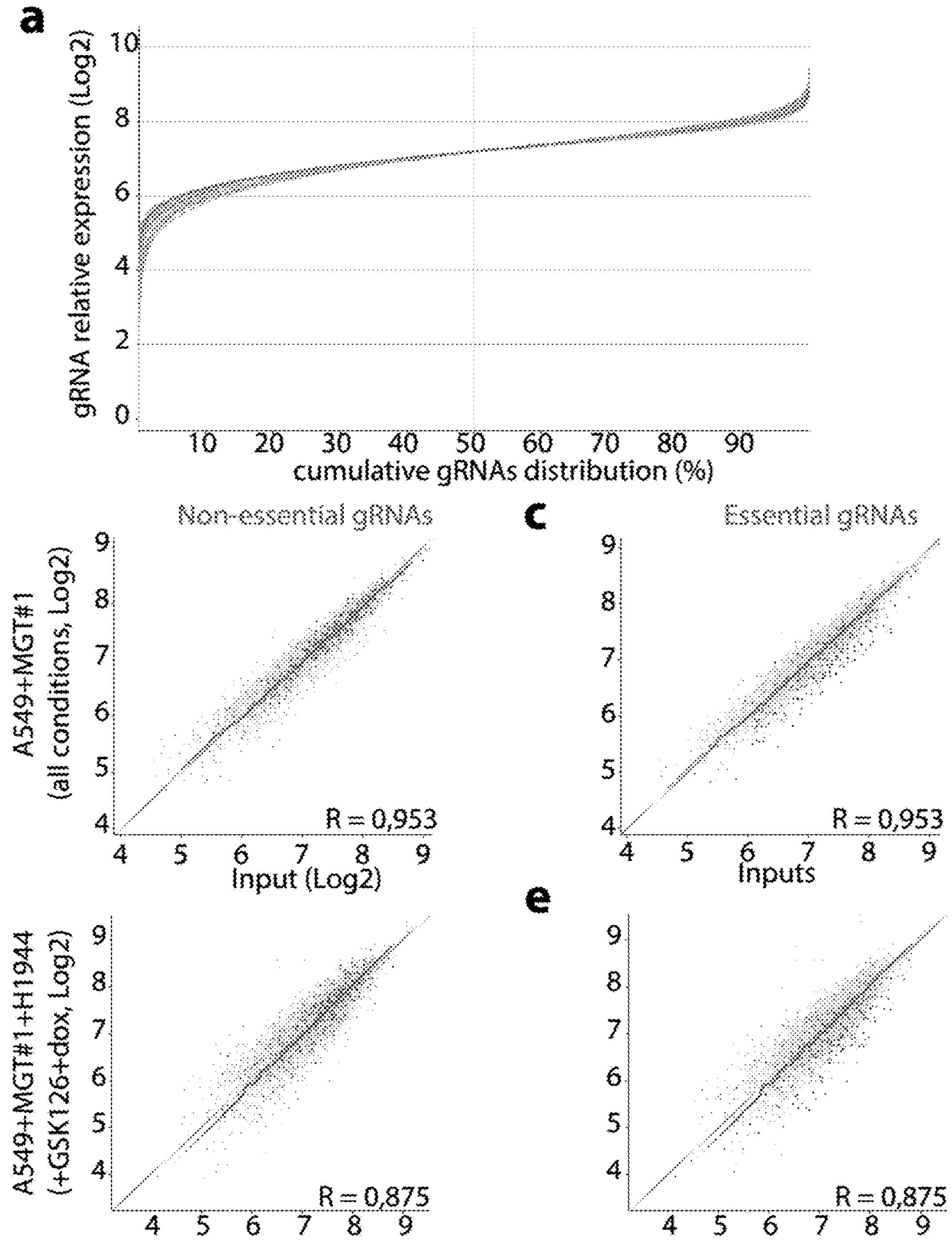
FIG. 22: Further evidence in support of sLCRs use in Phenotypic CRISPRi screens.

FIG. 21: Further evidence in support of hMG cells to induce MGT #1 expression in hGIC and differential sensitivity to therapeutics and hMG cells a) Extended schematic depiction of the co-culture experiment in FIG. 4; For detailed media composition see Methods. b) FACS profiles of MES- or PN-hGICs-MGT #$1^{high}$ alone or co-cultured with human microglia (hMG) or human CD34+-derived Myeloid-derived suppressor cells (MDSCs). c) Principal component analysis of the indicated RNA-seq profiles. Distances were calculated based on the average expression level of selected human MG markers obtained from Gosselin et al 2017. d) FACS-sorted MES-hGICs-MGT #1 high and -MGT #1low fractions viability in response to increasing concentration of the indicated drugs. e) Scatter plot and Gene Set Enrichment Analysis (GSEA) for the indicated gene lists showing that hMG cells induce MES-GBM and depress DNA damage transcriptional signature genes FIG. 22: Further evidence in support of sLCRs use in Phenotypic CRISPRI screens. a) Cumulative plot distribution for all the samples in the kinome screen (n=42), including technical replica and biological conditions: plasmid library, A549-H1944 input, A549-H1944+GSK126 high, med, low—controls—A549-H1944+GSK126+ dox high, med, low and A549-H1944+ dox high, med, low—screens for GSK126-driven EMT and homeostatic EMT, respectively. All gRNAs (n=6615) were normalized by total count per million reads, log transformed by percentile normalization (75 percentile) and transformed by converting to z-scores. b-c) Scatter plot for all gRNAs (n=6615) in the screen in FIG. 3*c-f* and GSEA for non-essential sgRNAs (n=483) and essential genes (n=352), respectively. Depletion of essential genes is significant by t-test as well as Kolmogorov-Smirnov with FC<–1 and padj<0.001. d-e) Scatter plot for all gRNAs (n=6615) in the combined A549+H1944+GSK126+ dox screen and GSEA for non-essential sgRNAs (n=483) and essential genes (n=352), respectively. Depletion of essential genes is significant by t-test as well as Kolmogorov-Smirnov with FC<–0.5 and padj<0.001.

EXAMPLES

The invention is further described by the following examples. These are not intended to limit the scope of the invention but represent preferred embodiments provided for greater illustration of the invention described herein. The examples show that the methods and reporter vectors described herein allow for cell-type specific expression of reporter and effectors genes in various cell types of interest.

Materials and Methods Used in the Examples:

sLCRs generation and TFBS discovery: High-affinity, TF-binding sites in defined genomic regions (DRG loci; table X) were identified using FIMO (PMID: 21330290) with -output-pthresh 1e-4-no-qvalue. A database of 1,818 models representing known transcription factor binding preferences (position weight matrices, PWM) was generated from the literature (Portales-Casamar et al., 2010; Badis et al., 2009; Berger et al., 2008; Bucher, 1990; Jolma et al., 2010). PWMs were pre-selected based on subtype-specific TFs. Regions corresponding to DRGs were retrieved from the UCSC genome browser (hg19; Refseq table downloaded on Oct. 5, 2012) and scanned with windows of 150 bp and 50 bp steps (hereafter refer as cis-units). The scanned area surrounding each signature gene was delimited by two distal CTCF sites, positioned >10 kb away from the TSS or TES. Subtype-specific PWMs were mapped to the genomic regions using FIMO. PWMs best significantly over-represented regions (adj. p.value <0.01; multiple backgrounds). For each window, whenever multiple matches for the same PWM were identified, the p-value of the best match was considered as a proxy for the affinity of that TF over that region. Given a region, an overall score was calculated based on the sum of the best–log 10(p-value) for each PWM considered. Significantly over-represented regions (multiple backgrounds) were determined by comparing motifs/background (empirical p-value <0.01). TFBS pairwise correlation heatmaps in FIG. 1*a* used the top 500 regions in terms of the score defined above. Genomics coordinates vs TFBS correlation heatmaps, including the representative one in FIG. 1*a*, were generated with the top 100 scoring regions.

Automation of sLCRs generation: To focus on cell intrinsic gene signatures, in a pilot approach, we filtered out genes lowly expressed in GBM stem-like cells (GSCs) from our previous experiments whereas current implementations of the method involve focusing on a validated Glioma-intrinsic signature[20]. The first sLCRs were designed with manual selection of the top scoring cis-units based on PWM score and diversity. Also, the selection of the TSS-containing region was done manually. The automated sLCR generation is written in python (URL GitHub/GitLab). The script takes as input a list of TFs, PWM, and the phenotype gene signature. With these, it generates cis-units from the defined cis-regulatory regions (default parameters: 150 bp windows/50 bp steps). The selection of the best cis-units for any given a phenotype is generated by using an algorithm based on defined selection rules. The algorithm first generates the ranking and the selection of the best cis-unit by applying the following formula: [Sum of scores–log 10(pvalue)*diversity (number of different TFBS)]. Iteratively, it removes the TFBS included in the selected cis-units. In order to increase the chances of successful transcriptional firing, the algorithm ranks cis-units also based on 5' CAGE data. The ranked list is the output of the algorithm. The automated procedure returned overlapping results with the manual selection (FIG. 7). Heatmaps in FIG. 1*a-b* were generated using heatmap.2 function from gplots R package.

RNA-seq generation: RNA was extracted using Trizol (Invitrogen), precipitated using Isopropanol and purified using RNAClean XP beads. RNA-seq libraries generated for this study were constructed using the TruSeq Stranded Total RNA library prep kit. Beads-based approach was used for rRNA depletion (Ribo-Zero Gold; Illumina) and PCR amplification was performed as per the manufacturer's protocol. Final libraries were analyzed on Bioanalyzer or TapeStation and barcoded libraries were pooled and sequenced on an Illumina HiSeq2500 or HiSeq4000 platforms with either single-read 51 bp or paired-end 100-base protocols. Illumina adaptors were trimmed using from the raw reads with Cutadapt, and raw reads were aligned to the human genome (Hg19 or Hg38) with TopHat. HTSeq was used to assess the number of uniquely assigned reads for each gene; expression values were then normalized to $10^7$ total reads and log 2 transformed to obtain counts per millions (CPM).

Analysis: For the heatmap in FIG. 2*d*, we used Seqmonk v1.42, Briefly, BAM files were aligned to Hg38 using HISAT2 and transcript quantitated with RNA-Seq pipeline quantitation on transcripts counting reads over exons correcting for feature length. Graphical representation used quantitation, log transformation and alignment assumed opposing strand specific libraries, followed by by percentile normalization supplemented by matching distributions.

In FIG. 15*e*, data were analyzed using SeqMonk and reads were normalized by the standard analysis pipeline, applying DNA contamination correction and generating raw counts to perform DESeq2 differential analysis. The same pipeline with log transformation was used for visualization. Significance was determined using standard SeqMonk settings: p<0.05 after Benjamimi and Hochberg correction with the application of independent intensity filtering. Quantitation was done as above. NFKB-related genes in MG vs GICs and TNFa vs GICs were determined using IPA, MES GBM signatures were obtained by the respective publications and plots were generated using Venny. GSEA significance was determined for MES-GBM FC>0.5 fold with padj=0, for PN FC<–0.4, padj=0 and for SREBP FC>1 fold with padj=0. FIG. 15*e* interaction map was generated using the function Ingenuity upstream regulator from IPA for the comparison MGT #1 High TNFa vs MGT #1 High C20MG co-culture.

ATAC-seq: ATAC-seq on FACS sorted populations was performed on 20-50,000 cells from the in vivo experiment, and 50-100,000 from the in vitro experiment. Cells were centrifuged in PBS and gently resuspend the pellet in 50 µl of master mix (25 µL 2×TD buffer, 2.5 µL transposase and 22.5 µL nuclease-free water, Nextera DNA Library Prep, Illumina), incubated 60 min, 37° C. with moderate shaking (500-800 rpm). Transposition was stopped by 5 µl of Proteinase K and 50 ul of AL buffer (Quiagen), incubated at 56 C for 10 min and DNA purified using 1.8× vol/vol AMPure XP beads and eluted in 18 ul. The optimal number of PCR cycles for library amplification was determined per each sample using 2 ul of template followed by qPCR amplification using heat activated Kappa Hifi polymerase and EvaGreen 1×. Final amplification was performed in 50 ul qPCR volume and 8-12 ul of template DNA. Primers were previously described (Buenrostro et al. 201). Libraries were individually quantified using Qubit (Life Technologies) and appropriate ladder distribution was determined on TapeStation (Agilent) using the High Sensitivity D1000 ScreenTapes. Sequencing was performed on an Illumina NextSeq 500 using V2 chemistry for 150 cycles (paired-end 75nt). ATAC-seq scatter analysis in FIG. 14*a* was performed using SeqMonk, by using as probes TSS±5 kb, final annotation on ENSEMBL mRNAs. Normalization used Read Count Quantitation and Reads were corrected for total count only in probes per million reads, log transformed snf further transformed by size factor normalization.

ATAC-seq analysis Reads were adapter removed using trim-galore v0.6.2-nextera, then mapped using bowtie2 v2.3.5 (reference) default parameters. ATAC-seq analysis was performed using SeqMonk, by using as probes TSS±5 kb final annotation on ENSEMBL mRNAs (2019 assembly). Counts were normalized using Read Count Quantitation function, and reads were corrected for total count only in probes per million reads, log transformed and further transformed by size factor normalization. Integration of sLCR ATAC-seq and TCGA ATAC-seq of FIG. 14*c* was generated according to established protocols.

Vector generation: The sLCRs were synthetized initially at IDT and later at GenScript. MGT #1-mVenus was cloned in the Pacl-BsrGl fragment of the Mammalian Expression, Lentiviral FUGW (gift from David Baltimore; Addgene #14883). Additional modifications, such as swapping of mVenus to mCherry, or MGT #1 with all other sLCR used either restriction enzyme digestion or Gibson cloning. The sLCRs vectors are 3rd gen lentiviral system and have been used together with pCMV-G (Addgene #8454), pRSV-REV (Addgene #12253) and pMDLG/pRRE (Addgene #12251). Sall2 (ccsbBroad304_11117) Pou3f2 (ccsb-Broad304_14774) were obtained from the CCSB-Broad Lentiviral Expression Library.

Cell lines: The MES-hGICs and PN-hGICs were generated by our lab and will be described elsewhere. Briefly, a PN-hGICs were generated by transforming human NPC, by means of: pLenti6.2/V5-IDH1-R132H, TP53R173H and TP53R273H (point mutations introduced into TP53 ccsb-Broad304_07088 from the CCSB-Broad Lentiviral Expression Library, and pRS-Puro-sh-PTEN(#1). MES-hGICs were generated by transforming human NPC pRSPURO-sh-PTEN(#1), pLKO.1-sh-TP53 (TRCN0000003754) and pRS-shNF1. For these lines, thorough genetic, transcriptional and epigenetic characterization has been performed, as well as in vivo tumor formation and phenotypic mimicking ability. In vitro, GICs were propagated as described[76] with one modification. In addition to with EGF (20 ng/ml; R&D), bFGF (20 ng/ml; R&D), heparin (1 μg/ml; Sigma) and 5% penicillin and streptomycin, PDGF-AA (20 ng/ml; R&D) is also supplemented to RHB-A (Takara). This medium composition will be referred to as RHB-A complete. hGICs were cultured at 37° C. in a 5% CO2, 3% O2 and 95% humidity incubator.

The T98G and U87MG (kindly provided by the van Tellingen lab, NKI) were propagated in EMEM medium. For the experiments in FIG. 13*a*, T98G were switched to RHB-A supplemented with EGF (20 ng ml-1), bFGF (20 ng ml-1), heparin (1 μg ml-1) and 5% penicillin and streptomycin and propagated first on standard tissue culture-treated plastic, then in ultra-low binding plastic (CORNING).

The MCF7, MDA-231, A549 and H1944, cell lines (kindly provided by the Rene Bernards lab, NKI) were cultured in RPMI medium. All cell lines were supplemented with 10% FBS, and 5% penicillin and streptomycin at 37° C. in a 5% CO2-95% air incubator.

Immortalized primary human Microglia C20 were cultured in RHB-A medium (Takara) supplemented with 1% FBS, 2.5 mM Glutamine (Thermofisher; 35050038), 1 μM Dexamethasone (Sigma; D1756) and 1% penicillin and streptomycin at 37° C. in a 5% CO2, 19% O2 and 95% humidity incubator.

Donor-derived CD34 cells were propagated in SFEM II (StemCell), SCF, FLT3-L, TPO, IL6 (all 100 ng/ml; easy-experiments.com), UM171 (Selleck, 0.035 μM), SR1 (Selleck, 0.75 μM), 19-deoxy-9-methylene-16,16-dimethyl PGE2 (Cayman, 10 μM).

Genome-wide CRISPR Knock-out in vitro screen: For the genome-wide pooled CRISPR Knock-out screen, we utilized the Brunello library consisting of 77,441 sgRNAs targeting 19,114 genes (average of 4 sgRNAs per gene) and 1000 non-targeting controls. To achieve a library representation over 100×, we transduced a total of $16\times10^6$ MES-hGICs-MGT #$1^{low}$ cells at a MOI of ~0.5 and amplified the cells for 10 days prior introducing the treatment. At day 10, the cells were either treated with TNFa (10 ng/ml) and FBS (0.5%); Temozolomide (50 μM) and Irradiation (20 Gy) or left untreated. Before the gDNA extraction, we performed a FACs sorting of each condition, collecting the MES-hGICs-MGT #$1^{low}$, MES-hGICs-MGT #$1^{high}$ and the unsorted populations. The genomic DNA was extracted by lysing the cell pellets for 10' at 56° C. in AL buffer (Qiagen), supplemented with Proteinase K (Invitrogen) and RNAse A (Thermo Scientific), subsequently purified with AMPure beads and eluted in EB buffer (Qiagen). NGS libraries were constructed in a two-step PCR setup, where the PCR1 is used to amplify the sgRNA scaffold and insert a stagger sequence to increase library complexity across the flow cell, while the PCR2 introduced Illumina compatible adaptors with unique P7 barcodes, allowing sample multiplexity. For the PCR1, 5 μg of each gDNA sample were divided over 5 parallel reactions, that were subsequently pooled together and purified using AMPure beads. The optimal cycle numbers for PCR2 were determined for 1 μl of each PCR1 individually by conducting a qPCR amplification using KAPA HiFi HotStart Ready Mix (Roche) and 1× EvaGreen (Biotium). 10 μl of the purified PCR1 of each sample were used as input for the final PCR2. Both PCR1 and PCR2 were performed using KAPA HiFi HotStart Ready Mix. Primers are available upon request. Quality control of the final libraries was performed using the Qubit dsDNA HS kit (Invitrogen) for quantification and TapeStation High Sensitivity D1000 ScreenTapes (Agilent) for determination of PCR fragment size. The barcoded libraries were pooled together in equal molarities and sequenced on an Illumina NextSeq500 using the 75 cycles V2 chemistry (1×75 nt single read mode).

Transwell co-culture: Co-cultures of hGICs and immortalized primary human Microglia C20 were set up using hydrophilic PTFE 6-well cell culture inserts with a pore size of 0.4 μm (Merck). Human Microglia were seeded at 1.5×105 cells/well for 24 h on 6-well plates in respective medium. Medium was aspirated and cells were washed once with PBS before 1 ml of RHB-A complete medium was added. Transwell inserts were placed into plates and 5×105 single hGICs in a total volume of 1 ml of RHB-A complete medium were plated on insert surface. hGICs and C20 human Microglia were harvested after 48 h of co-culture for further analysis.

Transfection-Transduction: Transfection and transduction were previously described in detail. Briefly, 12 μg of DNA mix (lentivector, pCMV-G, pRSV-REV, pMDLG/pRRE were incubated with the FuGENE-DMEM/F12 mix for 15 min at RT, added to the antibiotic-free medium covering the 293T cells and the a first-tap of viral supernatant was collected at 40 h after transfection. Titer was assessed using Lenti-X p24 Rapid Titer Kit (Takara) according to the manufacturer's instructions. We applied viral particles to target cells in the appropriate complete medium supplemented with 2.5 μg/ml protamine sulfate. After 12-14 h of incubation with the viral supernatant, the medium was refreshed with the appropriate complete medium.

Preparation of cryosections: Tumorspheres were allowed to settle by gravity, fixed in fresh prepared formaldehyde in PBS (1.0%), which was blocked with 140 mM glycine 2M, rinsed with 30% sucrose, followed by addition of freezing medium (O. C. T/cryomold). Frozen block were obtained by dry ice freezing and stored at −80° C. until used. The blocks were cut with Leica CM 1950.

Immunohistochemistry: Tissues or tumorspheres were fixed in 4% PFA for 20'. Following fixation, dehydration was performed with increasing EtOH from 70% to 100%, Xylene and overnight Paraffin incubation. Paraffin-embedded samples (PES) were cut using a HM 355S microtome (Thermo Scientific). Hematoxylin/Eosin (HE) staining was performed with standard and slides images were acquired with an automated microscope (Keyence).

Immunofluorescence: At RT, cells were grown on coverslip or spheroids spinned down on glass followed by 4% paraformaldehyde, (PFA, 16005—Sigma Aldrich) in PBS for 10 min fixation, washed in PBS 5 min (3×), permeabilized with 0.5% triton X100 in PBS for 5 min, blocked 15 min with 4% BSA (3854.4 ROTH), stained with primary and secondary antibodies and 20 μm/ml Hoechst 33258 (16756-50, Cayman), and mounted onto glass slides using nail polish and Vectashield (H1000-Linaris). On paraffin-embedded tissues, we performed Deparaffinization and Citrate antigen retrieval with standard protocols. Permeabilization was performed with Triton 0,25% in PBS and—when appropriate—endogenous peroxidases were blocked with 3% H2O2 in water. Typically, we performed blocking with 5% normal goat serum (NGS). Primary antibodies were: anti-GFP (Anti-GFP ab6556, 1:000), anti-MED1 (Abcam ab64965 1:500), anti-Tubulin (BD T5168, 1:2000), and secondary antibodies were: A31573, A11055 and A31571 Alexa Fluor 647, A21206 Alexa Fluor 488, A31570 Alexa Fluor 555.

RNA FISH and dual FISH-IF: Cells were permeabilized in 70% ethanol (RNA FISH only) or with 0.5% triton X-100 (for dual IF-RNA FISH), washed in RNase-free PBS (1× (Life Technologies, AM9932), fixed with 10% Deionized Formamide (EMD Millipore, S4117) in 20% Stellaris RNA FISH Wash Buffer A (Biosearch Technologies, Inc., SMF-WA1-60) and RNase-free PBS, for 5 min at RT. IgK-MGT #1-mVenus and H2B-CFP were probed using SMF-1084-5 CAL Fluor® Red 635 and SMF-1063-5 Quasar® 570 custom Stellaris® FISH Probes (oligo sequence available upon request) in 10% Deionized Formamide 90% Stellaris RNA FISH Hybridization Buffer (Biosearch Technologies, SMF-HB1-10) at 31.5 μM in 100 μL transferred to the coverglass, hybridized at 37° C. in the dark. After 0/N incubation, slides were washed with RNase-free PBS 5 min (3×). If primary/secondary staining occurred, it was as described above.

Imaging: Microscopes used were Zeiss LSM800, Leica SP5-7-8, Nikon Spinning Disk. Confocal images in Figure S41 were acquired with a Leica SP5. mVenus fluorescence was acquired using Ex=488 nm, Em=535 nm and those in FIG. 1*d* were acquired using a Zeiss LSM800, using Ex=558 nm, Em=575 nm for mVenus-QUASAR570 and Ex=653, Em=668 for BRD4- or MEDI-AF647, respectively. For the H2B-CFP-QUASAR670 we used Ex=631, Em=670. Images were processed using ImageJ or Photoshop.

Phenotypic screening: Tumor cells were propagated as described above until the screening. Then we seeded 15'000/50 μl/well in 384 well plates (Corning), in Gibco FluoroBrite DMEM medium supplemented with the appropriate growth factors. Cells were dispensed as 50 μl suspension into each well using the SPARK20M Injector system (50 μl injection volume; 100 μl/s injection speed). For non-adherent cells (e.g. GICs), cells were further centrifuge at 1500 rpm for 1 h30 min at 37° C. Bottom reading fluorescence was scanned using a SPARM 20M TECAN plate reader at 37° C. in a 5% CO2-95% air (3% for GICs) in a humidified cassette, with the following settings for mVenus: Monochromator, Ex 505 nm±20 nm, Em 535 nm±7.5 nm, manual gain:198, flashes: 35, Integration time:40 μs. In independent replicas, cell viability was measured with 0.02% AlamarBlue solution in FluoroBrite medium with the following settings: Fluorescence Top reading. Monochromator, Ex 565 nm±10 nm, Em 592 nm±10 nm, manual gain: 88, flashes: 30, Integration time:40 μs.

DMSO-soluble compounds such as GSK126, were robotically aliquoted using a D300e, whereas cytokines were robotically aliquoted to each well using an Andrew pipetting robot (AndrewAlliance), using the following concentrations:

| Cytokine | Product Code | Stock | Working concentration |
|---|---|---|---|
| IL6 | 206-IL; R&D Systems | 100 μg/ml | 15 ng/ml |
| LPS | ALX-581; Enzo | 200x | 1x |
| TNFα | 210-TA; R&D Systems | 100 μg/ml | 20 ng/ml |
| TGFb | 240-B; R&D Systems | 35 μg/ml | 5 ng/ml |
| IFNg | 285-IF; R&D Systems | 100 μg/ml | 10 ng/ml |
| Tenascin C | MBS230239; Mybiosource | 100 μg/ml | 100 ng/ml |
| HGF | 294-HG; R&D Systems | 10 μg/ml | 10 ng/ml |
| IGF | 50356.100; Biomol | 2 μg/ml | 2 ng/ml |
| FBS | 10270106; Gibco | 100% | 10% |
| GSK126 | | 5 mM | 5 μM |
| CBD | | 10 mM | 4 μM |
| Activin A | BV-P1078; Enzo | 50 μg/ml | 50 ng/ml |
| NRG1 | 97642.10; Biomol | 16 μg/ml | 90 ng/ml |
| IL1b | CYT-094; Biotrend | 100 μg/ml | 10 ng/ml |

Data were imported in PRISM7 (GraphPad). Fluorescence intensity from control dead cells was subtracted as background from all values. Individual values were normalized to the mean of controls and represented as Fold change.

Drug dose-response screening: Transduced hGICs from transwell co-culture experiments were harvested into single cell suspension and sorted into mVenus high and low populations using a BD FACSAria III. Cells were counted and 7000 cells/50 μl/well were seeded onto 384-well black walled plates in RHB-A complete medium using the SPARK20M Injector system (50 μl injection volume; 100 μl/s injection speed). Drugs were typically dissolved as a 10 mM stock in DMSO and dispensed using the D300e compound printer (TECAN) for targeted dose-response with plate randomization and DMSO normalization. After 72 h of incubation, cell viability was measured after 2-6 h incubation with 10 μl of Cell-Titer-Blu (Promega) assay reagent with the following settings: Fluorescence top reading. Monochromator, Ex 565 nm±10 nm, Em 592 nm±10 nm, gain setting: optimal scanning, flashes: 30, Integration time: 40 μs. Data were imported in PRISM7 (GraphPad). Fluorescence intensities from empty wells was subtracted as background from all values. Concentrations were log 10-transformed into log[M] scale and individual values were normalized to the mean of untreated positive and SDS treated negative control conditions. Non-linear regression modelling (log(inhibitor) vs. normalized response—Variable slope) was used to derive dose-response curve and IC50 values.

| Drug | Stock conc. | highest conc. | lowest conc. | target conc. | levels | range | replica |
|---|---|---|---|---|---|---|---|
| Topotecan (sc-204919A) | 1 mM | 20.000 nM | 0.26 nM | 500 nM | 10 | 1 log | 3 |
| Olaparib (SEL-S1060) | 1 mM | 20.000 nM | 0.26 nM | 1 μM | 10 | 1 log | 3 |
| Bay11-7085 (B5681) | 1 mM | 10.000 nM | 0.26 nM | 6.1 nM | 10 | 0.5 log | 3 |
| WP1066 (S2796) | 10 mM | 100.000 nM | 2.6 nM | 2.5 μM | 10 | 1 log | 3 |
| WAY-242623 (PZ0257) | 10 mM | 100.000 nM | 2.6 nM | 100 μM | 10 | 1 log | 3 |
| Mitomycin C (sc-3514) | 1 mM | 10.000 nM | 0.26 nM | 500 nM | 10 | 1 log | 3 |
| Temozolomide (T2577) | 20 mM | 500.000 nM | 2.6 nM | 100 μM | 10 | 0.5 log | 3 |
| TAK733 (S2617) | 10 mM | 100.000 nM | 2.6 nM | 5 μM | 10 | 1 log | 3 |
| VE-821 (Cay17587) | 1 mM | 20.000 nM | 0.26 nM | 1000 nM | 10 | 1 log | 3 |
| Ku-60019 (Cay17502) | 1 mM | 20.000 nM | 0.26 nM | 1000 nM | 10 | 1 log | 3 |
| NU 7441 (Cay14881) | 1 mM | 20.000 nM | 0.26 nM | 1000 nM | 10 | 1 log | 3 |

Irradiation of hGICs: Irradiation was delivered using the XenX irradiator platform (XStrahl Life Sciences), equipped with a 225 kV X-ray tube for targeted irradiation. hGICs cultured in either 6-well plates or 96-well plates were placed in the focal plane of the beamline and exposed to irradiation for a specific time, depending on the target dosage, as calculated with an internal calculation software.

Generation of Matrigel organoids: To generate organoids with co-culture of C20 human Microglia and hGICs, growth-factor reduced and phenol-red free Matrigel (BD; 734-1101) droplets were used as an extracellular matrix support. Target cells were harvested and single cell suspensions with 1.5×105 of C20 human Microglia and 3.5×105 of hGICs in a volume of 500 μl were prepared. Using pre-cooled consumables and pipette tips, 30 μl of Matrigel, thawed on ice, was added to each well of cold 60-well Minitrays (Thermofisher; 439225). 5000 cells per droplet were injected using 5 μl of the prepared cell suspension into each organoid and mixed by pipetting. Droplets were cultured for up to 14 days at 37° C. in a 5% CO2, 3% O2 and 95% humidity incubator and RHB-A complete medium was changed every 2-3 days. Live-cell imaging was performed on day 10 using a Leica SP8 confocal microscope.

RT-qPCR: cDNA was generated using SuperScript™ VILO™ MasterMix RNA (0.5-2.5 μg) in 20 μL incubated at 25° C. for 10', at 42° C. for 60' and at 85° C. for 5'. RT-qPCR was performed with 10 ng cDNA/well, in a 384w ViiA™ 7 System using 1× PowerUp SYBR Green Master Mix (Applied Biosystems), in 10μ/well. Primers are available upon request.

Tissue dissection and Cell surface staining: Brain tumor dissection was previously described in detail[77]. Briefly, the tissue was dissected with a scalpel, digested in Accutase/DNaseI (947 μl Accutase, 50 μl DNase I Buffer, 3 μl DNase I) at 37° C. until needed. Filtered through a 120 μm cell strainer first and a 40 μm cell strainer before RBC lysis (NH4Cl, 155 mM; KHCO3, 10 mM; EDTA, pH 7.4, 0.1 mM). After washing in cold PBS, viability and cell count were assessed automatically with 0.4% Trypan Blue staining using a TECAN SPARK20M.

When surface markers were assessed, typically, 200.000 cells/antibody were used in 15 ml Falcons. Staining volume was 50 μl in RHB-A medium with primary antibody (e.g. CD133-APC; Miltenyi), on ice, in the dark, for 30'. Unbound antibody was removed with two washes of PBS. Depending on whether cells were analyzed or sorted, data acquisition was performed on the BD LSRFortessa or cells were sorted using the BD Aria II or a Astrios Moflo. The appropriate laser-filter combinations were chosen depending on the fluorophores being analyzed. Typically, to remove dead cells, events were first gated on the basis of shape and granularity (FSC-SSC), and we used as viability dyes either AnnexinV or LIVE/DEAD Fixable Aqua Dead Cell Stain Kit (depending on the fluorophores being analyzed). Analysis was performed with FlowJo_V10.

FACS analysis: Analysis was performed with FlowJo_V10.

FACS sorting: Transduced hGICs were harvested into single cell suspensions and resuspended into cold RHB-A complete and filtered into FACS tubes. Sorting was conducted using BD FACSAria III or Fusion. The appropriate laser-filter combinations were chosen depending on the fluorophores being sorted for. Typically, to remove dead cells, events were first gated on the basis of shape and granularity (FSC-A vs. SSC-A) and doublets were excluded (FSC-A vs. FSC-H). Positive gates were established on PGK-driven and constitutively expressed H2B-CFP as sorting reporter, to sort for populations with low to medium intensity of sLCR-dependent fluorophore expression.

Immunoblot: Cell pellets were lysed in RIPA buffer (20 mM Tris-HCl pH7.5, 150 mM NaCl, 1 mM EDTA, 1 mM EGTA, 1% NP-40) supplemented with a 1× Protease inhibitor cocktail (Roche), 10 mM NaPPi, 10 mM NaF, and 1 mM Sodium orthovanadate. The lysates were sonicated if necessary, and electrophoresis was performed using NuPAGE Bis-Tris precast gels (Life Technologies) in NuPAGE MOPS SDS Running Buffer (50 mM MOPS, 50 mM Tris Base, 0.1% SDS, 1 mM EDTA). Protein was transferred onto Nitrocellulose membranes in transfer buffer (25 mM Tris- HCl pH 7.5, 192 mM Glycine, 20% Methanol) at 120 mA for 1 h. Protein transfer was assessed through staining with Ponceau Red for 5 min, following two washes with TBS-T. Blocking of membranes was done for 1 h at room temperature with 5% BSA in PBS. Dilutions of primary antibodies were prepared in PBS+5% BSA and membranes were incubated over night at 4° C. Following three washes for 5 min with TBS-T, dilutions of appropriate HRP-coupled secondary antibodies were prepared in PBS+5% BSA and membranes were incubated for 45 min at room temperature. After washing three times for 5 min with TBS-T, ECL detection reagent (Sigma; RPN2209) was applied and membranes were exposed to ECL Hyperfilms (Sgima; GE28-9068-37) to detect chemoluminescent signals.

Antibodies:

| Target | Product code | Manufacturer |
|---|---|---|
| GFP | ab6556 | Abcam |
| Vinculin | | |
| p-Stat3 y705 | 9145L | Cell Signaling |
| Stat3 | sc-482x | Santa Cruz |
| p-NFKB p65 | 3033P | Cell Signaling |
| NFKB p65 | 86299 | Abcam |
| p-p38 t180 d3f9 | 45115 | Cell Signaling |
| p-p38 | 9211s | Millipore |
| Nestin | 611658 | BD Biosciences |
| p-yH2AX Ser 139 | 05-636 | Millipore |
| K27me3 | 07-449 | Millipore |
| H3 total | 1791 | Abcam |
| E-Cadherin | 31950 | Cell Signaling |
| Vimentin | 5741s | Cell Signaling |
| Goat Anti-Mouse IgG (H L) - HRP | 626520 | Invitrogen |
| Goat Anti-Rabbit IgG (H L) - HRP | G21234 | Invitrogen |

IncuCyte: IncuCyte automated longitudinal imaging was performed in 96 wells black walls plates (Greiner). 300,000 cells per plate were seeded to reach optimal confluence at the end of the experiment. GSK126 was aliquoted using a D300e, whereas TGFB1+2 were manually aliquoted to each well. Both were refreshed every second day. The last time-point was independently verified using a plate reader (BMC Clariostar).

CRISPRi screen: For the CRISPRi screens, A549-MGT #1±GSK126±Dox cells were sorted on an Astrios Moflo. We aimed at a library representation of 1000× (>6 million cells) in the 10% of the lowest (dim) and 10% of the highest (bright) cells within each population. The mid population was also sorted and included in the screen analysis, as control. Cells were lysed 10' at 56 C in AL+ProteinaseK buffer (Quiagen) followed by DNA extractionwas extracted using AMPure beads (Agencourt) and RNAse A treatment. PCR amplification and barcode-tagging of the CRISPRi libraries was done essentially as described, including PCR buffer composition[77]. For each sample, in PCR1, we used 20 ug of DNA divided over 10 parallel reactions, including from input controls, whereas the plasmid library needed 0.1 ng of DNA in PCR1. Parallel PCR1 reactions were mixed together and 5 ul were used as template for PCR2. We used Phusion Polymerase (NEB), GC buffer and 3% DMSO in both PCR1 and PCR2. Primers are available upon request.

Libraries concentrations were measured and barcoded libraries were pooled and sequenced on an Illumina HiSeq2500 sequencing. Reads were mapped to the in silico library with a custom script (available upon request) to generate read-counts, which were subsequently used as input for Seqmonk. We used a custom genome for Seqmonk analysis (available upon request), and samples were normalized to RPM and Log transformed to generate MA plots, whereas DEseq2 at padj<0.001 was ran on raw read counts. We ran 2 independent CRISPRi screens in A549 and one additional screen in H1944.

CRISPR/Cas9 KO: A549-MGT #1 were knocked-out for CNKSR2 and ARID1A using a Cas9 RNP Synthego kit following instructions. Electroporation was performed using a BioRad XCell in PBS and using the standard pulse for A549 cells. Optimal gRNAs from the kit were first assessed using T7E1 as well as TIDE calculation (tide.nki.nl/). After that, we performed bulk assessment of MGT #1 fluorescence using flow cytometry as well as low confluence plating and manual cloning picking.

Animal experiments: All mouse studies were conducted in accordance with a protocol approved by the Institutional Animal Care and Use Committee and in agreement with regulations by the European Union. Orthotopic glioma xenograft studies were conducted as previously described[76] with modifications. NOD-SCID-IL2Rg/(NSG) mice were purchased from The Jackson Laboratory and maintained in specific-pathogen-free (SPF) conditions. We used male and female mice between 7-12 weeks of age.

Gene Knock-out: Gene knock-out were performed using Synthego Gene Knockout Kits. The sgRNAs were dissolved in nuclease free 1×Te buffer to a stock concentration of 30 uM. RNP complexes were formed by mixing the Cas9 nuclease-gRNAs in a ratio of 6:1. Each RNP complex was electroporated into 250K A549-MGT1 #1 in 2 mm cuvettes in 1×PBS using the Biorad GenePulser xCell (150 volts, 10 ms). After electroporation the cells were cultured in RPMI supplemented with 10% Fetal Bovine Serum and 1% of penicillin/streptomycin. Approximately 7 days after electroporation g DNA was extracted using the Invisorb spin tissue isolation kit (Stratec), eluted in 50 ul of elution buffer and PCR was performed on target genes of interest using 800 to 1200 bp products centered around the gRNA target loci (primers available upon request). Knock-out efficiency was calculated using TIDE (NKI) and T7E1 assays. Individual clones were established or bulk KO cells were directly assayed by FACS using a BD LSRFortessa and FlowJo program.

Example 1: Design of Expression Cassettes Comprising Subtype Specific Synthetic Locus Control Regions (sLCR) for Glioblastoma Multiforme (GBM) Tumor Cells A high degree of cellular and molecular heterogeneity is believed to contribute to resistance to standard therapy in solid tumors and it poses a hurdle to development of targeted approaches. Glioblastoma Multiforme (GBM) is the most common primary adult brain tumor, it is exceptionally heterogeneous and it is resistant to therapy[13]. GBM is also one of the cancers with the highest degree of genomic and epigenomic characterization[14-16]. Based on the transcriptome, GBM tumors were recurrently classified into three subtypes, with the Mesenchymal and Proneural being more often cross-validated[52,53,54]. Several studies debated on the correlation between subtype-specific gene expression signatures and differential response to therapy as well as overall survival of patients. This suggests that GBM subtype identities and fate changes may hold therapeutic potential. Within a GBM tumor, a predominant subtype and tumor cells with different subtype identities may coexist[17,18]. Moreover, tumors can change the dominant expression profile upon recurrence[19,20].

Lineage tracing previously had major impact in our understanding GBM biology in mouse models, informing on—among others—the cellular origin of individual subtypes[5], as well as on how aberrant homeostatic regulation may affect response to standard of care in vivo[10].

In the example, we describe a systems biology approach to design a synthetic system to genetically label any cell state or transition in complex developmental and disease settings and test this system in the quest for biological principles underlying the molecular subtypes of human GBM.

First, we assumed that subtype-specific GBM genes would substantially comprise the regulatory activity required to specific the subtype identity (i.e. cis-regulatory elements). We further assumed that the transcription factor genes (TFs) expressed in each subtype would be chiefly responsible for establishing and maintaining subtype identity.

To design a genetic cassette that would intercept the minimal signaling and regulatory information, we determined the subtype-specific GBM genes with the highest fold change compared to all other subtypes from TCGA datasets[16]. Calling MES, CL and PN subtype-specific genes can be achieved using an arbitrary stringent cut off (i.e. >6 Log 2 FC; FIG. 6). Likewise, TFs can be identified using a less stringent cut off (i.e. >0 Log 2 FC) and standard pathway analysis tools (e.g. Ingenuity Pathway Analysis, DAVID, etc.). Initially, genes lowly expressed in GBM stem-like cells (GSCs) from our previous experiments (e.g. <4 counts per million, CPM) were discarded as a measure to focus on cell autonomous regulation (FIG. 6). Current implementations of the method use single-cell RNA-seq profiles, as for instance the Glioma-intrinsic signature[14].

To identify genomic regions bearing high intrinsic cis-regulatory potential within the subtype differentially-regulated genes (DGRs), we computed all paired frequencies for best position weight matrix (PWM) associated with TFs expressed in each subtype (FIG. 1*a*). As cis-regulatory DNA are often nucleosome-free regions (NFRs; >147 bp) and involve on average ~1000 bp[21], to locate these elements precisely, we set a 1 kb sliding window approach, with 150 bp steps. The search for cis-units potentially regulating DRGs was delimited by two external CTCF binding sites as determined by the ENCODE consortium[22,23], with a distance from gene start/end arbitrarily set to >10 kb. These criteria approximate the functional definition of topological associated domains (TADs), which are believed to contain the vast majority of contacts among cis-regulatory elements for a given locus and use CTCF as a boundary protein[24].

To assemble a synthetic cis-regulatory element driving a subtype-specific expression using the above-described TFBS analysis, such synthetic Locus Control Regions (sLCRs) should ideally comprise the minimal set of cis-units with the highest number (i) and diversity (ii). Ideally, at least one cis-unit composing one sLCR would also include a natural transcriptional start site (TSS), and would be placed immediately upstream the reported element (FIG. 1*a*). With these criteria, we generated sLCRs for genetic tracing of MES, CL and PN GBM, hereafter MGT, CLGT and PNGT. An algorithm can be used to minimize the decision and automate the sLCRs generation (FIG. 7*a*). The pairwise correlation of TFBS potentially regulating these genes reveals that several TFs cluster together and away from other TFBS clusters (FIG. 1*b*). This observation is in agreement with experimental observations from ChIP-seq experiments, thereby indicating that our procedure returned results aligned with functionally and structurally relevant principles of genome regulation. Moreover, ENCODE ChIP-seq data in multiple cell lines, also support actual TFs binding to individual cis-units (FIG. 9). Importantly, distinct MGT #1 and MGT #2 sLCRs assembled by largely independent individual cis-units, and measuring as little as 827pb and 1015 bp in length respectively, can each represent up to the 60% of the overall regulatory potential.

Example 2: Genetic Tracing of Mesenchymal Fate in Human Glioma-Initiating Cells Using Lentiviral Vectors Comprising MGT #1 as sLCR A typical lentiviral vector carrying a sLCR such as MGT #1, drives the subtype-expression of fluorescent reporters mVenus or mCherry. To facilitate the genetic tracing in vivo, mVenus is driven to the plasma membrane (by Igk leader and platelet-derived growth factor receptor (PDGFR) transmembrane sequences tagging; FIG. 1*c*) and the mCherry is shuttled to the nucleus through a NLS. To enable fluorescent visualization and sorting of sLCRs independently from the reporter expression, we also included a second cassette expressing H2B-CFP fusion via the ubiquitous PGK promoter (FIG. 1*c*).

As a prototypical testing, we produced lentiviral particles in HEK293T cells with MGT #1-mVenus sLCR, and used viral particles to infect human Glioma-initiating cells with a MES genotype (MES-hGICs). Membranous mVenus expression was observed in both transient transfection as well as in stably transduced and cryosected tumorspheres (FIG. 1*d*).

Next, near-isogenic and characterized MES-hGICs and PN-hGICs were transduced with MGT #1 lentiviral particles. PN-hGICs bear a combination of IDH1 and TP53 point mutations, which is only found in PN GBM, whereas MES-hGICs have triple knockdown of TP53, PTEN and NF1, featuring a MES GBM background. Interestingly, we observed a minor but measurable increase in basal fluorescence in MES-hGICs, suggesting that MGT #1 reflects a basal higher intrinsic signaling in these cells (FIG. 1*e*). As TNFa is considered a prominent MES-GBM signaling pathway, and can induce a PN-to-MES transition[20], we next tested whether MGT #1 is faithfully reproducing a MES GBM signaling by exposing either MES-hGICs-MGT #$1^{low}$ and PN-hGICs-MGT #$1^{low}$ W to TNFα. In presence of TNF, at least two cis-units of the MGT #1 sLCR were previously showed to be directly engaged the TNF-driven NFkB TF. Reassuringly, TNFα induced a fluorescence increase in both cell types as compared to each parental control. Interestingly, notwithstanding a FACS sorting step ensuring that equal basal levels of MGT #1 expression were present in both cell types, MES-hGICs-MGT #$1^{low}$ turned into MES-hGICs-MGT #$1^{high}$ whereas PN-hGICs-MGT #$1^{low}$ only reached PN-hGICs-MGT #$1^{med}$ levels (FIG. 1*e-f*), validating the MGT #1 reporter for MES GBM subtype specific expression and exploiting this system to provide evidence for hGICs' adaptive responses to be engraved into their tumor genotype.

Human GICs and GSCs are consistently propagated under "NBE" conditions, which stands for serum-free Neurobasal media supplemented with basic FGF and EGF[25]. We further supplement our GICs with PDGF-AA, as this is the signaling pathway most often genetically amplified in GBM[26]. To investigate the ground state of MES-GBM signaling using our genetic strategy, we performed a medium-throughput cytokine screening in MES-hGICs-MGT #$1^{low}$ and PN-hGICs-MGT #$1^{low}$ cells. GICs were propagated under standard conditions and reseeded them into a 384-well format. Next, GICs were stimulated with individual cytokines in biological and technical replica followed by continuous fluorescence bottom reading in a pre-defined time course experiment. In a typical experiment, we longitudinally acquired MGT #1 fluorescence emission up to 48 hours from stimulation, and then we normalized the fluorescence to the naive GICs. In line with previous reports and above-mentioned experiments, MES-hGICs-MGT #1$^{low}$ turned into MES-hGICs-MGT #1$^{high}$ in presence of TNFα signaling (FIG. 2*a*, 8). Thus, MGT #1 informs on the differential response to external signaling between tumor cells with different genotypes. Moreover, MGT #1 is solid ground for a screening framework to identify relevant signaling for supporting MES-hGICs-MGT #1$^{low}$ and PN-hGICs-MGT #1$^{low}$ cells' growth and subtype identity.

Example 3: Use of MGT #1 and MGT #2 sLCRs as a Readout for Investigating Intrinsic and Adaptive Responses in GICs Under the same experimental conditions, a second independent reporter (MGT #2) showed consistent results (FIG. 2*a*), which supports our ability to generate a functional sLCR starting from a gene expression profile. Interestingly, both MGT #1 and MGT #2 reporters indicated that FBS is capable of inducing a Mesenchymal differentiation, which—unlike in the case of TNFα—was accompanied by GICs differentiation as gauged by visual inspection and flow cytometry (data not shown). This finding may be only in part explained by the presence of TGFB1, which is indeed a known component of FBS. In fact, TGFB1 is a Mesenchymal inducer but does not strongly induce MGT #1 not it promotes differentiation when used as purified cytokine within the same timeframe (FIG. 2*a*). Perhaps more interestingly, this observation on the FBS is highly consistent with the TCGA report that MES GBM signature cannot be find in any of the mouse brain cells but only in FBS cultured astroglial cells[16].

The in vivo source for TNFα in mouse models for Glioma is believed to be the tumor microenvironment (TME), notably glioblastoma-associated microglia/monocytes (GAMs) [27]. TNFα expression has been also observed in hGAMs[28]. Interestingly, IDH1-wild type GBM infiltration by GAMs was recently correlated with NF1 deficiency and a MEG GBM subtype identity[14]. To provide experimental support to the hypothesis GAMs recruited to GBM would drive a MES differentiation in NF-deficient GBM cells, we performed in vitro co-culture of IDH1-wild type and NF1-depleted MES-hGICs-MGT #1dim cells with MACS-purified CD11b cells purified from a patient with GBM. Strikingly, co-culture of hGICs-MGT #1dim cells with CD11b+ hGAMs induced MGT #1 expression in presence of IL-6 stimulation (FIG. 2*b*). IL-6 was previously shown to stimulate GAMs[29], and can be produced by either GSCs[30] or Mesenchymal stem cells from the TME[31]. Notably, hGAMs were insufficient to drive MGT #1 expression in MES-hGICs neither unstimulated nor when exposed to the TLR4 endogenous ligand Tenascin-C(TNC[32]), which is another GSCs-derived pro-inflammatory factor[33]. Moreover, TNFα drove MGT #1 induction in MES-hGICs regardless of the presence of hGAMs (FIG. 2*b*). Thus, our data uncover a potential cellular cross-talk in the GBM TME revolving around IL6 signaling and leading to the MES GBM specification. These data also highlight the potential for sLCR to mechanistically dissect non-cell autonomous interactions ex vivo.

Our data support sLCRs as a valid readout for investigating intrinsic and adaptive responses in GICs but do not exclude the possibility that this readout is largely restricted to the sole regulation of the reporter. To understand whether the reporter regulation is accompanied by a difference in cell identity, we performed immunoblotting, globlal gene expression profiling and targeted mRNA validation in MES-hGICs-MGT #1$^{low}$ and PN-hGICs-MGT #1$^{low}$ cells. Despite being propagated under the same experimental conditions, by all experimental means tested, MES-hGICs-MGT #1$^{low}$ and PN-hGICs-MGT #1$^{low}$ cells consistently showed a limited but measurable basal difference in signaling pathway activation and gene expression (FIG. 2*c-d-e-f*). Notably, while TNFα stimulation induced phosphorylation of NFkB-p65, STAT3 and p38-MAPK in both cell types this resulted in a markedly different gene expression output (FIG. 2 *c-d-e-f*). Thus, MGT #1 is informing on the impact of an active signaling (e.g. TNFα) and it does reflect similar cell fate transitions even when preexisting context-dependent differences are in place (e.g. a Mesenchymal signaling amplification or transition). Interestingly, both the global and the targeted gene expression profiling suggested that TNFα drives PN-hGICs to a state that is closer to MES-hGICs in their naïve state (FIG. 2 *c-d-e-f*).

Example 4: Use of MGT #1 to Functionally Test Whether Environmental Insults (e.g. Ionizing Radiations) May Induce Mesenchymal Transdifferentiation in GBM Cell Autonomous Manner Mesenchymal Differentiation in GBM was originally described as a dominant event at recurrence after radiotherapy[19] and later linked to acquired radio-resistance via TNF-driven NFKB activation[20]. Repeatedly, correlative evidences support a link between inflammatory signaling, EMT and radio-resistance[34]. To functionally test whether irradiation may induce Mesenchymal transdifferentiation in cell autonomous manner, MES-hGICs-MGT #1$^{low}$ and PN-hGICs-MGT #1$^{low}$ cells were exposed to Ionizing Radiation (IR), alone or in combination with TNFα. For this experiment, we revolved around delivering a single radiation dose of 10 Gy for two reasons: (i) we experimentally determined this to be sub lethal (alone and in combination with other treatments, including TNFα or Temozolomide; data not shown), and (ii) 10 Gy is close to the dosages experimentally proved to unleash secondary responses as a means of intrinsic radio-resistance as well as enhanced repair capacity in multiple human GSCs[34,35]. The residual DNA damage marker H2A phosphorylation twenty-four hours post irradiation confirmed the occurrence of both double-strand breaks and repair. However, only a minor proportion of GICs turned to a MGT #1$^{high}$ state from either genetic background (FIG. 2*g-h*). Rather, both MES-hGICs-MGT #1$^{low}$ and PN-hGICs-MGT #1$^{low}$ cells showed an augmented Mesenchymal differentiation in combination with TNFα, indicating that TNF signaling and IR cooperatively induce this cell fate specification. Taken together, these data support the conclusion that sub lethal IR cooperates with other mechanisms to drive a Mesenchymal transition in GBM. The data also support the speculation that NFKB activation is augmented as a result of non-canonical signaling caused by genotoxic stress[36].

Example 5: GBM Subtyping and Reprogramming Using sLCRs

The Proneural GBM is thought to represent the common GBM ancestor subtype and also to reflect an oligodendrocytic cell-of-origin 26,37. Previous studies revealed that longstanding propagation in FBS affects the phenotypic identity of individual cell lines 25,16. To test whether a PN sLCR would mirror the Proneural state, we decided to induce reprogramming of a FBS-driven conventional cell line into a PN-GICs using the master TFs underlying the PN identity 38. To this end, we transduced either MGT #1 or PNGT #2 into the T98G cell line, which is characterized by TP53 mutations (portals.broadinstitute.org/ccle), which are more likely to be associated with a PN phenotype16. In line with the genotype-driven prediction, when switched from a FBS to a NBE propagation condition, T98 cells showed a basal expression of PNGT #2 but not of MGT #1 (FIG. 3*a*-*b*). Importantly, transient over-expression of SALL3, SOX2 and POU3F2 further enhanced PNGT #2 activation but it was neutral to MGT #1 expression (FIG. 3*b*). Of note, these set of experiments were conducted with a mCherry fluorescent protein carrying a nuclear localization signaling, thereby excluding that the fluorescent protein intensity (mCherry is brighter than m Venus), localization and stability (m Venus is transmembrane and stabilized) play a major role in the observed phenotypic transitions.

Overall, these experiments indicate that multiple intrinsic and external triggers known to play a critical role in GBM biology can be intercepted by an individual sLCRs in GBM cells using the systems and synthetic biology approach described herein.

Example 6: Dissecting Epithelial-to-Mesenchymal Transition in Breast and Lung Cancer Cells Using MGT #1

The Mesenchymal transdifferentiation is a physiologic process hijacked by multiple tumors of epithelial origin[39]. To investigate whether our genetic tracing strategy extends beyond the GBM homeostasis, we next transduce MGT #1 into well characterized Epithelial and Mesenchymal breast cancer cells.

Tumor subtypes are genetically engraved in breast cancer cells[40]. Consistently, after a first round of lentiviral transduction, epithelial MCF7 cells showed lower MGT #1 expression compared to MDA-231 cells, which are believed to have undergone EMT (FIG. 10*a*-*b*). To confirm that MGT #1 expression reflects that actual breast cancer subtype identity, we FACS sorted and sub-cloned the top MCF7-MGT #1 and the mid MDA-231-MGT #1 expressing cells. Nevertheless, further propagation of the FACS-sorted populations reestablished pre-sorting homeostasis, with MCF7 expressing lower levels of MGT #1 than MDA-231. Such levels appeared to be stable, since short-term treatment with the EMT inducer TGFB2 did not strongly modify the basal MGT #1 fluorescence neither in MCF7 nor in MDA-231 (FIG. 4*a*).

Ezh2 inhibition can support Kras-driven EMT in several mouse and human lung cancer cells[41]. In this setting, we tested the use of sLCRs in reflecting cellular and molecular responses to biological and chemical stimuli. Consistent with previous findings, longitudinal measurement in epithelial A549 cells revealed that high MGT #1 fluorescence was cooperatively induced by the Ezh2 inhibitor GSK126 and TFGB signaling (FIG. 4*b*).

Epithelial lung cancer cells exposed to TGFB signaling readily changed their morphology as well as started expressing high levels of MGT #1 as gauged by flow cytometry (FIG. 11*a*-*b*). Interestingly, at an early time point, flow cytometry revealed that TFGB signaling and Ezh2 inhibition by GSK126 induces molecular transitions to a similar extent but GSK126 did not induce a cellular morphology changes. In a combination setting, TFGB signaling and GSK126 synergistically induce MGT #1 activation and an intermediate morphological change was also observed (FIG. 11*a*-*b*), raising the interesting possibility that GSK126 contributes to EMT through additional mechanisms other than as amplifier than TGFB signaling.

Example 7: Use of Ezh2 Inhibition and MGT #1 for Investigation of the Signaling and Genetic Basis of Epithelial-to-Mesenchymal Transitions in NSCLC Cells To exploit Ezh2 inhibition and MGT #1 as a framework to clarify the signaling basis of EMT in NSCLC cells, we next performed a cytokine screening in GSK126- and vehicle-treated A549-MGT $\#1^{low}$ cells. In keeping with above-mentioned data and our recently published observations (Serresi et al., J. Exp. Med, 2018, doi:10.1084/jem.20180801), TNFα proved to be the leading signaling towards MGT #1 expression also in epithelial lung cancer cells, with a modest additive effect of GSK126 to the overall high fluorescence output measured in a longitudinal medium-throughput microplate reader screening. Simultaneously, we confirmed that A549 cells respond to TLR stimulation via bacterial LPS differently when GSK126 is present and—also under these experimental conditions—we show that TGFB1 induces MGT #1 more substantially when combined with GSK126. The systematical analysis of the screening with several cytokines and their combinations reveals that Ezh2 inhibition enhances the transcriptional response to external signaling towards EMT (FIG. 12). Collectively, MGT #1 responses indicate that multiple signaling pathways may converge during EMT and suggests that transcriptional inhibition controls cellular metastability.

Next, we wished to exploit Ezh2 inhibition and MGT #1 as a framework for high-throughput screening to clarify the genetic basis of EMT in NSCLC cells. First, we transduced both A549 and H1944 Kras-driven NSCLC cells with the MGT #1 reporter. Subsequently, we introduced in both cell lines a Tet-inducible KRAB-dCas9 and a library of sgRNAs targeting the full complement of the human kinome (543 genes, 5,901 gRNAs in total; ~5 gRNAs/gene). Moreover, we also included essential and non-essential genes targeting gRNAs to serve as control for the screening procedure. This system allows the systematic knock-down of individual genes in individual cells (FIG. 4*c*). By applying GSK126 treatment as previously described, we FACS purified NSCLC cells which were either improved or impaired in their ability to support the expression of the fluorescent reporter and that showed an Epithelial or Mesenchymal phenotype (FIG. 4*d*-*e*). A gene set enrichment analysis supported the overall quality of the screen as gauged by essential but not non-essential genes being significantly depleted in both cell lines in vitro, as compared to the input populations (data not shown). By comparing A549-MGT $\#1^{low}$ and H1944-MGT $\#1^{low}$ to their MGT $\#1^{high}$ counterpart, we retrieved only a minor fraction of gRNAs that were statistically different enriched or depleted in either one of the two states in both cells lines (14/5912, 0.24%) indicating that most human kinases are dispensable for GSK126-driven EMT. However, two gRNAs were both statistically significant and showed high fold change association with A549-MGT $\#1^{low}$ and H1944-MGT $\#1^{low}$ cells indicating that their expression can lead to transcriptional repression of kinase-related genes enabling lung cancer cell EMT upon Ezh2 inhibition (FIG. 4*e*). Interestingly, one gRNA targets the ACVR1 receptor, which was previously reported to reinforce the NF-kB-driven EMT[42], and one gRNA targeting CNKSR2, a scaffold protein involved in RAS-dependent signaling, which was a non-obvious candidate for the control of EMT in lung cancer. We validated the results of the screen using conventional CRISPR/Cas9 technology, and two independent clones CNKSR2 KO clones showed enhanced epithelial features compared to the parental control, and similar to the ARIDIA KO which is expected to be required for Ezh2 loss-of-function phenotypes (FIG. 4*f*). RAS-driven EMT was previously shown to occur through the Hippo pathway[43]. Our data generated through the use of a sLCR potential uncover an additional mechanism that may directly contribute to EMT through the RAS/MAPK-dependent signaling.

Taken together, the results obtained with the Epithelial-Mesenchymal transition in three different cancer types underscore the tissue-independent ability of our sLCRs to reveal tumor such homeostates.

Example 6: MGT #1 as a Genetic Tracing Reporter for Tumor Homeostates In Vivo

Having demonstrated the utility of sLCRs in the dissection of cellular and molecular states ex vivo, we next wished to test the role for MGT #1 as a genetic tracing reporter for tumor homeostates in vivo. We intracranially transplanted MES-hGICs-MGT $\#1^{dim}$ cells into NSG mice and longitudinally monitored tumor formation. At the onset of neurological signs of high-grade disease stage, we sacrificed the animals and performed histochemical and immunohistochemical as well as endogenous and surface marker analyses. Histologically, all tumors appeared as grade IV GBM, with a large proportion of mouse brain infiltrated by malignant cells, indicating extensive proliferation and invasion (FIG. 5*a*). For each animal (n=10), we used imaging-guided tumor resection to generate single-cell preps while retaining the infiltrated brain tissue. Immunohistochemical staining revealed that MGT #1 expressing cells are non-randomly distributed in the tumor mass, but rather well confined within the invasive front (FIG. 5*a-b*).

Given that response to virus, chromatin modification and gene silencing may all potentially affect sLCR expression, to confirm that MGT #1 reflect functional intratumoral heterogeneity and rule out that the MGT #1 expressing cells are simply escapers, we used two approaches. First, we inspected all the dense areas in which MES GBM signaling was absent for expression of other markers as well as of the MGT #1-independent H2B-CFP. We confirmed that the vast majority of the stained tumor tissue was accessible to antigens in immunostaining by means of Tubulin staining and we confirmed that several MGT #1 "dark" cells in which active proliferation could be inferred by chromatin condensation were indeed H2B-CFP positive (FIG. 5*c-d*). Second, we performed parallel in vitro/in vitro surface marker and endogenous analysis by flow cytometry. Consistent with the immunohistochemical stainings, endogenous mVenus fluorescence expression showed a remarkable level of heterogeneity in vivo. Compared to in vitro propagated MES-hGICs-MGT $\#1^{dim}$ cells, Xenografts-derived tumor cells showed a minor population of bright MES-hGICs-MGT #1 cells, whereas the vast majority of the tumor cells switched to a MGT $\#1^{low}$ or dark state (FIG. 5*e*). The cell surface receptor CD133, which is routinely used to label tumor-propagating cells in patient-derived xenografts, showed a similar switch from a overall CD133high population in vitro, to a low or negative state. Notably, CD133 expressing cells included a comparable fraction of MGT #1 expressing and non-expressing cells, thereby supporting the ability of MGT #1 to depict functional heterogeneity (FIG. 5*e*).

Overall, our experiments underscore the ability of the sLCRs to illustrate intratumoral heterogeneity (FIG. 5*f*).

Further Experiments to Demonstrate the Feasibility and Implementation of the Invention:

Example 7: Further Characterization of Synthetic Locus Control Regions (sLCRs)

sLCRs are designed to mimic endogenous CREs such as the alpha-globin LCR, which shows position-independent-cell-type- and developmental-stage-specific expression and engages transcription factories. These elements are often defined as super-enhancers and condensate into coactivator puncta. To test whether sLCRs share features with the endogenous LCRs, we measured nascent RNA in MGT #1-transduced cells by RNA-FISH and searched for BRD4 or MED1 condensates using IF. Dual IF and RNA-FISH identified co-localization between BRD4 or MED1 and the nascent RNA of MGT #1 in fixed MGT #1-expressing tumor cells (FIG. 1*g*). Furthermore, both the inducible MGT #1-driven mVenus and the 'housekeeping' PGK-driven H2B-CFP mRNAs were present in the tumor cell cytoplasm but only mVenus was detectable in the nucleus (FIG. 16), indicating a differential strength of the two CREs.

Next, we transduced Proneural (PNGT #1-2) and Mesenchymal (MGT #1-2) sLCRs lentiviral particles into spontaneously immortalized human neural progenitor cells that acquired high copy number of PDGFRA, c-Myc and CDK4. To recapitulate the common PN and MES GBM genetic backgrounds, we further engineered hGICs to be depleted of PTEN and either bear $IDH1^{R132}$ and $TP53^{R273H}$ point mutations or be further depleted of TP53 and NF1, thereby generating PN-hGICs and MES-hGICs, respectively. These cells show DNA methylation profiles similar to GBM patients and acquire subtype-specific gene-expression in vivo and therefore represent two distinct GBM subtypes. Under growth-factor defined conditions in vitro, PNGT #1-2 showed strong expression in both cell types, whereas MGT #1-2 displayed an overall low expression in both genotypes, underscoring the design specificity towards different regulatory networks. Of note, MGT #1 had higher basal expression in MES-hGICs compared to PN-hGICs, indicating a genotype-specific response (FIG. 1*h*).

Thus, we devised a method to systematically generate synthetic LCRs reflecting a given cell identity while preserving critical features of endogenous CREs.

Example 8: Additional Evidence in Support of the Functional Reporter Activity by the sLCRs To investigate adaptive responses to external signaling in MES-hGICs-MGT $\#1^{low}$ and PN-hGICs-MGT $\#1^{low}$ cells, we next performed a phenotypic screening. NBE-propagated hGICs were stimulated with selected factors (cytokines, growth factors, compounds) and FACS analyzed 48 hours after stimulation (FIG. 13*b*). Normalized to the naïve hGICs, sLCRs revealed shared and private responses in MES- and PN-hGICs-MGT $\#1^{low}$ and highlighted TNFα signaling as well as to human serum or FBS and Activin A as MES-GBM regulators. This outcome was reproducible across two independent MES-GBM sLCRs (MGT #1-2) and follow up validation. Instead, the PN phenotype appeared to be less responsive to changes induced by external signaling. (FIG. 13*b-c* and 17). MES GBM specification appeared to be additive to a pre-existing endogenous phenotype as gauged by surface expression of CD133 and PNGT #2. Indeed, TNFα was previously reported as a prominent MES-GBM signaling pathway and inducer of a PN-to-MES transition. Moreover, NFkB (a known TNF-induced TF) was found to engage at least two of the CREs included in the MGT #1 sLCR upon TNFalpha stimulation (FIG. 9*b*). FACS-sorted PN-hGICs-MGT #$1^{low}$ bearing comparable levels of MGT #1 expression as MES-hGICs-MGT #$1^{low}$ still failed to reach similar response to TNFα (FIGS. 2*g* and 8 and 13*a*). Consistently, despite being propagated under the same signaling conditions, MES-hGICs-MGT #$1^{low}$ and PN-hGICs-MGT #$1^{low}$ cells showed differences in endogenous expression and activation of selected signaling pathways (FIG. 2). TNFα stimulation induced phosphorylation of NFkB-p65, STAT3 and p38-MAPK in both cell types but this resulted in a markedly different gene expression output (FIG. 2*d*). These analyses suggest that while TNFα drives a MES GBM signature in MES-hGICs, PN-hGICs commit to a state resembling that of naïve MES-hGICs (FIG. 2*e-f*). Collectively, our results indicate that sLCRs MGT #1-2 reflect the endogenous Mesenchymal GBM gene expression program, while capturing the activation status of signaling pathways (e.g. TNFα) and any pre-existing context-dependent difference (e.g. MES vs PN background).

The observation that pro-differentiation signaling (i.e. Human serum or FBS) drives reporter activation is consistent with previous findings showing that a MES-GBM signature could be attributed to FBS cultured astroglial cells but not to any of the mouse brain cells. Of note, washout experiments suggest that the MES-GBM state is reversible within the timeframe of few days (FIG. 18), indicating that the MES GBM state may be acquired and reversed.

Mesenchymal trans-differentiation in GBM was discovered as a dominant event at recurrence after standard of care and linked to acquired radio-resistance via TNF-driven NFkB activation. A link between inflammatory signaling, EMT, innate immune cells infiltration and radio-resistance is supported by substantial correlative evidence. To experimentally test whether irradiation can induce mesenchymal trans-differentiation in cell autonomous manner, MES-hGICs-MGT #$1^{low}$ and PN-hGICs-MGT #$1^{low}$ cells were exposed to Ionizing Radiation (IR), alone or in combination with TNFα. MGT #1 activation showed a dose-response to increasing IR, whether single or fractionated dose (FIGS. 2*g* and 19). Both MES-hGICs-MGT #$1^{low}$ and PN-hGICs-MGT #$1^{low}$ cells showed an augmented Mesenchymal trans-differentiation in combination with TNFα. A single 10Gy radiation dose is sub-lethal in multiple human GSCs. Likewise, whether alone or in combination with other treatments (e.g. TNFα or Temozolomide), our GICs preserved fitness and displayed residual DNA damage marker gammaH2AX phosphorylation twenty-four hours post irradiation confirming that double-strand breaks had occurred and was under repair (FIG. 2*h*).

Canonical NFkB activation can occur downstream TNFα signaling as well as by non-canonical genotoxic stress. To provide experimental support to the importance of the NFkB in intrinsic and acquired MES-GBM states, we deleted p65IRELA using CRISPR/Cas9 in MES-hGICs, which resulted in marked downregulation of intrinsic MGT #1 expression (FIG. 13*c*). Notably, while TNFalpha ability to induce MES-GBM signaling in polyclonal and monoclonal RELA KO cells was markedly impaired, IkB kinase (IKK) inhibitor-16 further restrained adaptive responses to TNFalpha. In monoclonal RELA KO GICs, we excluded that compensation occurred as a result of RELA KO-escapers, suggesting that other NFkB transcription factors in RELA KO cells may transduce TNF signaling (FIG. 19*b*).

In patients, the GBM stem cell state is dominant to the genetic repertoire in maintaining tumor homeostasis. Next, we wished to test whether sLCRs can be used to discover genes that regulate the MES GBM state by performing a genome-wide pooled CRISPR/Cas9 screen. The genetic screen in MES-hGICs-MGT #$1^{low}$ was performed in their naïve state or when the MES-GBM state was induced by external signaling or genotoxic stress (i.e. FBS+ TNFalpha or TNZ+IR, respectively; FIG. 13*d*). Out of 73,179 gRNAs, the phenotypic screen returned 333 and 1,164 gRNAs associated with MGT #1 high and low factions, respectively (FIG. 13*e*). The effect of the library and treatments over MGT #1 expression, the average statistical depletion of genes associated with fitness but not of the controls, as well as the depletion of two sgRNAs targeting RELA in the naïve state (FIG. 20*a-d*), all suggested that this screen can uncover functional genes. Interestingly, some clinically relevant drug targets such as PARP1 and EED appeared to be critical regulators of MGT #1 activation in all conditions but not essential for proliferation. PARP1 activity is reported as required for IR-induced NF-kB activation and the Polycomb repressor complex 2 scaffold EED inhibition promotes EMT in other contexts. To test whether this approach may be used to prioritize pharmacological treatments leading to cell fate changes, we searched for upstream regulators of the hits. Among others, several gRNAs were previously associated with targets downstream RAR/RXR agonists and MEK1 inhibitors, with a statistical trend for enrichment in MGT #1-low and -high fractions, respectively (FIGS. 13*e* and 20). To validate the prediction that both drugs may have effect over cell fate decisions, we exposed MES-hGICs-MGT #1 to MEK1 selective inhibitor TAK-733 or to All-trans-retinoic acid (ATRA). In both cases, MES-hGICs-MGT #1 responded to short-term TNFalpha stimulation (4 hours) with higher upregulation of both MGT #1 and MES-GBM endogenous markers compared to the TNFalpha alone (FIG. 13*f*), indicating that pre-treatment sensitized these cells to MES GBM program activation. ATRA and TAK-733 sensitized MGT #1 more than EED/EZH2 inhibitors GSK126 did, supporting specificity of the treatments. Thus, sLCRs provide a phenotypic layer of pharmacogenomic information over previous large studies based on fitness alone.

Overall, these results provide experimental evidence for the Mesenchymal GBM to be a transient and reversible cellular state and support robustness and effectiveness of the designed sLCRs in phenotypic screening applications.

Example 9: sLCRs Enable Discriminating Molecularly Diverse Entities

Primary cancer types can be grouped together based on their molecular profile. Chromatin accessibility is the strongest predictor of cancer type similarity and can be used to identify subtype identities within the common dimensional space of individual cancer types. To investigate whether the acquired heterogeneity depicted by sLCRs is accompanied by changes in genome-wide chromatin accessibility, we performed ATAC-seq on MES-hGICs-MGT #$1^{high}$ cells in vitro and in vivo. Differential analysis of chromatin accessibility uncovered many genes undergoing remodeling, notably at driver of PN-to-MES transition WWTR1 (TAZ) and at several TNF receptor gene loci, indicating that genetic tracing for remodeling events that exclusively occur in a physiologically relevant tumor microenvironment (FIG. 14*a-b*). Integration of ATAC-seq data from TCGA and glioma stem cells, further revealed that MES-hGICs-MGT #1$^{high}$ cells represented specific entities within a common glioma space (FIG. 14*c*). Importantly, the unsupervised chromatin profiling of GICs divided by MGT #1 high and low expression grouping those samples into defined clusters (FIG. 14*d*), indicating that MGT #1 expression underlines the acquisition of unique patterns in chromatin accessibility. These results highlight the efficacy of sLCRs in revealing intratumoral heterogeneity and enabling in-depth cellular and molecular characterization of tumor models together with primary cancer data.

Example 10: sLCRs Facilitate the Discovery of Therapeutic Implications for Non-Cell Autonomous Crosstalk Between Tumor and Immune Cells IDH1-wild type GBM infiltration by Glioblastoma-associated microglia/monocytes (GAMs) was recently correlated with NF1 deficiency and a MES-GBM subtype identity but whether there is causal relationship between GAM and MES-GBM remains unresolved. To experimentally test the hypothesis that innate immune cells are causal to rather than being recruited by MES trans-differentiation in NF1-deficient GBM cells, we performed in vitro co-culture of IDH1-wild type and NF1-depleted MES-hGICs-MGT #1$^{low}$ cells with an immortalized human microglia cell line (hMG; cl. C20).

First, we compared the expression of both PN- and MES-sLCR expression by single cells in GBM tumorspheres and multicellular organoid culture conditions. Whereas spheroid culture supports the expansion of stem and progenitor cells with limited spontaneous differentiation and cell death[50,51], glioma organoids give raise to phenotypically diverse cell populations. Resembling the in vivo expression pattern (FIG. 14*a*), we found that MES-hGICs display a heterogeneous PN- and MES-sLCRs expression pattern under organoid conditions and in the presence of human microglia cells as opposed their homogenous expression in pure spheroid cultures (FIG. 15*a*).

Next, we set up a co-culture between homogeneous GBM tumorspheres and hMG cells using trans-well insets. Strikingly, hMG cells drove MGT #1 induction in MES-hGICs to an extent comparable to TNFα (FIG. 15*b*-*c* and 21). In line with previous experiments, hMG activated MGT #1 also in PN-hGIC to a lower extent. In contrast, Myeloid-derived suppressor cells (MDSCs) derived by human CD34+ in vitro only mildly stimulated MGT #1 expression in both lines (FIG. 21). Global transcriptome analysis of MES-hGICs-MGT #1$^{high}$ cells from both conditions revealed common and private NF□B-related gene activation and provided evidence that adaptive immune cells drive a specific MES-GBM state, which shared targets with patients' signature to a large extent (FIG. 15*d*). Interestingly, we found no evidence of TNFα expression by either cell type. Rather, a metabolic transcriptome remodeling featuring genes in the cholesterol biosynthesis pathway appeared to constitute a MES-hGICs signature specific for co-culture with hMG cells (FIG. 15*e*-*g*). These data indicate that activation of NFkB in tumor cells is primarily due to innate immune cells. In fact, inflammatory mediators derived from the adaptive immune system IFNgamma and IL-2, and stroma-derived IL-6 did not trigger direct MGT #1 activation to a comparable extent (FIG. 17), collectively providing experimental insights into the cascade of events leading to a MES-GBM state in vivo.

EMT has been linked to resistance to chemotherapy but also offers therapeutic opportunities. DNA damage stress is the main therapeutic component of the standard of care in GBM, otherwise referred to as the Stupp protocol. A TNF-NFkB signature in GBM was previously linked to the mesenchymal state and radio-resistance in a large cohort of patients and PDX models. Thus, we next exploited sLCRs' ability to identify a MES homeostate in order to explore the therapeutic implications of the microglia-driven GBM state To this end, we FACS-sorted MGT #1-2high and MGT #1-2$^{low}$ MES- and PN-hGICs cells after hMG-driven conversion and exposed these cells to a selected set of standard and targeted chemotherapeutics. Strikingly, in contrast to their sLCR-low counterpart. both MES-hGICs-MGT #1$^{high}$ or -MGT #2high cells proved to be more resistant to DNA damage-based therapeutics (Olaparib, ATR inhibitor VE-821, Topotecan, Mitomycin C) and LXR623, an LXR agonist regulating cholesterol efflux. (FIGS. 15*h* and 21). Importantly, MES-hGICs-MGT #1$^{high}$ cells retained a similar sensitivity profile to targeted agents such as BAY11-7085 (IκB), WP1066 (STAT3; FIGS. 15*h* and 21). The altered chemosensitivity profile of the MES-hGICs-MGT #1$^{high}$ is consistent with the gene expression changes driven by hMG cells, including an impaired the DNA damage gene signature expression in MES-hGICs-MGT #1$^{high}$ cells, a cell cycle profile shift together with the over-expression of a patient-derived MES-GBM and cholesterol biosynthesis signatures (FIG. 21). Similar results were obtained with a Proneural genotype, indicating that hMG cells can divert hGICs into two functionally and therapeutically distinct states and supporting the use of sLCRs in target discovery platforms to integrate complex responses associated with tumor heterogeneity Collectively, our results casually link the innate immune cells to a MES-GBM state and highlight the potential for sLCR to mechanistically dissect relevant non-cell autonomous interactions in vivo and ex vivo.

FURTHER ADVANTAGES AND IMPLEMENTATION OF THE INVENTION

Our understanding of complex cellular and molecular mechanisms at organismal level currently rests largely on in vivo experiments and is limited by the available technologies for genetic tracing. We have established a systems biology framework that allows generating synthetic reporters capable of intercepting cell intrinsic and non-cell autonomous signaling. These sLCRs can be used to illustrate genotype-to-molecular and cellular phenotype transitions in vitro and in vivo. Experimentally, sLCR may be used in characterizing molecular mechanisms linking biological, chemical and environmental stimuli to cell fate transitions, including through chemical and forward genetic screens.

We have applied this approach to investigate cellular and molecular features of GBM subtype expression profiles. The identification of Proneural and Mesenchymal GBM subtype has been consistent across expression platform (microarrays, RNA-seq), readouts (gene expression, DNA methylation) and patients' populations (Western and Chinese). Despite such an extensive effort, GBM subtypes' significance remains elusive when it comes to their origin, location or spatiotemporal evolution.

By combining near-isogenic models and a MES sLCR, we show that the most significant component to the MES-GBM specification is adaptive in nature. Despite a genotype-instructed intrinsic MES signaling exemplified by MES-hGICs showing a measurable but moderate difference in expression of a MES sLCRs when compared to PN-hGICs, TNF signaling as well as pro-differentiation stimuli (e.g.

FBS) are major triggers of MES signaling. Interestingly, TNFα and FBS both trigger MES trans-differentiation by differentially impacting cell morphology. Both kind of responses appear to be engraved in vivo, as inferred by the extent of heterogeneity in MGT #1 expression and markers of undifferentiated and self-renewing tumor cells. Our experiments link the MGT #1 readout in GBM cells to the expression of migration-associated markers such as CD44, response to pro-inflammatory microenvironment and resistance to sub-lethal doses of genotoxic stress, all of which represent the hallmarks of tumor progression, including in GBM at single cell levels[18]. These findings illustrate the power of MGT #1 to elucidate cellular and molecular mechanisms in GBM.

This technology enables transforming cellular and molecular profiling into phenotypic maps, which may fulfill the experimental needs associated with the continuous mapping of cellular and molecular features in health and disease, including at single-cell level. In fact, sLCR improve in vivo phenotypic assays that still represent obligatory steps towards the full understanding of complex cellular and molecular mechanisms at organismal level. As such, it offers significant ex vivo opportunities.

We show that sLCRs reflecting in vivo regulatory networks accurately intercepted cell intrinsic and non-cell autonomous signaling and were successfully applied to dissect genotype-to-molecular and cellular phenotype transitions in vitro and in vivo. We demonstrate the utility of this system by investigating the cellular and molecular basis of GBM subtype expression profiles. The identification of Proneural and Mesenchymal GBM subtype has been consistent across expression platform (microarrays, RNA-seq and single-cell RNA-seq), readouts (gene expression, DNA methylation) and patients' ethnicity (Western and Chinese). Despite such an extensive effort, significance of GBM subtypes remains elusive when it comes to their origin, location or spatiotemporal evolution and—more importantly—to their therapeutic significance.

The Proneural and Mesenchymal GBM programs rely on the activity of specific transcription factors. Here, we integrated near-isogenic models and cell lines with sLCRs and the results are consistent with the PN-GBM being the default GBM entity that strongly depends on RTK signaling and is therefore promoted by neural stem cells culture conditions. Instead, we show that the most significant component to the MES-GBM specification is adaptive in nature. In absence of a tumor microenvironment, the PN state appears hardwired even in cells with MEG-GBM genotype (e.g. NF1 depletion) but the MES identity is swiftly amplified by acute inflammatory and pro-differentiation stimuli (e.g. TNF signaling as well as bovine or human serum). Interestingly, in different cell types, MES trans-differentiation measured by sLCRs can occur along with differentially impacting cell morphology. Our experiments link MES-sLCRs readout in GBM cells, feed-forward responses to pro-inflammatory microenvironment, resistance to sub-lethal doses of genotoxic stress and expression of migration-associated markers such as CD44, all of which represent the hallmarks of progression in human cancer, including in GBM at single cell levels. These features appear to be engraved in tissue homeostasis, as inferred by clustered cellular expression pattern ('homeostases') and heterogeneity in tumor models in vivo and ex vivo.

Genetic tracing of MES-GBM principle components in three different cancer types underscores the tissue-independent ability of our sLCRs to reveal tumor homeostates and provides further evidence that EMT represents hijacking of a developmental cellular process. These findings illustrate the versatility of sLCRs in elucidating cellular and molecular mechanisms in multifactorial diseases. Further, the use of sLCRs in pharmacogenomics could significantly accelerate translational medicine by uncovering phenotype-specific dependencies and resistance.

Finally, sLCR enabled the mechanistic dissection of the pathophysiologically relevant non-cell autonomous interactions between innate immune cells and tumor cells. GAMs are believed to constitute the source for TNFα in both glioma mouse models and human tumors. Our results provide experimental support to the clinical association between the MES-GBM subtype and specific immune landscapes and uncover TNFα-independent routes to MES GBM. Importantly, the GAM-driven MES-GBM state herewith identified shows an extent of overlap with patients' signatures, which is comparable to that of individual patients' signature themselves.

In summary, sLCR were shown to be of use in characterizing molecular mechanisms by linking biological, chemical and environmental stimuli to cell fate transitions, including through chemical and genetic screens. Previous attempts to generate synthetic reporters using massively parallel sequencing or mixed models revealed the potential use of this approach and the limitations associated with limited control over the design. Our method substantially addressed this problem and represent a base for future development, ranging from the linear improvement on basic design components (e.g. using curated resources of TFBS and cis-elements) to the systematic generation and validation of large numbers sLCR followed by machine learning of successful features. In parallel, robust cell-type- or state-specificity and granularity may be extended by combining sLCR with DNA barcoding. Tunable operations may be achieved by coupling sLCRs transcriptional inputs with synthetic effector proteins enabling Boolean logic outputs. Thus, genetic tracing by sLCRs is scalable and can be extended to virtually any given system, whether ex vivo or in vivo to dissect cell intrinsic and non-cell autonomous mechanisms controlling normal and diseased homeostasis.

REFERENCES

1. Kretzschmar, K. & Watt, F. M. Lineage tracing. *Cell* 148, 33-45 (2012).
2. Barker, N. et al. Identification of stem cells in small intestine and colon by marker gene Lgr5. *Nature* 449, 1003-1007 (2007).
3. Barker, N., Tan, S. & Clevers, H. Lgr proteins in epithelial stem cell biology. *Development* 140, 2484-2494 (2013).
4. Livet, J. et al. Transgenic strategies for combinatorial expression of fluorescent proteins in the nervous system. *Nature* 450, 56-62 (2007).
5. Liu, C. et al. Mosaic analysis with double markers reveals tumor cell of origin in glioma. *Cell* 146, 209-221 (2011).
6. Schwitalla, S. et al. Intestinal Tumorigenesis Initiated by Dedifferentiation and Acquisition of Stem-Cell-like Properties. *Cell* (2012). doi:10.1016/j.cell.2012.12.012
7. Schepers, A. G. et al. Lineage tracing reveals Lgr5+ stem cell activity in mouse intestinal adenomas. 337, 730-735 (2012).
8. Driessens, G., Beck, B., Caauwe, A., Simons, B. D. & Blanpain, C. Defining the mode of tumour growth by clonal analysis. *Nature* (2012). doi:10.1038/nature11344

9. Oshimori, N. & Fuchs, E. Paracrine TGF-β Signaling Counterbalances BMP-Mediated Repression in Hair Follicle Stem Cell Activation. Cell Stem Cell 10, 63-75 (2012).

10. Chen, J. et al. A restricted cell population propagates glioblastoma growth after chemotherapy. *Nature* (2012). doi:10.1038/nature11287

11. Zhu, L. et al. Multi-organ Mapping of Cancer Risk. *Cell* 166, 1132-1146.e7 (2016).

12. Church, G. M., Elowitz, M. B., Smolke, C. D., Voigt, C. A. & Weiss, R. Realizing the potential of synthetic biology. *Nat Rev Mol Cell Biol* 15, 289-294 (2014).

13. Stupp, R. et al. Effects of radiotherapy with concomitant and adjuvant temozolomide versus radiotherapy alone on survival in glioblastoma in a randomised phase III study: 5-year analysis of the EORTC-NCIC trial. *Lancet Oncol.* 10, 459-466 (2009).

14. Wang, Q. et al. Tumor Evolution of Glioma-Intrinsic Gene Expression Subtypes Associates with Immunological Changes in the Microenvironment. *Cancer Cell* 32, 42-56.e6 (2017).

15. Noushmehr, H. et al. Identification of a CpG island methylator phenotype that defines a distinct subgroup of glioma. *Cancer Cell* 17, 510-522 (2010).

16. Verhaak, R. G. W. et al. Integrated genomic analysis identifies clinically relevant subtypes of glioblastoma characterized by abnormalities in PDGFRA, IDH1, EGFR, and NF1. *Cancer Cell* 17, 98-110 (2010).

17. Sottoriva, A. et al. Intratumor heterogeneity in human glioblastoma reflects cancer evolutionary dynamics. *Proc Natl Acad Sci USA* 110, 4009-4014 (2013).

18. Lee, J.-K. et al. Spatiotemporal genomic architecture informs precision oncology in glioblastoma. *Nature Genetics* 49, 594-599 (2017).

19. Phillips, H. S. et al. Molecular subclasses of high-grade glioma predict prognosis, delineate a pattern of disease progression, and resemble stages in neurogenesis. *Cancer Cell* 9, 157-173 (2006).

20. Bhat, K. P. et al. *Mesenchymal Differentiation Mediated by NF-KB Promotes Radiation* Resistance in Glioblastoma. *Cancer Cell* 24, 331-346 (2013).

21. ENCODE Project Consortium et al. Identification and analysis of functional elements in 1% of the human genome by the ENCODE pilot project. *Nature* 447, 799-816 (2007).

22. Thurman, R. E., Day, N., Noble, W. S. & Stamatoyannopoulos, J. A. Identification of higher-order functional domains in the human ENCODE regions. *Genome Res* 17, 917-927 (2007).

23. Kim, T. H. et al. Analysis of the vertebrate insulator protein CTCF-binding sites in the human genome. *Cell* 128, 1231-1245 (2007).

24. Ong, C.-T. & Corces, V. G. CTCF: an architectural protein bridging genome topology and function. *Nat Rev Genet* 15, 234-246 (2014).

25. Lee, J. et al. Tumor stem cells derived from glioblastomas cultured in bFGF and EGF more closely mirror the phenotype and genotype of primary tumors than do serum-cultured cell lines. *Cancer Cell* 9, 391-403 (2006).

26. Ozawa, T. et al. Most Human Non-GCIMP Glioblastoma Subtypes Evolve from a Common Proneural-like Precursor Glioma. *Cancer Cell* 26, 288-300 (2014).

27. Quail, D. F. et al. The tumor microenvironment underlies acquired resistance to CSF-1R inhibition in gliomas. *Science* 352, aad3018 (2016).

28. Szulzewsky, F. et al. Human glioblastoma-associated microglia/monocytes express a distinct RNA profile compared to human control and murine samples. *Glia* 64, 1416-1436 (2016).

29. a Dzaye, 0. D. et al. Glioma Stem Cells but Not Bulk Glioma Cells Upregulate IL-6 Secretion in Microglia/Brain Macrophages via Toll-like Receptor 4 Signaling. *J. Neuropathol. Exp. Neurol.* 75, 429-440 (2016).

30. Inda, M.-D.-M. et al. *Tumor heterogeneity is an active process maintained by a mutant* EGFR-induced cytokine circuit in glioblastoma. *Genes Dev* 24, 1731-1745 (2010).

31. Hossain, A. et al. *Mesenchymal Stem Cells Isolated From Human Gliomas Increase* Proliferation and Maintain Stemness of Glioma Stem Cells Through the IL-6/gp130/STAT3 Pathway. *Stem Cells* 33, 2400-2415 (2015).

32. Midwood, K. et al. Tenascin-C is an endogenous activator of Toll-like receptor 4 that is essential for maintaining inflammation in arthritic joint disease. *Nat Med* 15, 774-780 (2009).

33. Jachetti, E. et al. Tenascin-C Protects Cancer Stem-like Cells from Immune Surveillance by Arresting T-cell Activation. *Cancer Res* 75, 2095-2108 (2015).

34. Stanzani, E. et al. Radioresistance of mesenchymal glioblastoma initiating cells correlates with patient outcome and is associated with activation of inflammatory program. *Oncotarget* 8, 73640-73653 (2017).

35. Bao, S. et al. Glioma stem cells promote radioresistance by preferential activation of the DNA damage response. *Nature* 444, 756-760 (2006).

36. Hinz, M. et al. A cytoplasmic ATM-TRAF6-cIAP1 module links nuclear DNA damage signaling to ubiquitin-mediated NF-κB activation. *Mol Cell* 40, 63-74 (2010).

37. Lei, L. et al. Glioblastoma models reveal the connection between adult glial progenitors and the proneural phenotype. *PLoS ONE* 6, e20041 (2011).

38. Rheinbay, E. et al. An Aberrant Transcription Factor Network Essential for Wnt Signaling and Stem Cell Maintenance in Glioblastoma. *Cell Rep* (2013). doi: 10.1016/j.celrep.2013.04.021

39. Kalluri, R. & Weinberg, R. A. The basics of epithelial-mesenchymal transition. *Journal of Clinical Investigation* 119, 1420-1428 (2009).

40. Baird, R. D. & Caldas, C. Genetic heterogeneity in breast cancer: the road to personalized medicine? *BMC Med* 11,151 (2013).

41. Serresi, M. et al. Polycomb Repressive Complex 2 Is a Barrier to KRAS-Driven Inflammation and Epithelial-Mesenchymal Transition in Non-Small-Cell Lung Cancer. *Cancer Cell* 29, 17-31 (2016).

42. Wamsley, J. J. et al. Activin upregulation by NF-κB is required to maintain mesenchymal features of cancer stem-like cells in non-small cell lung cancer. *Cancer Res* 75, 426-435 (2015).

43. Shao, D. D. et al. KRAS and YAP1 converge to regulate EMT and tumor survival. *Cell* 158, 171-184 (2014).

44. Ohinata, Y., Sano, M., Shigeta, M., Yamanaka, K. & Saitou, M. A comprehensive, non-invasive visualization of primordial germ cell development in mice by the Prdm1-mVenus and Dppa3-ECFP double transgenic reporter. *Reproduction* 136, 503-514 (2008).

45. Gargiulo, G. et al. In vivo RNAi screen for BMII targets identifies TGF-β/BMP-ER stress pathways as key regulators of neural- and malignant glioma-stem cell homeostasis. *Cancer Cell* 23, 660-676 (2013).

46. Gargiulo, G., Serresi, M., Cesaroni, M., Hulsman, D. & Van Lohuizen, M. In vivo shRNA screens in solid tumors. *Nat Protoc* 9, 2880-2902 (2014).

47. Li, P., Markson, J. S., Wang, S., Chen, S., Vachharajani, V., and Elowitz, M. B. (2018). Morphogen gradient reconstitution reveals Hedgehog pathway design principles. Science 360, 543-548.
48. Blankvoort, S., Witter, M. P., Noonan, J., Cotney, J., and Kentros, C. (2018). Marked Diversity of Unique Cortical Enhancers Enables Neuron-Specific Tools by Enhancer-Driven Gene Expression. Curr Biol 28, 2103-2114.e2105.
49. Takahashi, K., and Yamanaka, S. (2006). Induction of pluripotent stem cells from mouse embryonic and adult fibroblast cultures by defined factors. Cell 126, 663-676.
50. Suvà, M.-L., Rheinbay, E., Gillespie, S. M., Patel, A. P., Wakimoto, H., Rabkin, S. D., Riggi, N., Chi, A. S., Cahill, D. P., Nahed, B. V., et al. (2014). Reconstructing and Reprogramming the Tumor-Propagating Potential of Glioblastoma Stem-like Cells. Cell
51. Frith, M. C., Fu, Y., Yu, L., Chen, J.-F., Hansen, U., and Weng, Z. (2004). Detection of functional DNA motifs via statistical over-representation. Nucleic Acids Res 32, 1372-1381
52. Phillips, H. S., Kharbanda, S., Chen, R., Forrest, W. F., Soriano, R. H., Wu, T. D., Misra, A., Nigro, J. M., Colman, H., Soroceanu, L., et al. (2006). Molecular subclasses of high-grade glioma predict prognosis, delineate a pattern of disease progression, and resemble stages in neurogenesis. Cancer Cell 9, 157-173.
53. Verhaak, R. G. W., Hoadley, K. A., Purdom, E., Wang, V., Qi, Y., Wilkerson, M. D., Miller, C. R., Ding, L., Golub, T. R., Mesirov, J. P., et al. (2010). Integrated genomic analysis identifies clinically relevant subtypes of glioblastoma characterized by abnormalities in PDGFRA, IDH1, EGFR, and NF1. Cancer Cell 17, 98-110.
54. Sturm, D., Witt, H., Hovestadt, V., Khuong-Quang, D.-A., Jones, D. T. W., Konermann, C., Pfaff, E., Tönjes, M., Sill, M., Bender, S., et al. (2012). Hotspot Mutations in H3F3A and IDH1 Define Distinct Epigenetic and Biological Subgroups of Glioblastoma. Cancer Cell 22, 425-437.

The invention claimed is:

1. A method for generating a cell-type specific expression cassette, comprising the steps of:

a) providing a gene expression profile of a cell type of interest, b) providing genomic sequence data of said cell type of interest, c) selecting a set of signature genes from the gene expression profile, wherein said signature genes are (i) differentially regulated compared to a reference cell type or (ii) selected according to a gene expression level, d) identifying genes encoding a transcription factor within the set of signature genes selected in c), e) determining a set of genomic regions from the genomic sequence data, wherein each genomic region comprises a sequence encoding a signature gene identified in c) and additional genomic sequence adjacent to the sequence encoding said signature gene, f) identifying multiple genomic sub-regions of comparable and limited size, within the set of genomic regions determined in e), wherein said genomic sub-regions comprise one or more binding sites for one or more of the transcription factors identified in d), g) selecting a minimal set of genomic sub-regions from those determined in f), wherein the set of genomic sub-regions is selected to comprise transcription factor binding sites for a predetermined percentage of all transcription factors identified in d), h) generating a cell-type specific expression cassette comprising the set of genomic sub-regions selected in step g) operably coupled with a reporter or effector gene, wherein the genomic sub-regions are configured to regulate the expression of said reporter or effector gene, wherein the set of genomic sub-regions selected in step g) forms a synthetic regulatory region comprising 2 to 10 of said genomic sub-regions, each comprising 100 bp to 1000 bp, positioned adjacently, without a linker or with a linker sequence of less than 100 bp positioned between two or more of said sub-regions, wherein said genomic sub-regions originate from separate and non-adjacent locations in the same genome of said cell type of interest, and i) synthesizing, cloning, and/or isolating a nucleic acid molecule comprising the generated cell-type-specific expression cassette of step h).

2. The method for generating an expression cassette according to claim 1, wherein the gene expression profile comprises expression levels of genes in the cell type of interest, and according to step c) (i) a gene expression profile of a reference cell type is provided, comprising expression levels of genes in the reference cell type, and differentially regulated signature genes are selected by identifying genes that are up- or down-regulated compared to the expression levels in the reference cell type, or according to step c) (ii) the genes of the cell type of interest are ranked according to their gene expression level and signature genes are selected based on expression of a predetermined level or a predetermined number of signature genes.

3. The method for generating an expression cassette according to claim 1, wherein the predetermined percentage of transcription factors covered is 30% or more.

4. The method for generating an expression cassette according to claim 1, wherein the genomic regions determined in e) correspond to genomic sequences of topological associating domains that contain the differently regulated gene.

5. The method according to claim 4, wherein the topological associating domain corresponds to a genomic sequence between two CTFC-binding sites located outside the coding region of and including the signature genes.

6. The method for generating an expression cassette according to claim 1, wherein the identifying genomic sub-regions of equal size in step f) is performed by a sliding window algorithm of the genomic regions determined in e), wherein the window has a length of 500 bp to 5000 bp, and the sliding step has a length of 100 bp to 1000 bp.

7. The method according to claim 6, wherein the window has a length of 700 bp to 2000 bp or 800 bp to 1200 bp, and the sliding step has a length of 120 bp to 300 bp or 130 bp to 170 bp.

8. The method for generating an expression cassette according to claim 1, wherein the selection of a set of genomic sub-regions in g) is performed by calculating for each genomic sub-region identified in f): an enrichment of binding sites for the transcription factors according to d) in the genomic sequence data, and a score for the diversity of transcription factors for which binding sites are present, wherein the genomic sub-regions are ranked according to the cumulative percentage of transcription factors for which binding sites are present, and wherein a minimal set of genomic sub-regions is selected to comprise binding sites for a predetermined percentage of all transcription factors identified in d).

9. A cell-type specific reporter vector in the form of a nucleic acid molecule, comprising the cell-type-specific expression cassette generated by the method according to claim 1.

10. The method according to claim 1, wherein the minimal set of genomic sub-regions comprises 2 to 10 genomic sub-regions, from those determined in step f) of claim 1.

11. The method according to claim 1, wherein differentially regulated signature genes are 3- to 10-fold upregulated in the cell type of interest, or wherein the signature genes selected based on expression of a predetermined level or a predetermined number of signature genes are the 100 to 1000 most highly expressed, or 100 to 1000 most lowly expressed genes in the cell type of interest.

12. The method for generating an expression cassette according to claim 1, comprising 3 to 10 of said genomic sub-regions.

* * * * *

SEQUENCE LISTING

<160> NUMBER OF SEQ ID NOS: 6

<210> SEQ ID NO 1
<211> LENGTH: 827
<212> TYPE: DNA
<213> ORGANISM: Artificial Sequence
<220> FEATURE:
<223> OTHER INFORMATION: sLCR

<400> SEQUENCE: 1
atatttattt ttaggaccag aaagttaaag tgaattggat ttgatccatt ttctgaaagg 60
ctggcaagaa ttcttgacat tgcacaggaa tttccatgtc agcatgttct cacatgtatg 120
atctaattta gagattattt tggggggcgg gggttgagga aatggcatga ctcagagttt 180
aaaagcccca aatcttagct gtgcctgtgt agctttacca cataacccat tgataactta 240
gttgtgcaac catcaccacc atctgttttc agaactcttt tcattttgcg aaactgaaac 300
ccgttaagca ctgatttccc actctccctc ctcccagccc atagcaaacc accatcccac 360
cagcactttc atttcgcaaa tggcaaaact gaagccgata ttgtggttgt gacttatccc 420
aaagtaatat acacataaac ctctatggat gaggaaaaag acagagggaa actaaaaatt 480
caaaagaaca aatttgactc acagatttgc tgactcatag ttgtgacact tcctggctca 540
ggaagttgaa tttcattaag cctttgtggt ttggggctct gctgtgcttt gacagctctg 600
atctcctccc ttccggctgg gctgtctggg gcgctctaaa atgagtgttg atttaatgca 660
ctgccttcgc acccgtgctg gtgcgtcccg gggacagggg tggctgtgcg gtgccgcggc 720
ggccggcggg gctccttccc cagcaggggt ggggacgctg agtcacggat ctgtcaccgc 780
tttgcacctc tccgagccct cgggggccaa agcaaaagcg aaagcga 827

<210> SEQ ID NO 2
<211> LENGTH: 1015
<212> TYPE: DNA
<213> ORGANISM: Artificial Sequence
<220> FEATURE:
<223> OTHER INFORMATION: sLCR

<400> SEQUENCE: 2
ctagaacagc agggccacct ccttctctcc cccgcgggca tgggccccca cccccactgc 60
cggcagagtg ctgaggactc gtgcaccatg agaacttctg accatgagaa ctttgacttc 120
cggatttggg ggatctgccc aggtgaacac aatgcaaggg gctgcatgac ctaccaggac 180
agaactttcc ccaattacag ggtgactcac agccgcattg gtgactcact tcaatgtgtc 240
atttccggct gctgtgtgtg agcagtggac acgtgagggg ggggtgggtg agagagacag 300
gccacattgt gcaacagatc tctagagctt tttcatcttg caaaactgaa actgtatacc 360
catggaacaa cagctccctg ctcccctccc cctcagctcc tgggtagtga catttcttga 420
ttctcagtaa actatcacaa gaacaaaaaa ccaaacaccg catattctca ctcataggtg 480
ggaattgaac aatgagatca catggacaca ggaaggggaa tatcacactc tggggactgt 540
ggtggggtgg ggggagtggg gagggatagc actgggatgt cccaagagaa ggggaagagg 600
gggaggtgtt agagaacttg tgtgttcaac cgaaacatga tgaaaacagg gaaagccccc 660
aagatacctg tcattcccga tgatgtcaga ttcagcaaat tcaatgataa caaaacatta 720
tgaaaaaatt agtaattaaa ataatacagc aatgtgtatg aacaaaataa tcaatgaaag 780
tgaaacctaa tagtaattcc acaaacttat tacaaagcta ttaatttaaa gagtagtggc 840
aattgaaaac cacaaccaac accagtgctt acagcagcaa tacttttact cagacttcct 900
gtttctggaa cttgccttct tttttgctgt gtttatactt cccttgtctg tggttagata 960
agtataaagc cctagatcta agcttctctg tcttcctccc tccctccctt cctct 1015

<210> SEQ ID NO 3
<211> LENGTH: 1050
<212> TYPE: DNA
<213> ORGANISM: Artificial Sequence
<220> FEATURE:
<223> OTHER INFORMATION: sLCR

<400> SEQUENCE: 3
agagctcctg gccaaggtct ttgtgttcag accagaagag gaaggagggc tccctccccc 60
tggggctgtg gaggctgagg ctcctggggg gttgtccaca tctggaccgt gggagctgtt 120
ggggggaatg gggcaggtgg gagaagagga taagcagctg attgggccca gactactctg 180
ggctggctcc atcttacatg actgccacaa acagctgcag gagtgtgaca gatcacaaca 240
ctagcattgt acctcaaaat atgcttgtac cctaaggcac aagaactggt ttgacttaca 300
accgcagccc ccgtccgggc accccgaggc ccgcgggagc caccctcgaa ccccggccgc 360
gcacgggcgg ggcggcgcgc acctgccggg agcccgtgtt tgtaaacaaa ccgcgcgcct 420
aattagcctg gcgggagcgc gcgcgcgggg cggggggcgg ggcgtcggtg cgcgcgggca 480
ggtcggcccc gcccggggag gagccgcgct ctgccgcgcc ctccgtgtca ccatctcccc 540
cacccgactt ggcggggcgc gggcttgctg gagcctgcgg gacccagagc ccgctccgga 600
gccagccctg ggagtggcca gcttgaaccc gagggccccg cagaccgtta ctccggcccc 660
cgcccggggc ggggcgcgcg ggggcgcggc gcagcccaac ccgcacagcc gcgtccccaa 720
acaccaccga ggagggaaaa cagacggaga ggggtggggc tgcgggcggg gccggcgcct 780
aattgggccg cgggcgcctc gaggtgggcg gggcataagg gggcggggcc gcggagaccc 840
cgggcgggag cagggagagg aaagaagaga ctgagtacgc ggagaccgag attcggaaat 900
atttctgcct taattgttct tccattgtct ttctcctgtg ggtcccctct cacctttctg 960
tatggtcctg gatcaccccc cgaggctttg tctcccccat ccacgggctt attctctcgg 1020
cacccccttc ctctcccgtc atcggttgat 1050

<210> SEQ ID NO 4
<211> LENGTH: 1164

<212> TYPE: DNA
<213> ORGANISM: Artificial Sequence
<220> FEATURE:
<223> OTHER INFORMATION: sLCR

<400> SEQUENCE: 4
ttaattaatc cctcctctaa tccctccagc gggatcaggg aggaggtgcg ggacctgctg 60
ccccgggctt gcccccatcc cggcctcacg catgggcgcc tgtctcagcc ctctcccagg 120
acgctgcagg tgtggctggg ccagcgctaa ttagtgggcc gcgcgggggc cccgctgagc 180
ctttgacaga aaaggcggta gggaggtggg ggcagggagg cgctccacca gccagaagtc 240
cggagcgcaa cccaaagtac tccatctcaa aagaaaaaag gcgggggcgg tggggggggg 300
gggtgatttc agtacaaagc ctacagacat tataaaaata ttaagatttt tgttcgtttg 360 tttttgttt ttgagacaga gtctcactgt cacccccagg ctggagtctg tgccggcgcc 420
cgctgcttcg catctgcgcg cccgcccggt gccgggcccc gccctccgcc tcagccccaa 480
gctcggcccg cgggcccggc cacaggtgcc ccggcggccc cgcctggccc gagggaagag 540
ggcagctggg aggggcccat gagagaacca aaactgtgcc cccaggcttg gaaagaaatc 600
acatgtatgg ccagcaggaa ggttccggaa ggttccggag gacacctgca ggtgggactg 660
agaacagggg tctcggctgg gagtggctga ggccatatga ggacctcgac tgccacaaac 720
agctgcagga gtgtgacaga tcacaacact agcattgtac ctcaaaatat gcttgtaccc 780
taaggcacaa gaactggttt gacttacaaa actgatctca gagttgggat caaagttttt 840
ctaccactct actatgagcc ctcggccggg ccccgccccg ccagctccgc gcggctctgg 900
gctctctagg ggtggggctg cgggcggggc cggcgcctaa ttgggccgcg ggcgcctcga 960
ggtgggcggg gcataagggg gcggggccgc ggagaccccg ggcgggagtt tttttctgca 1020
agcgagaggg ggggtgttgt tggtatcgcc ccctccttct cctcccccca ggggtgaaag 1080
tgcaagagga agtgcagccg ctgccatctt tcctccgctc cgaacacacg gagcccgggg 1140
ccgcacagcc gccgctcctg taca 1164

<210> SEQ ID NO 5
<211> LENGTH: 1110
<212> TYPE: DNA
<213> ORGANISM: Artificial Sequence
<220> FEATURE:
<223> OTHER INFORMATION: sLCR

<400> SEQUENCE: 5
atggtctcaa tctcctgacc ttgtgatccg cccacctcgg cctcccaaag tgctgggatt 60
acaggtgtga gccaccacgc ccagccgaca gtcccttatc tggttcatct tcgtacctct 120
aaaagtcagc atggatgctc tattaatgat atatttatac atattagcaa caaacaattg 180
gaaactaaaa ctttaaaaag acattctcac acctgtaatc ccagcatgtt gggaggtcga 240
ggcaggcgaa tcacgaggtc aggagttcga gaccagcctg gccaacatgg tgaaactctg 300
gaagaccgaa actattcagc aagaactaag aaccacaatg ttaaggggggt ccattgttta 360 ttttttttc tttagaggat gaaaaccaaa ggtcaggtga tttaatttaa aattaacact 420
cttatttttt gcccgcccgc ctgcctgcct ctttacaatt tacagaatgt cttaaggtag 480
ttaagtttca agtttttctt tctcagtatc ctaccttcat gcatcaaagt gggtggcctt 540
tatcccatta acggcaatta cgtaagacag atgtccctag atgaaatctt acagttcttt 600
tagtcagacc ccccaccccg ccaccgccac cagacaccac catcgctgtg tagtgtgggt 660

-continued ttttattcgt gttcgtgtgt gtgtgtggac acattttcct tttcggttgc tctgtccttt 720
ggttcgtgct cgcctcgctt tttccacact cctgctctct ggctctctgt gtctctcgct 780
ctttcgaaaa ttttcctaag tccgggcgcg cgctccctcc ccttccgccc accccagccc 840
ctcggcggcg cccgcgggag ggggaggagg cctcgggggc gccgggcgac gcggtccggg 900
gggtggagcg ttggcgtcgt gcgaggggtc gtcactggcg cggagacgcc ccctctcccc 960
cctcggctca gccgggctgc tgcccgagcc cggggggtgg ggggcgtctc cccggcccgt 1020
cccgtccccg gccgggcgcg ggcggaggga ccccctcccc gggctcccgg ggggccgcct 1080
ccctccgccg gctcccgccc tcccagccgc 1110

<210> SEQ ID NO 6
<211> LENGTH: 1112
<212> TYPE: DNA
<213> ORGANISM: Artificial Sequence
<220> FEATURE:
<223> OTHER INFORMATION: sLCR

<400> SEQUENCE: 6
ttaattaaga atatctggct ggccacgtgt ttgtaaagaa aaaccaagac ggccaggcga 60
ggtggctcac acctgtaatc ccagcacttt gggaggccga ggcgggcgct gcccttcggc 120
cttcaaggag gaattcctac tgtttatgaa gatcgggttt gggtttttgg ttttttttt 180 ctttttcttt tttccgtggt ggtggtgggt gggcttttgt tctttttgtt ttttctgtgg 240
tggtggtggg tgggctttat gaatatacca tattttgcct attgtttttc tatttatcag 300
gtggtgtcat ttgagttgtt ttcaccctct tgtgactatg aataatgata ctataaacaa 360
tcttatacag catcagtgtc aaaaatcact aacattccta tacacagacg tgactaaact 420
tccagcttgg ggtcccgtgg acctgcagcc aggtgcagca ggtcacaggg caaggacacg 480
tgtcattggt gaccttcact attcagtgcc cagatgctca gtgctctgtg caggccacct 540
ggctggtctc aggtaccgct gctctgtctc gctcaccggc cgggctatgt tgattgtccc 600
ctcgcggcgc ccggaagcga ccctcagtaa acaaagccgt gtgtgggcgc agccccagaa 660
gcctggggcg cgcagtccag cccaagagag gcgggggagg aatgttgtga atgaaccccg 720
ggcccgcccc gaaactccgc ataaggcctg ggccgcgggg gtcctcccac tctgattggc 780
ctctggcgcc ccgtgattga cagcgcccct cgctgtgcgc tctggttggg taaacaagaa 840
aagactggca tcgcagtcat cgagtgagca gcgaggcttg gacacgggtc tggcggcgca 900
gccaatggcg ggggagggcc gaggaggccg aggggggggcc aatagggaca ggcggtgggg 960
gcgggacgac ggcggagcta aagcggcggc tgaagcagct tcattgttgt gaagagtctt 1020
aaaggggccg catcaccctg ccggcccggc gcgggtcggg ggtgggtgcg gtaggggtcc 1080
cggggcggcc gagcgcagag gacggatgta ca 1112